(12) United States Patent
Lazarovici

(10) Patent No.: US 11,771,468 B2
(45) Date of Patent: Oct. 3, 2023

(54) DEVICES, SYSTEMS AND METHODS FOR DISTRACTION OSTEOGENESIS

(71) Applicant: OSTEOPHILE LTD., Newę Yaraq (IL)

(72) Inventor: Towy Lazarovici, Newe Yaraq (IL)

(73) Assignee: OSTEOPHILE LTD., Newe Yaraq (IL)

(\*) Notice: Subject to any disclaimer, the term of this patent is extended or adjusted under 35 U.S.C. 154(b) by 414 days.

(21) Appl. No.: 16/973,728

(22) PCT Filed: Jun. 30, 2019

(86) PCT No.: PCT/IL2019/050722
§ 371 (c)(1),
(2) Date: Dec. 9, 2020

(87) PCT Pub. No.: WO2020/008450
PCT Pub. Date: Jan. 9, 2020

(65) Prior Publication Data
US 2021/0244444 A1    Aug. 12, 2021

Related U.S. Application Data

(60) Provisional application No. 62/823,012, filed on Mar. 25, 2019.

(30) Foreign Application Priority Data

Jul. 2, 2018 (IL) .......................................... 260367

(51) Int. Cl.
*A61B 17/66* (2006.01)
(52) U.S. Cl.
CPC .................. *A61B 17/666* (2013.01)

(58) Field of Classification Search
CPC ..... A61B 17/66–666; A61C 8/02; A61C 8/00; A61C 8/0006; A61C 8/0027; A61C 8/0083
See application file for complete search history.

(56) References Cited

U.S. PATENT DOCUMENTS 5,067,954 A * 11/1991 Ilizarov ............. A61B 17/6441
606/57
6,171,313 B1 * 1/2001 Razdolsky ........... A61B 17/666
606/86 R
(Continued)

FOREIGN PATENT DOCUMENTS

CN   1044043 A   7/1990
EP   1088520 A2  4/2001
(Continued)

OTHER PUBLICATIONS

Meyer et al., (1999) Strain-related bone remodeling in distraction osteogenesis of the mandible. Plast Reconstr Surg 103(3): 800-807.
(Continued)

*Primary Examiner* — Eduardo C Robert
*Assistant Examiner* — Michelle C Eckman
(74) *Attorney, Agent, or Firm* — The Roy Gross Law Firm, LLC; Roy Gross

(57) ABSTRACT

The present invention relates to the field of devices and methods for distraction osteogenesis, and, more particularly, to distraction devices and distraction systems used in the treatment of mandibular or maxillary alveolar ridge atrophy, and to methods for utilizing a distraction device or a distraction system for bone tensioning.

20 Claims, 42 Drawing Sheets

(56) References Cited

U.S. PATENT DOCUMENTS

| | | | | |
|---|---|---|---|---|
| 8,226,655 | B1* | 7/2012 | Sixto, Jr | A61C 8/0006 |
| | | | | 606/86 R |
| 2004/0152046 | A1* | 8/2004 | Minoretti | A61C 7/20 |
| | | | | 433/18 |
| 2005/0059864 | A1* | 3/2005 | Fromovich | A61C 8/0087 |
| | | | | 600/201 |
| 2005/0159755 | A1* | 7/2005 | Odrich | A61B 17/666 |
| | | | | 606/86 R |
| 2006/0166169 | A1* | 7/2006 | Dawood | A61C 8/0006 |
| | | | | 433/174 |
| 2010/0003638 | A1* | 1/2010 | Collins | A61K 6/818 |
| | | | | 433/174 |
| 2010/0318129 | A1* | 12/2010 | Seme | A61B 17/7001 |
| | | | | 606/279 |
| 2013/0209956 | A1 | 8/2013 | Sanders | |
| 2013/0274819 | A1* | 10/2013 | Horvath | A61F 2/28 |
| | | | | 606/86 R |
| 2014/0100612 | A1* | 4/2014 | Suddaby | A61B 17/7059 |
| | | | | 606/279 |
| 2014/0236234 | A1* | 8/2014 | Kroll | A61B 17/7016 |
| | | | | 606/279 |
| 2015/0250592 | A1* | 9/2015 | Horvath | A61F 2/2803 |
| | | | | 433/173 |

FOREIGN PATENT DOCUMENTS

| | | |
|---|---|---|
| JP | 2005523765 A | 8/2005 |
| KR | 101318863 B1 | 10/2013 |
| RU | 2306890 C2 | 9/2007 |
| RU | 72397 U1 | 4/2008 |
| RU | 2639792 C1 | 12/2017 |

OTHER PUBLICATIONS

Meyer et al., (2001) Mechanical tension in distraction osteogenesis regulates chondrocytic differentiation. Int J Oral Maxillofac Surg 30(6): 522-530.

Rachmiel et al., (2018) Two-stage reconstruction of the severely deficient alveolar ridge: bone graft followed by alveolar distraction osteogenesis. Int J Oral Maxillofac Surg 47(1): 117-124.

PCT Search Report for International Application No. PCT/IL2019/050722, dated Oct. 24, 2019, 4pp.

PCT Written Opinion for International Application No. PCT/IL2019/050722, dated Oct. 24, 2019, 6pp.

PCT Preliminary Report on Patentability for International Application No. PCT/IL2019/050722, dated Jan. 24, 2021, 7pp.

* cited by examiner

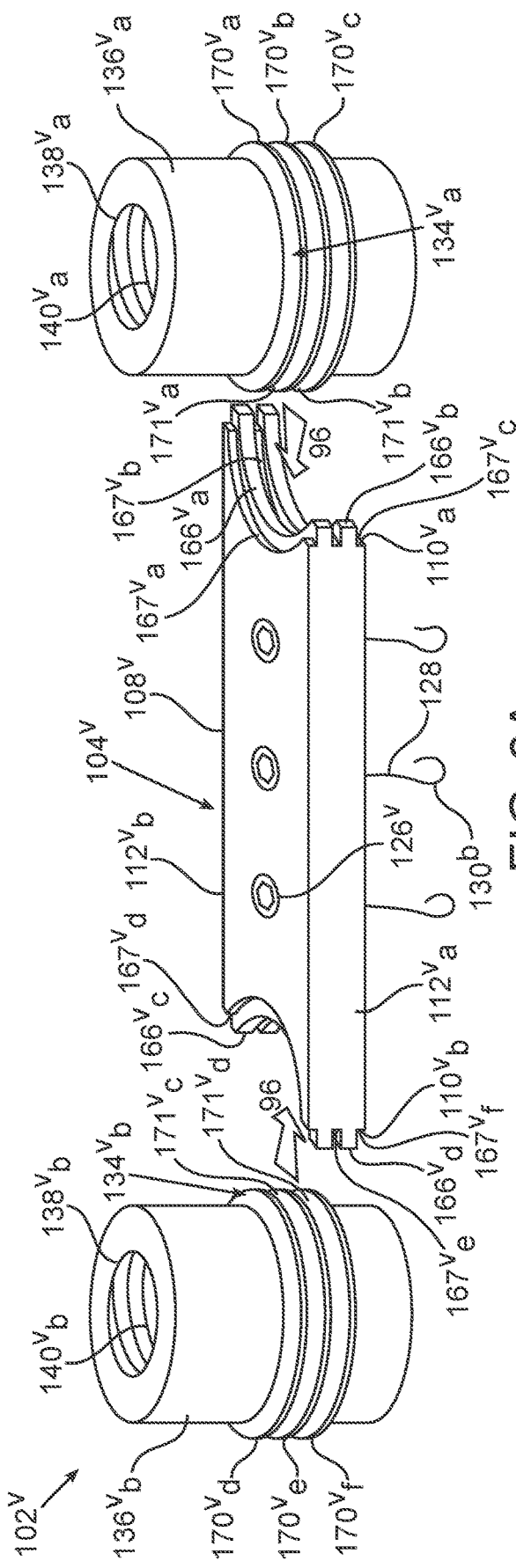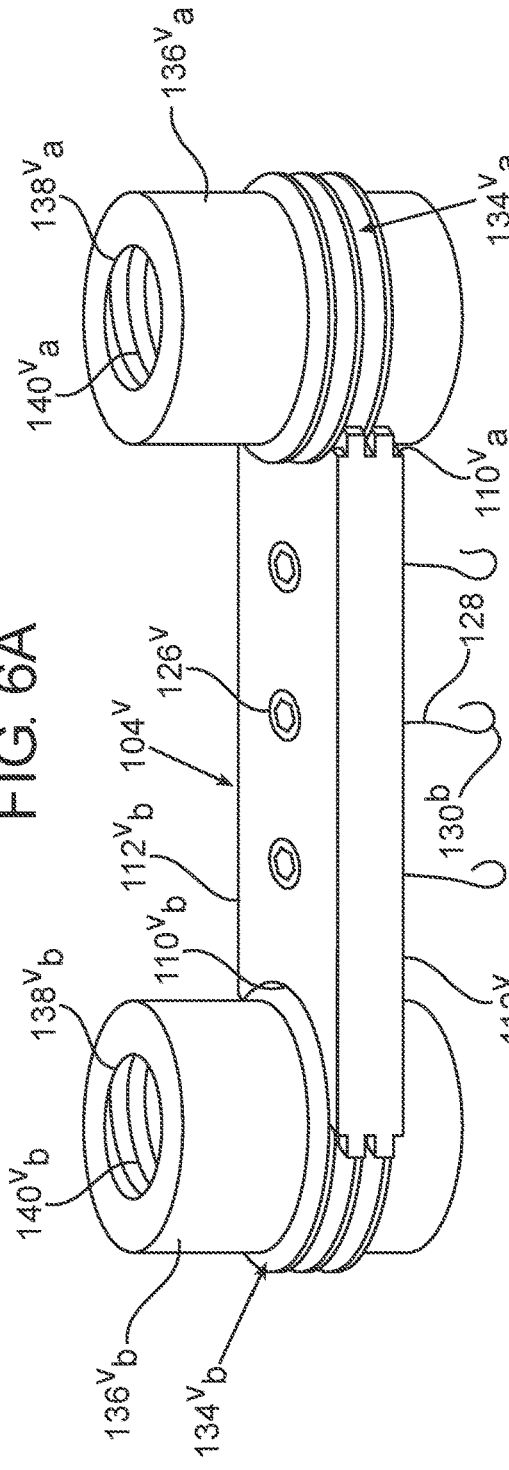

DEVICES, SYSTEMS AND METHODS FOR DISTRACTION OSTEOGENESIS

CROSS-REFERENCE TO RELATED APPLICATIONS

This application is a National Phase of PCT Patent Application No. PCT/IL2019/050722 having International filing date of Jun. 30, 2019, which claims the benefit of priority of U.S. Provisional Patent Application No. 62/823,012, filed Mar. 25, 2019 and Israel Patent Application No. 260367 filed Jul. 2, 2018, the contents of which are all incorporated herein by reference in their entirety.

FIELD OF THE INVENTION

The present invention relates to the field of devices and methods for distraction osteogenesis, and, more particularly, to distraction devices and distraction systems used in the treatment of mandibular or maxillary alveolar ridge atrophy, and to methods for utilizing a distraction device or a distraction system for bone lengthening.

BACKGROUND OF THE INVENTION

Mandibular or maxillary alveolar ridge atrophy is a known pathology, which can develop as a slow process of volume deterioration after tooth loss or acutely due to an inciting event as infection, cyst removal, traumatic tooth extraction, tumor resection or trauma. Adequate alveolar ridge volume is crucial for placement of dental implants. Placement of dental implants and the long-term prognosis of such primarily depend on the size of the dental implants, the ratio between them and the prosthesis attached to them and their spatial location relative to the intra jaw teeth and opposed jaw occlusion.

In some cases, the alveolar ridge atrophy can be overcome by placing short dental implants as a compromise, while in the majority of the cases a reconstructive phase needs to be applied prior to placement of dental implants. Several surgical procedures are known in the art, depending on the severity of alveolar ridge atrophy. Whereas mild atrophy can be resolved by guided tissue regeneration, intermediate and severe atrophy necessitates the use of bone grafts or bone lengthening. The severity of atrophy dictates the volume of the required bone graft, and consequently the grafting technique and materials. Since soft tissue coverage without tension of the entirety of the graft is crucial, causing limitations of the volume of the augmentation gain, vertical atrophy possesses the greatest challenge. As the latter increases, the challenge of soft tissue coverage becomes greater and less predictable. Thus, severe cases of alveolar ridge atrophy that cannot be predictively resolved by bone grafts, have been addressed in the last two decades by surgical technique of bone lengthening referred to as distraction osteogenesis.

Distraction osteogenesis is a technique of bone lengthening occurring by applying gradual controlled tension forces to an osteotomized bone segment. In contrast to traditional approaches, the soft tissue envelope is simultaneously expanded, thereby practically eliminating any limit to bone gain. This technique has become an important part of the reconstructive surgeon's armamentarium.

Most alveolar distractors comprise two attachment plates and a drive rod that connects them or pushes them apart. The purpose of the plates is to anchor the device to the basal bone and to an osteotomized bone segment. The purpose of the rod is to deliver tension forces to both bone segments, thereby distracting the mobile segment. Anchoring the device requires a minimal 5 mm vertical length of basal bone, and a similar length for the osteotomized segment, due to the dimensions of the attachment plates and the bone screws. When the procedure is performed in the posterior mandible, where the inferior alveolar nerve is located, care must be given to the position of the bone screws through the buccal cortex due to the proximity to the nerve. A peril of damaging the inferior alveolar nerve is unavoidable. Placing bone screws in the posterior maxilla can be similarly challenging due to thin bony wall of the maxillary sinus leading to defective device anchoring and stabilization. Due to these risks and limitations, distraction osteogenesis is rarely accepted by patients, although these patients frequently have no other reconstructive options. On the other hand, patients who fortunately have not experienced a previous extreme traumatic event such as resection of a benign tumor or trauma, lack the motivation to undergo a major surgical procedure and confront the relevant risks. Further reduction in motivation is also accountable to the fact that removal of the distraction appliance requires a second surgical procedure and accordingly more discomfort.

Alveolar distractors are composed of a single drive rod promoting movement according to a single vector. Bone gain is similar all along the distracted segment length. When atrophy is dissimilar in the anterior and posterior end of the distracted bone, often a compromise is required, or alternatively another surgical procedure is performed to remove excess bone in one side and add bone to a deficient side. Moreover, the vector set in the installation of the distractor cannot be changed or controlled after initiation of the distraction osteogenesis due to lack of accessibility and rigidity of the structure of the distractor. The mentioned above limitations, considerations and challenges raise the need for a different approach to bone gain via distraction osteogenesis. Major considerations as reduction of the hazard to the inferior alveolar nerve when anchoring the lower bone plate parallel or near the latter and the risk of inadequate stability when attempting to place a bone plate parallel to the maxillary sinus prompts the perception that the anchoring of the distraction device must be achieved elsewhere than this means. This led to the advance in the notion that anchoring the device can be achieved outside the surgical field. Anchoring the device to an adjacent existing dental implant or a tooth can offer these benefits and eliminating the hazards mentioned above.

Devices equipped with a single point distraction apply uneven stress/strain concentration on the osteomized segment, wherein a high stress concentration is applied to the osteomized segment at the attachment point to the pulling element, while lower stresses act on adjacent remote sections of the same segment. A publication by Meyer et al. (Plast. Reconstr. Surg. 1999 March; 103(3):800-7) presented experimental results showing that the strain magnitudes applied to the mandible during distraction osteogenesis can influence whether ossification occurs or unfavorable fibrous tissue is formed. Another publication by Meyer et al. (Int. J. Oral Maxillofac. Surg. 2001 December; 30(6):522-30) further demonstrated that such mechanical strains influence the phenotype of cell differentiation.

Applying several points of tension to the osteotomized bone intended for distraction can overcome the drawback of single point distraction, by applying a more even stress/strain distribution along the osteomized segment. The ability to control each tension points separately is of great importance, as it can offer differential bone gain along the surgical field. Accessibility to the part applying the distraction forces during the distraction phase can help control the distractor vector and adapting it the desired direction if the need for a change arises. Tension can be delivered by pushing the distracted bone away from its original bed or by pulling it away therefrom.

SUMMARY OF THE INVENTION

The following embodiments and aspects thereof are described and illustrated in conjunction with systems, devices and methods which are meant to be exemplary and illustrative, not limiting in scope. In various embodiments, one or more of the above-described problems have been reduced or eliminated, while other embodiments are directed to other advantages or improvements.

According to some embodiments, there are provided devices, systems and methods for performing distraction osteogenesis. A distraction device, disclosed in the present specification, can be attached to any dental structure adjacent to an alveolar ridge, such as a bone screw or even a native tooth, directly or via a dental abutment. A strings positioning member of the distraction device, which can be formed in some embodiments as a frame, extends over the region of an osteotomized bone segment of the alveolar ridge, from which at least one string extends towards and is attachable to at least one anchoring implant means, such as miniscrews or orthodontic screws, suitable for anchoring to osteotomized bone segments with limited vertical length.

The distraction device is provided with a plurality of string pull assemblies, configured to enable wrapping of each string attached to anchoring implant means during rotation thereof. The wrapping of each string results in a pulling force applied to the osteotomized bone segment via the corresponding anchoring implant means, thereby promoting formation of new bone tissue in the gap formed between the osteotomized bone segment and the remaining basal bone.

Advantageously, a procedure utilizing the disclosed distraction device reduces the hazard to sensitive regions, such as the inferior alveolar nerve, due to the disclosed distraction device ability to pull small-dimensioned anchoring implant means, such as orthodontic implants, instead of conventional larger bone plates. Moreover, the distraction method disclosed herein enables to perform distraction osteogenesis even in extremely complicated cases, where the amount bone in a region of an alveolar ridge is not suitable for distraction osteogenesis procedures by conventional distractors with bone plates. One such example is the posterior maxilla in which bone screws placed for anchoring a conventional distractor footplate cannot achieve reasonable stability due to thinness of the anterior maxillary sinus cavity.

A further advantage of the disclosed distraction device, having a plurality of string pull assemblies connected to a corresponding number of anchoring implant means, is that each string pull assembly can be operated independently, thereby applying a different pulling rate or a different distraction length to different regions of an osteotomized bone segment, to which a corresponding anchoring implant means is attached. Thus, applying several points of tension to the osteotomized bone intended for distraction can offer differential bone gain along the surgical region. Moreover, due to the fact the anchoring of the device is superficial and not submerged enables the operator the change the lateral vector of distraction during the distraction phase if the need for a change in the pre-set vector arises. This can be achieved, for example, by disconnecting the distraction device from the dental abutment, adjusting the lateral position of the frame of the distraction device, and reconnecting it back to the abutment.

A further advantage of the disclosed distraction device, is that it can be easily supported by dental supports known in the art, such as bone screws with or without dental abutments, or even attached to a native tooth. Removal of the distraction device does not require a surgery and can be easily performed, thus providing a simpler, shorter and more comfortable solution, compared with conventional distractors' removal requiring another surgical procedure and the related comorbidities.

According to one aspect, there is provided a distraction device for bone lengthening, the distraction device comprising a main body and a plurality of string pull assemblies.

The main body comprises at least one adaptor member having at least one connection platform, and a strings positioning member comprising a plurality of positioning features, spaced from each other along a longitudinal direction of the strings positioning member attachable to the at least one adaptor body, extending along a longitudinal direction substantially perpendicular to a vertical axis of the at least one adaptor member.

Each of the plurality of string pull assemblies comprises a string having a first string end and a second string end attached to a string engagement portion, and a movable element attached to the first string end, configured to move so as to promote displacement of the string engagement portion in a distal direction.

The strings positioning member extends along the longitudinal direction thereof, substantially perpendicular to a vertical axis of the at least one adaptor member, each of the plurality of string pull assemblies is attached to the main body, and each string of the plurality of strings is configured to extend through or along a corresponding, different, positioning feature.

According to some embodiments, at least one string pull assembly of the plurality of string pulley assemblies is attached to the strings positioning member.

According to some embodiments, at least one string pull assembly of the plurality of string pulley assemblies is attached to the at least one adaptor member.

According to some embodiments, the at least one movable element is formed as a rotatable shaft, and wherein the string pull assembly is rotateably attached to the main body According to some embodiments, the at least one string pull assembly further comprises a channel, and wherein the movable element is configured to axially move along at least one direction within the channel.

According to some embodiments, the channel comprises threading along at least a portion of its length, and wherein the movable element is formed as a screw threadedly engaged with the channel.

According to some embodiments, the channel comprises ratcheting teeth along at least a portion of its length, and wherein the movable element comprises at least one complementary tooth, configured to enable longitudinal one-directional movement of movable element along the channel.

According to some embodiments, the at least one string pull assembly further comprises a gear rigidly attached to the movable element, and the distraction device further comprises at least one pawl configured to engage with the gear, wherein the pawl is configured to allow free rotation of the string pull assembly in the one direction, while preventing its rotation in an opposite direction.

According to some embodiments, the at least one string pulley assembly further comprises a tooling interface rigidly attached to at least one end of the movable element, wherein rotation of the at least one tooling interface is one direction results in rotation of the movable element in the same direction.

According to some embodiments, the strings positioning member further comprises a first sidewall and a second sidewall, and wherein the at least one tooling interface is exposed through at least one opening in the first sidewall or the second sidewall.

According to some embodiments, the strings positioning member further comprises at least one positioning member chamber, bordered between the first sidewall and the second sidewall, and configured to house the at least one string pull assembly.

According to some embodiments, the strings positioning member further comprises a front panel, and wherein the at least one tooling interface is exposed through at least one opening in the front panel.

According to some embodiments, the strings positioning member further comprises a distal panel, and the at least one tooling interface is exposed through at least one opening in the in the distal panel.

According to some embodiments, the strings positioning member further comprises at least one support rod.

According to some embodiments, the at least one positioning feature is formed as an aperture, configured to allow passage and free movement of the string there through.

According to some embodiments, the at least one positioning feature is formed as a contact point between the string and the support rod.

According to some embodiments, the at least one connection platform comprises a mounting bore.

According to some embodiments, the mounting bore comprises a bore screw thread.

According to some embodiments, the mounting bore comprises an anti-rotational internal surface.

According to some embodiments, the adaptor member further comprises a stationary ring portion and a dynamic ring portion hinged thereto, wherein the dynamic ring portion comprises a tightening mechanism configured to form the mounting bore by detachably attaching an end of dynamic ring portion to either the stationary ring portion or the strings positioning member.

According to some embodiments, the adaptor member further comprises a tightening mechanism configured to adjust the diameter of central bore.

According to some embodiments, the strings positioning member is detachably attachable to the at least one adaptor member via a quick snap attachment.

According to some embodiments, the strings positioning member further comprises a positioning member's attachment means, and wherein the at least one adaptor body further comprises an adaptor attachment means, configured to engage with the strings positioning member attachment means.

According to some embodiments, the at least one adaptor member comprises two adaptor members connected to each other via an adaptor attachment means, the adaptor attachment means comprising an adaptor attachment socket formed to receive the strings positioning member therein.

According to some embodiments, the at least one component of the distraction device is manufactured via the use of a CAD-CAM software, according to a design specific to a patient.

According to some embodiments, there is provided distraction system comprising the distraction device according to any of the aforementioned embodiments, and an abutment. The abutment comprises an abutment distal portion, configured to engage with the at least one connection platform of the at least one adaptor member, an abutment proximal portion, and an abutment mid-portion, fluidly connected to the abutment distal portion and to the abutment proximal portion. The largest cross-sectional diameter of the abutment mid-portion is larger than any of the largest cross-sectional diameter of the abutment distal portion and the largest cross-sectional diameter of the abutment proximal portion.

According to some embodiments, the abutment proximal portion comprises a polyhedral-shaped structure.

According to some embodiments, the abutment distal portion comprises an abutment distal portion screw thread.

According to some embodiments, the abutment distal portion comprises a polyhedral-shaped structure.

According to some embodiments, the abutment distal portion comprises a plurality of regularly spaced vertical notches that create a corresponding plurality of wings, wherein the plurality of wings are provided with intrinsic flexibility. Further, each wing comprises a wing inner surface and a wing outer surface, wherein the wing inner surfaces together with the notches define an abutment distal receiving opening.

According to some embodiments, the distraction system further comprises a plug having a plug distal portion, configured to be inserted through the abutment distal receiving opening into the abutment, thereby flexing the wings radially outwards.

According to some embodiments, the plug distal portion is provided with a frustoconical profile According to some embodiments, the plug further comprises a plug base provided with a threading.

According to some embodiments, the distraction system further comprises at least one miniscrew, configured for engagement with the at least one string engagement portion.

According to some embodiments, the miniscrew further comprises a receiving area.

According to some embodiments, the receiving area of the miniscrew is formed as a through-hole.

According to some embodiments, the receiving area of the miniscrew is formed as a recess having at least one distal vertical extension.

According to some embodiments, the receiving area of the miniscrew comprises an opening with a latch.

According to some embodiments, the distraction system further comprises a bone screw, configured to receive and securely engage with the abutment.

According to yet another aspect of the invention, there is provided a method of using a distraction device, comprising the steps of:
(i) providing the distraction device according to any one of the aforementioned embodiments,
(ii) connecting the distraction device to a mount,
(iii) attaching the plurality of string engagement portions to the plurality of miniscrews, wherein each string engagement portion is attached to a single mini screw,
(iv) stretching the plurality of strings between the plurality of movable elements and the plurality of miniscrews, by moving the plurality of movable element,
(v) displacing at least one of the plurality of miniscrew in the distal direction, by further moving the respective movable attached thereto, and (vi) repeating the step of displacing at least one miniscrew in the distal direction periodically, for all miniscrews.

According to some embodiments, moving any of the plurality of movable element comprises rotating the movable element.

According to some embodiments, moving any of the plurality of movable element comprises axially displacing the movable element.

According to some embodiments, the mount is a bone screw.

According to some embodiments, the mount is an abutment attached to a bone screw.

According to some embodiments, each string pull assembly is operated independently, thereby applying a different pulling rate to different miniscrews.

According to yet another aspect of the invention, there is provided a distraction assembly comprising the distraction device according to any one of the aforementioned embodiments, and a clamp. The adaptor member of the distraction device further comprises a plurality of axial extensions, configured to bend radially inwards upon application of an external force along their circumference.

The clamp comprises a band and a worm gear mechanism, the worm gear mechanisms configured to cause contraction or expansion of the clamp and keep the clamp at the adjusted position. The clamp is configured to engage with the distraction device by placement thereof over the exterior of the adaptor member, and is further configured to exert force on the contractible adaptor member, sufficient bend the plurality of axial extensions radially inwards.

According to some embodiments, the distraction device further comprises an arcuate slot disposed between the strings positioning member and the adaptor member, dimensioned to accommodate at least a portion of the band, and a worm recess adjacent the arcuate slot, configured to accommodate the worm gear mechanism.

According to some embodiments, the band further comprises at least one retaining slot, and wherein the adaptor member comprises at least one retaining protrusion extending radially outwards therefrom, and configured to be positioned within the respective at least one retaining slot.

According to some embodiments, the distraction assembly further comprises an abutment, which comprises an abutment distal portion configured to engage with the at least one connection platform of the at least one adaptor member, an abutment proximal portion, and an abutment mid-portion, fluidly connected to the abutment distal portion and to the abutment proximal portion.

According to yet another aspect of the invention, there is provided a dental abutment comprising an abutment distal portion, an abutment proximal portion, and an abutment mid-portion, fluidly connected to the abutment distal portion and to the abutment proximal portion.

According to some embodiments, the abutment distal portion comprises a plurality of regularly spaced vertical notches that create a corresponding plurality of wings, wherein the plurality of wings are provided with intrinsic flexibility. Further, each wing comprises a wing inner surface and a wing outer surface, wherein the wing inner surfaces together with the notches define an abutment distal receiving opening.

According to some embodiments, the distraction system further comprises a plug having a plug distal portion, configured to be inserted through the abutment distal receiving opening into the abutment, thereby flexing the wings radially outwards.

According to some embodiments, the plug distal portion is provided with a frustoconical profile According to some embodiments, the plug further comprises a plug base provided with a threading.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 6A constitutes a view in perspective of a strings positioning member detached from two adaptor bodies, according to some embodiments.

FIG. 6B constitutes a view in perspective of the strings positioning member attached to both adaptor bodies of FIG. 6A.

DETAILED DESCRIPTION OF SOME EMBODIMENTS

Figure 1A:
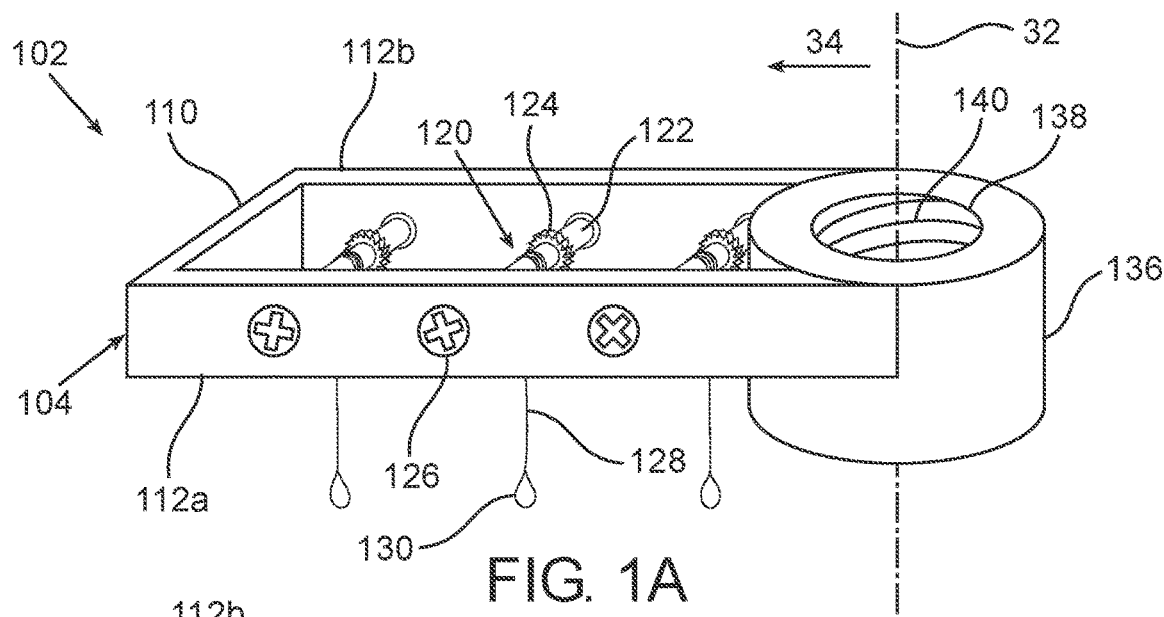
FIG. 1A constitutes a view in perspective of a distraction device without a distal panel, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. Components having the same reference number followed by different lowercase letters may be collectively referred to by the reference number alone. If a particular set of components is being discussed, a reference number without a following lowercase letter may be used to refer to the corresponding component in the set being discussed.

Figure 8A:
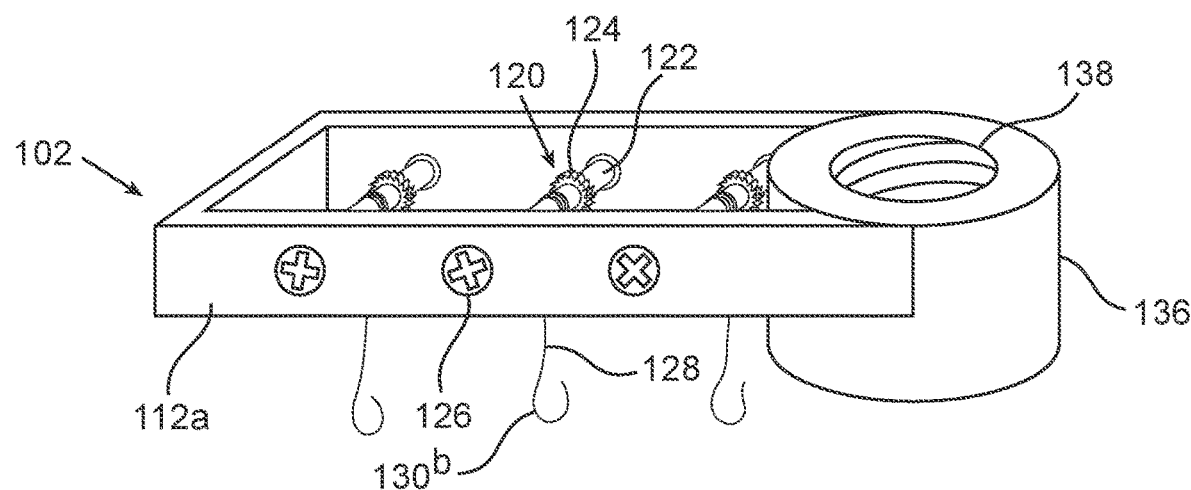
FIG. 8A constitutes a view in perspective of a distraction device with tooling interfaces in the form of a Phillips sockets, according to some embodiments.
Figure 8B:
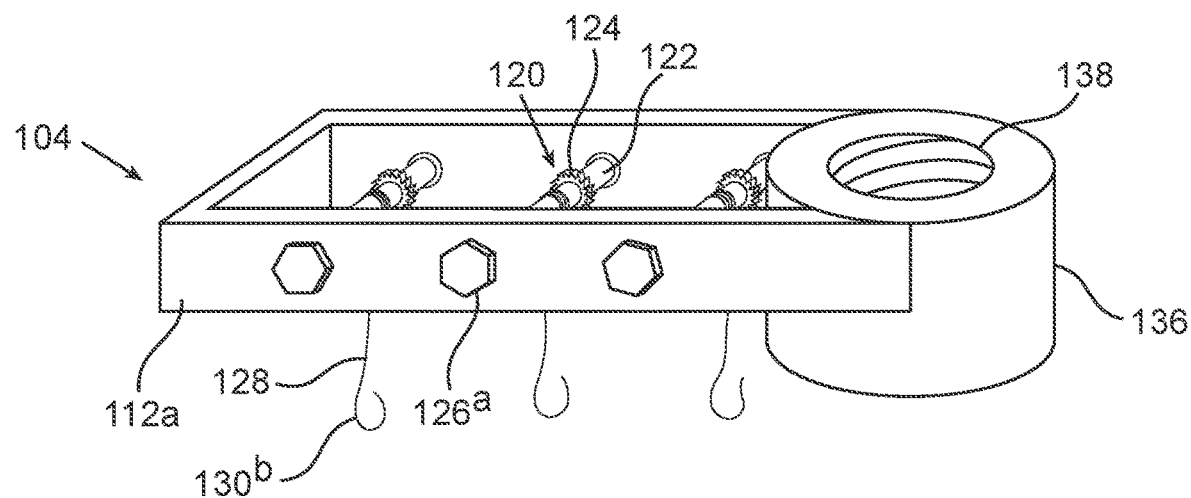
FIG. 8B constitutes a view in perspective of a distraction device with tooling interfaces in the form of hex or Allen screw-heads, according to some embodiments.
Figure 8C:
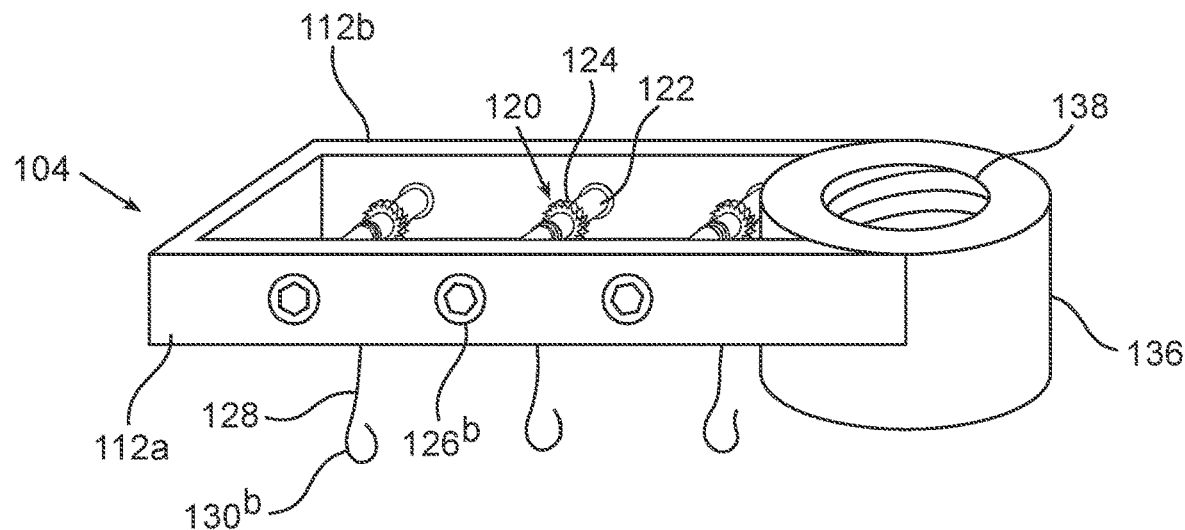
FIG. 8C constitutes a view in perspective of a distraction device with tooling interfaces in the form of hex or Allen sockets, according to some embodiments.
Figure 9A:
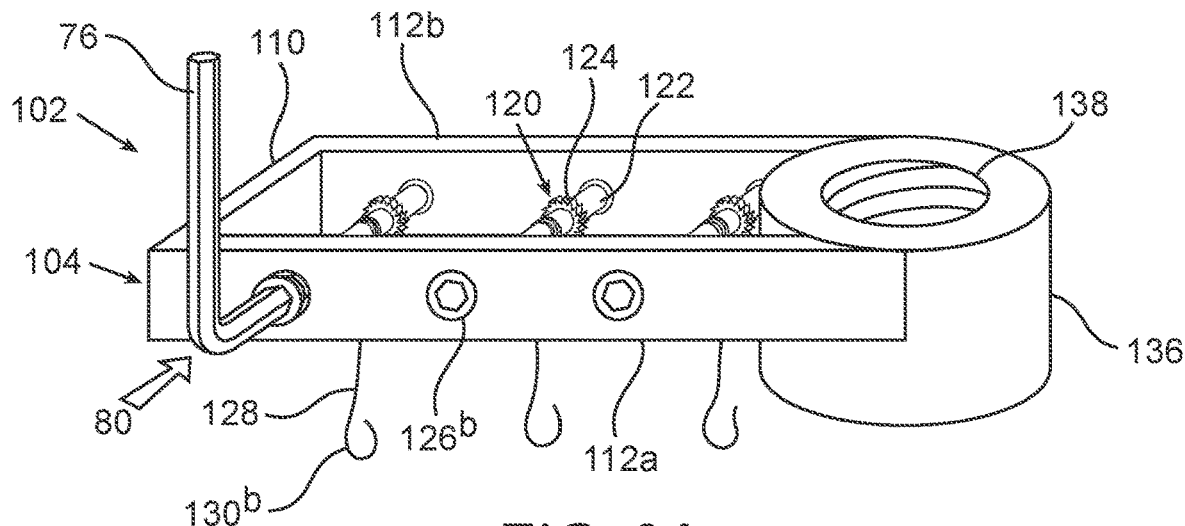
FIG. 9A constitutes a view in perspective of a distraction device with an Allen key-type rotation tool engaged with a tooling interface, according to some embodiments.
Figure 9B:
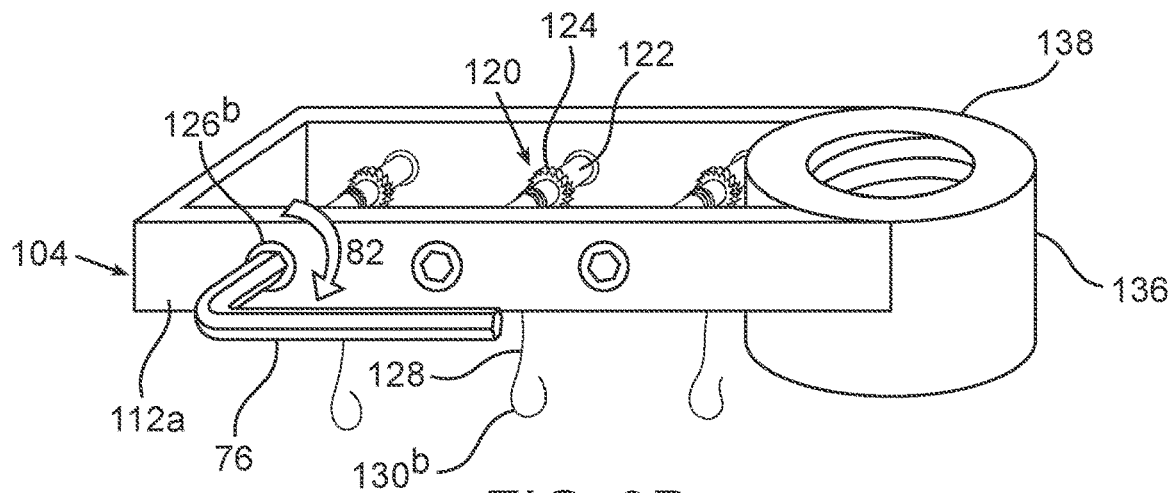
FIG. 9B constitutes a view in perspective of a distraction device with the Allen key of FIG. 9A rotated clockwise, according to some embodiments.
Figure 9C:
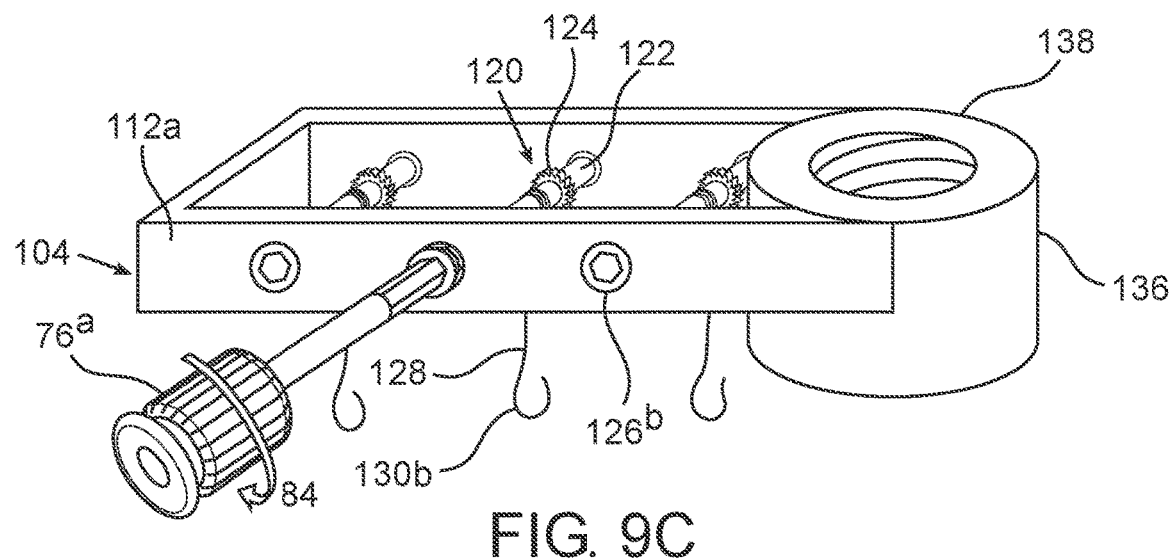
FIG. 9C constitutes a view in perspective of a distraction device with a rotation tool engaged with a tooling interface, according to some embodiments.
Figure 10A:
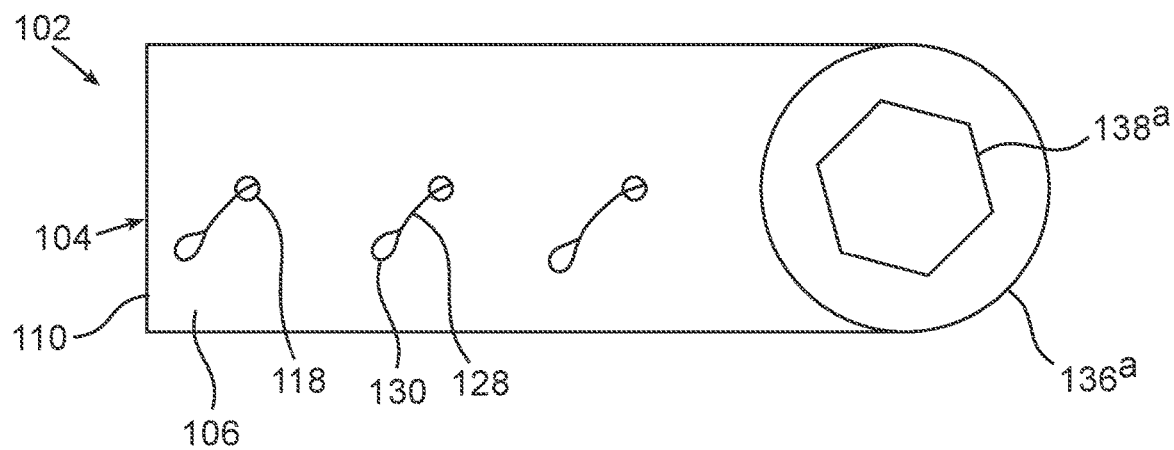
FIG. 10A constitutes a bottom view of a distraction device having a hexagonal-shaped mounting socket, according to some embodiments.
Figure 10B:
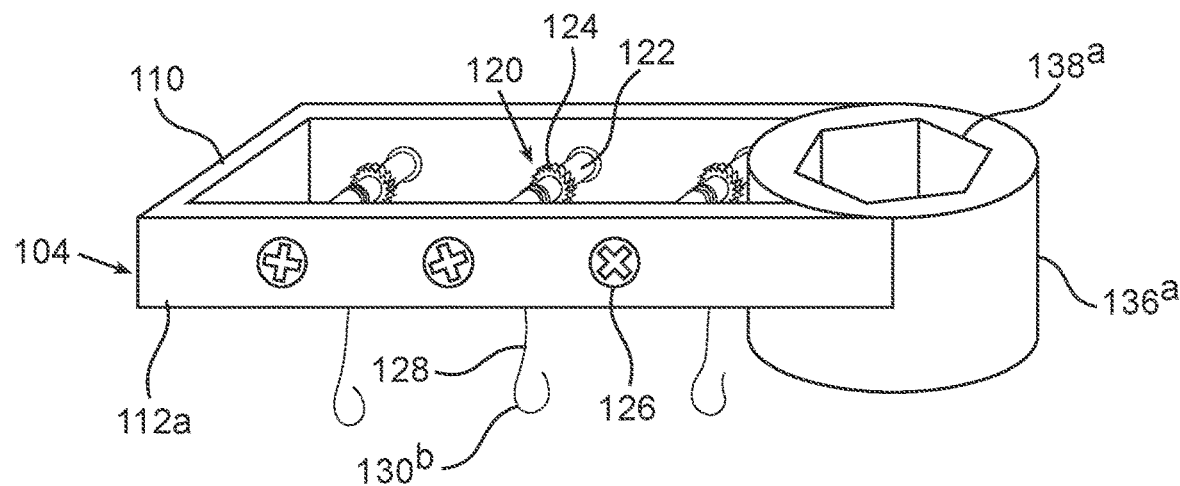
FIG. 10B constitutes a view in perspective of a distraction device having a hexagonal-shaped mounting socket, according to some embodiments.
Figure 10C:
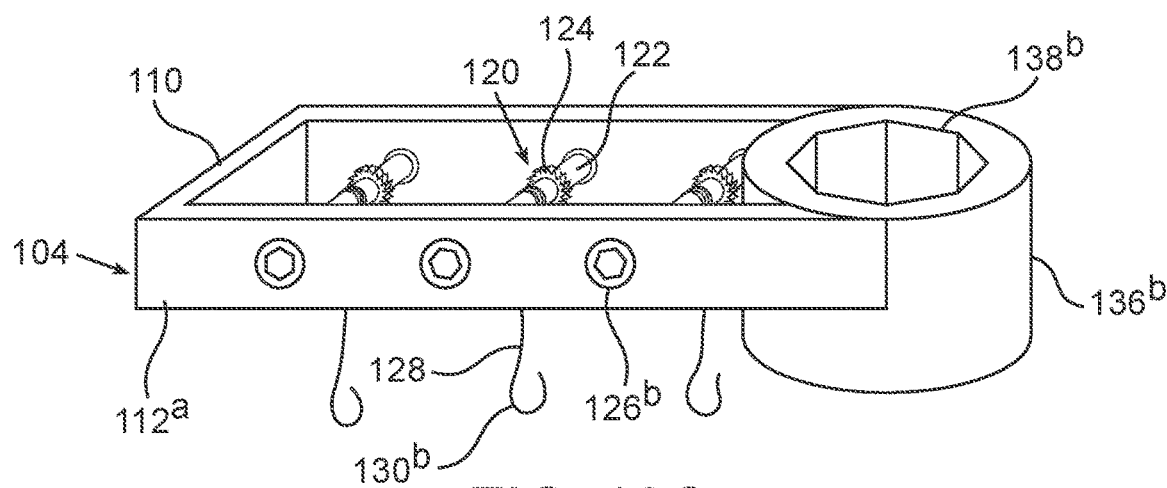
FIG. 10C constitutes a view in perspective of a distraction device having an octagonal-shaped mounting socket, according to some embodiments.

Reference is now made to FIGS. 1A-6C. FIGS. 1A and 1B constitute a view in perspective and a top view, respectively, of a distraction device 100 for bone lengthening, presented without a distal panel, according to some embodiments. FIGS. 2A, 2B and 2C constitute a view in perspective, a top view and a bottom view, respectively, of the distraction device 100, according to some embodiments. FIGS. 3A and 3B constitute a cross-sectional side view of two different embodiments of distraction device 100. FIGS. 8A, 8B and 8C constitute a view in perspective of the distraction device 100 with tooling interfaces in the form of Phillips sockets, hex or Allen screw-head, and hex or Allen sockets, respectively. FIGS. 9A, 9B and 9C constitute a view in perspective of different embodiments of rotation tools engaged with a tooling interface. FIGS. 10A and 10B constitute a bottom view and a view in perspective, respectively, of a distraction device 100 having a hexagonal-shaped mounting socket. FIG. 10C constitutes a view in perspective of a distraction device 100 having an octagonal-shaped mounting socket.

Distraction device 100 comprises a main body 102 and a plurality of string pull assemblies 120, each of the string pull assemblies 120 attached to at least one member of the main body 102, wherein each of the plurality of string pull assemblies 120 is configured to be independently operated to pull a string 128 attached thereto. According to some embodiments, main body 120 comprises at least one adaptor member 136 and a strings positioning member 104, such that each of the plurality of string pull assemblies 120 is attached to at least one of: adaptor member 136 or strings positioning member 104.

The term "string pull assembly", as used herein, refers to any one of the plurality of string pull assemblies.

According to some embodiments, at least one string pull assembly 120 is attached both to at least one adaptor member 136 and to strings positioning member 104, for example such that one end of the string pull assembly 120 is attached to at least one adaptor member 136, and the opposite end of the string pull assembly 120 is attached to strings positioning member 104.

According to some embodiments, all of the string pull assemblies 120 are attached to at least one adaptor member 136. According to some embodiments, all of the string pull assemblies 120 are attached to strings positioning member 104. According to some embodiments, some of the string pull assemblies 120 are attached to at least one adaptor member 136, while the remainder to string pull assemblies 120 are attached to strings positioning member 104.

Main body 102 is configured to connect with a mount via at least one adaptor member 136. A mount can include any structure attached to or configured for attachment to a jaw, either directly or indirectly, such as an abutment, a dental crown, a dental screw, a dental bridge, a denture, a native tooth and the like. Axis 32 is a longitudinal axis of such a mount, extending between a proximal end and a distal end thereof.

Strings positioning member 104 extends from adaptor member 136 along a longitudinal direction 34 (see FIG. 1A), substantially perpendicular to axis 32. Strings positioning member 104 is configured to promote longitudinal distribution of each string 128 of the plurality of string pull assemblies 120, such that each string 128 of the plurality of string pull assemblies 120 extends proximally (i.e. towards the jaw of a patient, when in use) through the strings positioning member 104 from a different position along its longitudinal direction 34.

According to some embodiments, strings positioning member 104 comprises a plurality of positioning features 118, spaced from each other along longitudinal direction 34, wherein a string 128 of each string pull assemblies 120 is configured to extend through or along a corresponding, different, positioning feature 118.

The term 'substantially perpendicular to axis', as used herein, refers to a direction that can be angled a range of 60°-120° relative to the axis.

According to some embodiments, strings positioning member 104 and adaptor member 136 are integrally formed. According to some embodiments, strings positioning member 104 and adaptor member 136 are attached to each other. According to some embodiments, strings positioning member 104 and adaptor member 136 are fixedly attached to each other. According to some embodiments, strings positioning member 104 and adaptor member 136 are removably attached to each other.

According to some embodiments, strings positioning member 104 is formed as a frame having a first sidewall 112a and a second sidewall 112b (see FIGS. 1A-3B). According to some embodiments, strings positioning member 104 is formed as a plate (embodiment not shown). According to some embodiments, strings positioning member 104 further comprises a front panel 110. According to some embodiments, front panel 110 and sidewalls 112 are integrally formed.

String pull assembly 120 comprises a movable element 122 attached to a string 128 having a string engagement portion 130 at a proximal end thereof, wherein the moving element 122 is configured to move so as to promote displacement of the second string end, along with the string engagement portion 130, in a distal direction, i.e. towards the strings positioning member 104.

According to some embodiments, string pull assembly 120 is a rotatable string pull assembly 120, and the moving element 122 is a rotatable shaft, wherein at least one tooling interface 126 is located at an end of the moving element 122 formed as a shaft, and string 128 is connected at a first string end (not numbered) to the moving element 122 formed as a shaft. In such embodiments, string 128 is configured to wrap over the moving element 122 formed as a shaft during rotational movement of the moving element 122 formed as a shaft in one direction, and to unwrap during rotation movement of the moving element 122 formed as a in an opposite direction.

According to some embodiments, rotatable string pull assemblies 120 are rotateably attached to main body 102. According to some embodiments, string pull assemblies 120 formed as rotatable string pull assemblies, are rotateably attached to strings positioning member 104. According to some embodiments, as illustrated in FIGS. 1A-2C, string pull assemblies 120 formed as rotatable string pull assemblies, are rotateably attached to at least one sidewall 112.

According to some embodiments, string pull assembly 120 formed as a rotatable string pull assembly, is rotateably connected to at least one sidewall 112, such that tooling interface 126 is exposed for engagement with a tooling device 76 (see FIGS. 9A-C) through the at least one sidewall 112. According to some embodiments, string pull assembly 120 formed as a rotatable string pull assembly, includes two tooling interfaces 126, located at each end thereof such that each one of tooling interfaces 126 is exposed for engagement with a tooling device 76 through each one of first sidewall 112a and second sidewall 112b.

According to some embodiments, string pull assembly 120 formed as a rotatable string pull assembly, comprises a string 128 having a first string end and a second string end (not numbered). String 128 is affixed at first string end to movable element 122, such the movement of movable element 122 promotes displacement of the opposite end of string 128 distally, i.e. towards the strung pull assembly 120. According to some embodiments, string 128 is affixed at first string end to a movable element 122 formed as a shaft, such that 122 formed as a shaft in one direction causes wrapping of string 128 around movable element 122 formed as a shaft in a manner that shortens the length of the unwrapped portion of string 128.

According to some embodiments, string 128 comprises a non-extensible material. According to some embodiments, string 128 comprises any string, cord, thread, wire or cable which is resilient along its length.

According to some embodiments, string 128 comprises a string engagement portion 130. According to some embodiments, string engagement portion 130 comprises a loop (see FIG. 1A). According to some embodiments, string engagement portion 130 comprises a hook (see FIG. 3A). According to some embodiments, string engagement portion 130 is formed as a free end of string 128 (see FIGS. 8A-9C), which can be tied onto itself so as to form, for example, a loop (such as the loop depicted in FIG. 1A).

Figure 2A:
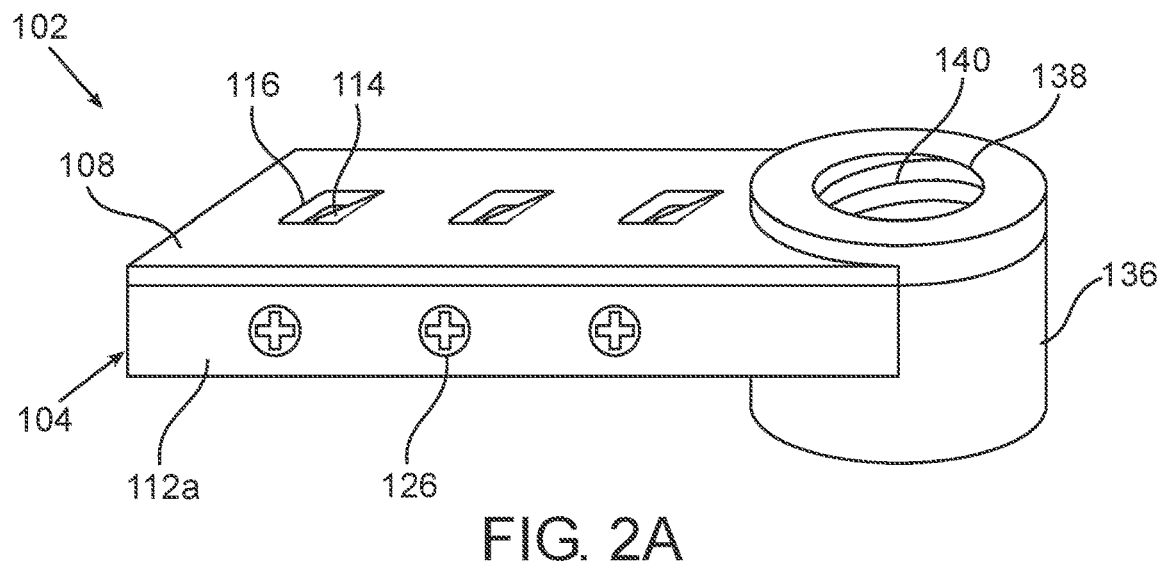
FIG. 2A constitutes a view in perspective of a distraction device, according to some embodiments.
Figure 2B:
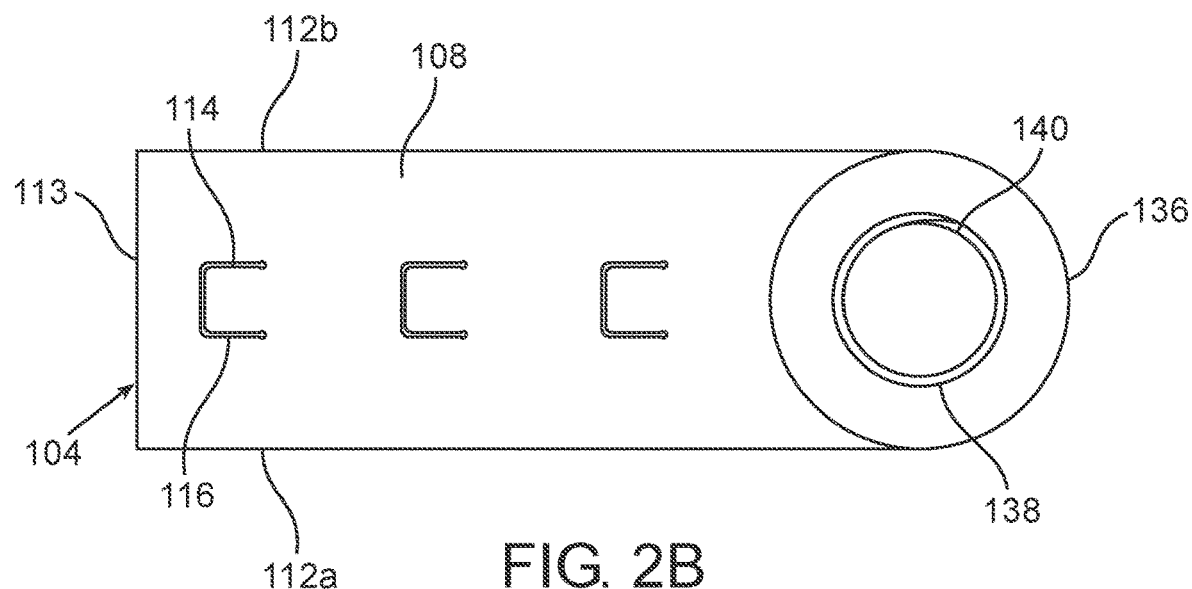
FIG. 2B constitutes a top view of a distraction device, according to some embodiments.
Figure 2C:
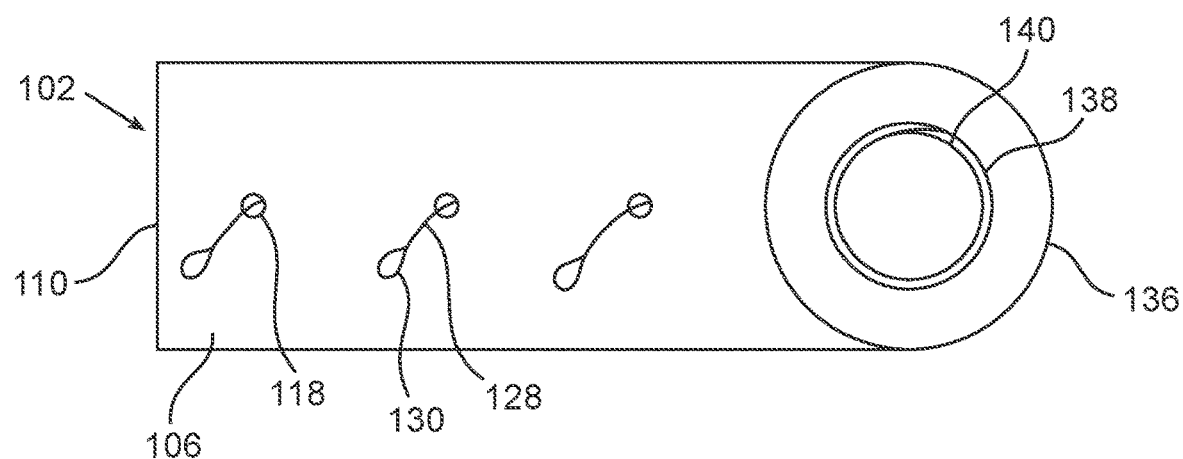
FIG. 2C constitutes a bottom view of a distraction device, according to some embodiments.
Figure 3A:
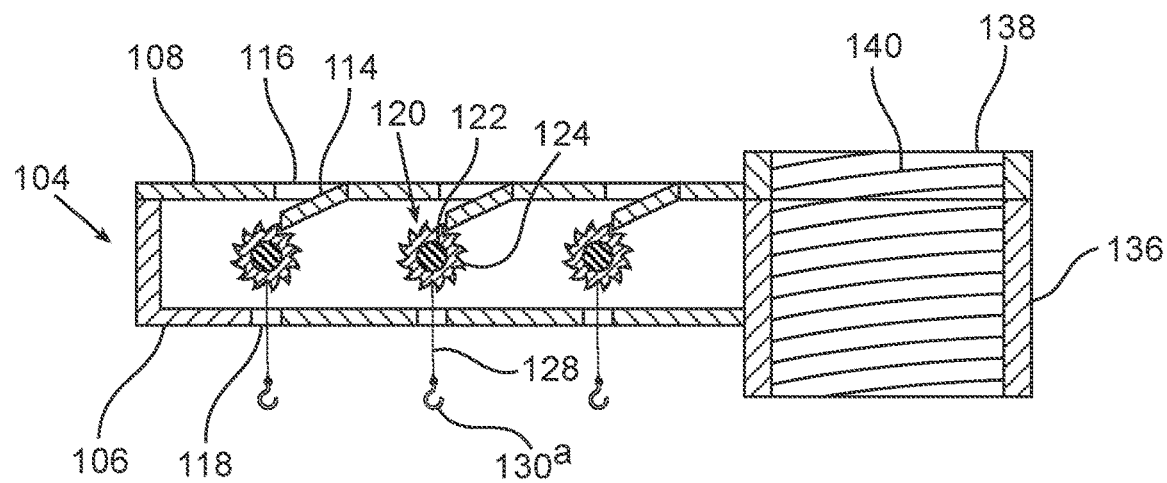
FIG. 3A constitutes a cross-sectional side view of a distraction device, according to some embodiments.
Figure 3B:
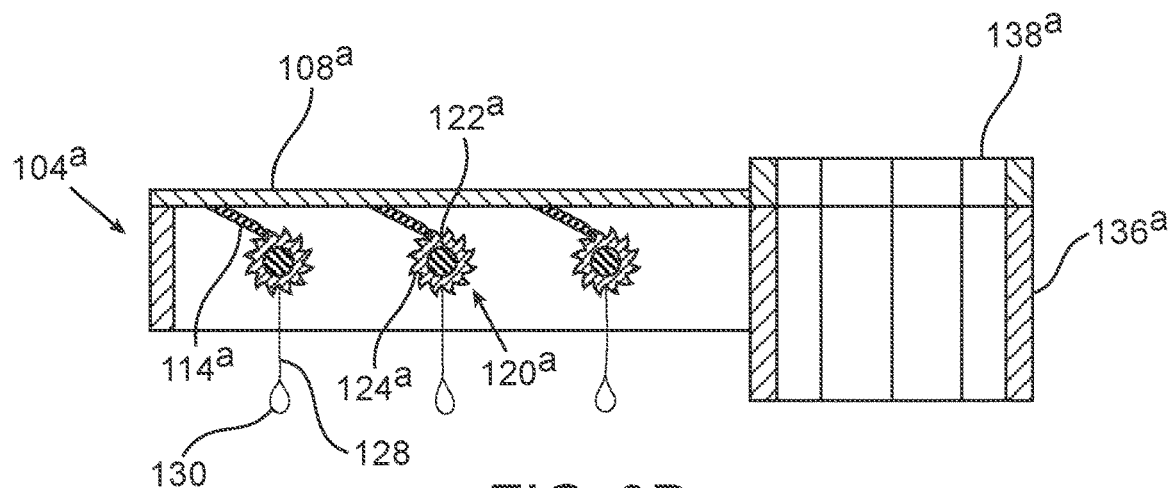
FIG. 3B constitutes a cross-sectional view of a distraction device devoid of a proximal panel, according to some embodiments.

According to some embodiments, string positioning member 104 comprises a proximal panel 106 (see FIG. 2C). According to some embodiments, proximal panel 106 is removably attached to sidewalls 112. According to some embodiments, proximal panel 106 and sidewalls 112 are integrally formed. According to some embodiments, as illustrated in FIG. 3B, string positioning member 104 is devoid of proximal panel 106.

Within the context of this application the term "proximal" generally refers to the side or end of any device or a component of a device, which is closer to a jaw-bone when in use. More particularly, a proximal end of distraction device 100 is the end which is closer to an alveolar ridge 52.

Within the context of this application the term "distal" generally refers to the side or end of any device or a component of a device, which is opposite the "proximal end", and is farther from a jaw-bone when in use.

According to some embodiments, proximal panel 106 comprises at least one positioning feature 118 formed as an aperture. According to some embodiments, proximal panel 106 comprises at least one positioning feature 118 formed as an aperture, aligned with the region of attachment of string 128 to movable element 122, configured to allow passage and free movement of string 128 there through. According to some embodiments, location of the at least one positioning feature 118 formed as an aperture, relative to the at least one movable element 122, is such that string 128 passes there through without contacting any edge of positioning feature 118 formed as an aperture.

According to some embodiments, at least one positioning feature 118 comprises any one of: an aperture, an opening, a window, a slot, a channel and a duct.

According to some embodiments, at least one positioning feature 118 is formed by the contact point between the at least one movable element 122 and the at least one string 128 attached thereto or abutting it, such that the position of this contact point defines the position along direction 34 of the string positioning member 104, from which the string 128 extends in the proximal direction (i.e. towards the alveolar ridge 52) when in use.

According to some embodiments, the at least one movable element 122 comprises, at least one end thereof, a tooling interface 126. According to some embodiments, the at least one movable element 122 formed as a shaft comprises two tooling interfaces 126, one at each end of shaft 122. Each tooling interface 126 is rigidly attached to the at least one end of movable element 122 formed as a shaft, such that rotation of tooling interface 126 in one direction, results in rotation of the movable element 122 formed as a shaft in the same direction. According to some embodiments, the at least one movable element 122 and the at least one tooling interface 126 are integrally formed. According to some embodiments, tooling interface 126 is exposed through an opening (not numbered) of at least one sidewall 112.

According to some embodiments, the at least one string pull assembly 120 formed as a rotatable string pull assembly, comprises gear 124 rigidly mounted on movable element 122 formed as a shaft, between sidewalls 112a and 112b, such that rotation of movable element 122 results in rotation of gear 124 in the same direction. According to some embodiments, distraction device 100 further comprises at least one pawl 114, configured to engage with the gear 124 of the at least one string pull assembly 120. According to some embodiments, gear 124 comprises a ratchet gear, whereby pawl 114 is configured to allow rotation of gear 124 in one direction, while preventing it from rotating in the opposite, or backwards, direction. According to some embodiments, the interface between gear 124 and pawl 114 is configured to allow free rotation of string pull assembly 120 formed as a rotatable string pull assembly, in a direction that wraps or loops string 128 around movable element 122 formed as a shaft, while preventing such rotation in the opposite direction, thereby preventing the option of unwrapping string 128 from movable element 122. Direction of free rotation can be counter clockwise in some embodiments (see FIG. 3A), or clockwise in other embodiments (see FIG. 3B).

Figure 1B:
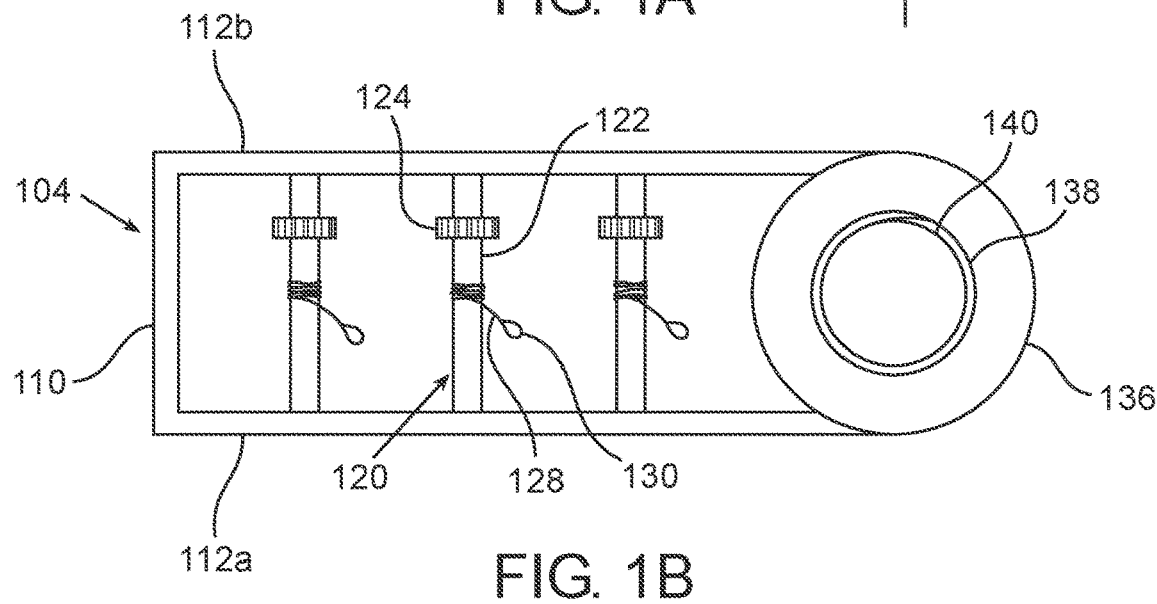
FIG. 1B constitutes a top view in perspective of the distraction device of FIG. 1B.

According to some embodiments, string positioning member 104 comprises a distal panel 108 (see FIGS. 2A-B, not shown in FIGS. 1A-B in order to expose components housed within string positioning member 104). According to some embodiments, distal panel 108 is removably attached to sidewalls 112. According to some embodiments, distal panel 108 and sidewalls 112 are integrally formed.

According to some embodiments, distal panel 108 comprises the at least one pawl 114, attached to distal panel 108 on a first pawl end (not numbered), and is free to engage gear 124 on a second pawl end (not numbered). According to some embodiments, as illustrated in FIGS. 2A-B and 3A, distal panel 108 comprises at least one panel window 116, overlaying the position of gear 124, such that the first pawl end is attached to an edge of panel window 116. According to some embodiments, as illustrated in FIG. 3B, pawl 114$^a$ is attached to a distal panel 108 devoid of panel windows 116.

While FIGS. 3A and 3B depict embodiments in which pawl 114 or 114$^a$, respectively, is attached at one end to distal panel 108. It will be understood by those skilled in the art that as long the second pawl end is engaged with the corresponding gear 124, the first pawl end can be attached, directly or indirectly, to any other portion of distraction device 100, such as, but not limited to, proximal panel 106 (see FIG. 22C), any one of side panels 112, front panel 114, other portions of the main string positioning member 104 and at least one adaptor member 136.

According to some embodiments, pawl 114 is either formed as a spring or attached by a spring (not shown) to either distal panel 108 or other portions of distraction device 100, such that pawl second edge is spring-biased against gear 124.

While FIGS. 3A and 3B depict embodiments of specific ratcheting mechanisms, it will be understood by those skilled in the art that other mechanisms can be implemented to limit rotation of movable element 122 formed as a shaft to one direction, or at least control such rotational movement in each direction separately. Such mechanisms may include, but are not limited to, a double ratchet mechanism, a two-way ratchet mechanism, a friction ratchet mechanism, a one-way clutch, an anti-reverse clutch, and a revolution counter.

At least one adaptor member 136 comprises at least one connection platform configured as an internal, external and/or any combination thereof, configured to connect with a mount, which is directly or indirectly secured to a jaw bone. A mount may include an abutment, a dental crown, a dental screw, a dental bridge, a denture, a native tooth and the like. According to some embodiments, at least one adaptor member 136 is formed as an abutment, a dental crown or a dental bridge, configured to connect with a mount in the form of a denture, a native tooth, a bone screw and the like.

According to some embodiments, at least one adaptor member 136 comprises mounting bore 138 serving as a connection platform. According to some embodiment, mounting bore 138 comprises bore screw thread 140 along its length (see FIGS. 1A-3A) or a portion thereof, provided for integrating with an external component having a matching screw thread.

According to some embodiment, adaptor member 136$^a$ comprises mounting bore 138$^a$ (see FIG. 3B), having an anti-rotational internal surface along its length. According to some embodiments, the anti-rotational internal surface is formed with a hexagonal cross-section along the length of mounting bore 138$^a$ (see FIGS. 10A-10B). According to some embodiments, the anti-rotational internal surface is formed with an octagonal cross-section along the length of mounting bore 138$^b$ (see FIG. 10C). According to some embodiment, the anti-rotational internal surface comprises any non-circular cross-section, such as a convex or concave (e.g. star-shaped) polygon, ellipse or other oval, and/or crescent shape.

According to some embodiments, string positioning member 104 is attached to at least one adaptor member 136. The term "string positioning member attached to at least one adaptor body", as used herein, refers to either string positioning member 104 rigidly attached to at least one adaptor member 136, or to string positioning member 104 detachably attachable to at least one adaptor member 136. According to some embodiments, string positioning member 104 is affixed to at least one adaptor member 136. According to some embodiments, string positioning member 104 and at least one adaptor member 136 are integrally formed. According to some embodiments, string positioning member 104 is detachably attached to at least one adaptor body 136.

According to some embodiments, string positioning member 104 comprises frame attachment means, configured to support attachment to at least one adaptor member 136. According to some embodiments, at least one adaptor member 136 comprises adaptor attachment means 134, configured to support attachment to string positioning member 104. According to some embodiments, detachable attachment of frame 104 to at least one adaptor member 136 is supported via engagement between frame attachment means and adaptor attachment means 134.

According to some embodiments, distraction device 100 comprises a plurality of adaptor members 136. According to some embodiments, distraction device 100 comprises two adaptor members 136, each one configured to be detachably attached to an opposite end of string positioning member 104.

According to some embodiments, adaptor attachment means 134 is a quick-snap type of attachment, defined as an attachment enabling quick attachment of the string positioning member 104 to at least one adaptor member 136 by application of manual push/pull force, and quick removal of string positioning member 104 from at least one adaptor member 136 by application of manual push/pull force. According to some embodiments, adaptor attachment means 134 is devoid of screws, thereby providing a quick and simple mode of attachment between the string positioning member 104 and at least one adaptor member 136.

Figure 4A:
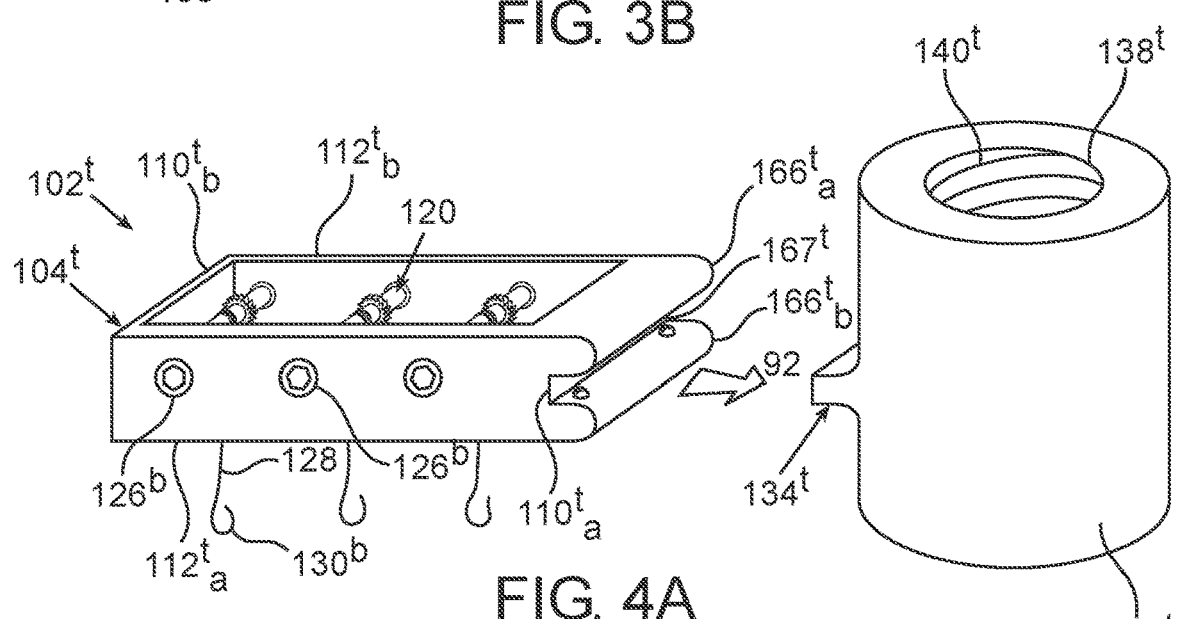
FIG. 4A constitutes a view in perspective of a strings positioning member detached from an adaptor body, according to some embodiments.

Reference is now made to FIGS. 4A-7D. FIG. 4A constitutes a view in perspective of a main body 102$^t$ of a distraction device 100$^t$, comprising string positioning member 104$^t$ detachably attachable to adaptor member 136$^t$, via a quick-snap type of attachment. String positioning member 104$^t$ comprises first and second sidewalls 112$^t$a and 112$^t$b, and rear and front panels 110$^t$a and 110$^t$b, respectively. According to some embodiments, at least one adaptor member 136 is configured to attach to string positioning member 104 at one end thereof, such as to rear panel 110$^t$a as depicted in FIG. 4A. Rear panel 110$^t$a comprises a positioning member's attachment means having frame ribs 166$^t$ and positioning member's grooves 167$^t$. Adaptor member 136$^t$ comprises adaptor attachment means 134$^t$ having adaptor ribs formed along at least a portion of the circumference of adaptor member 136$^t$.

Figure 4B:
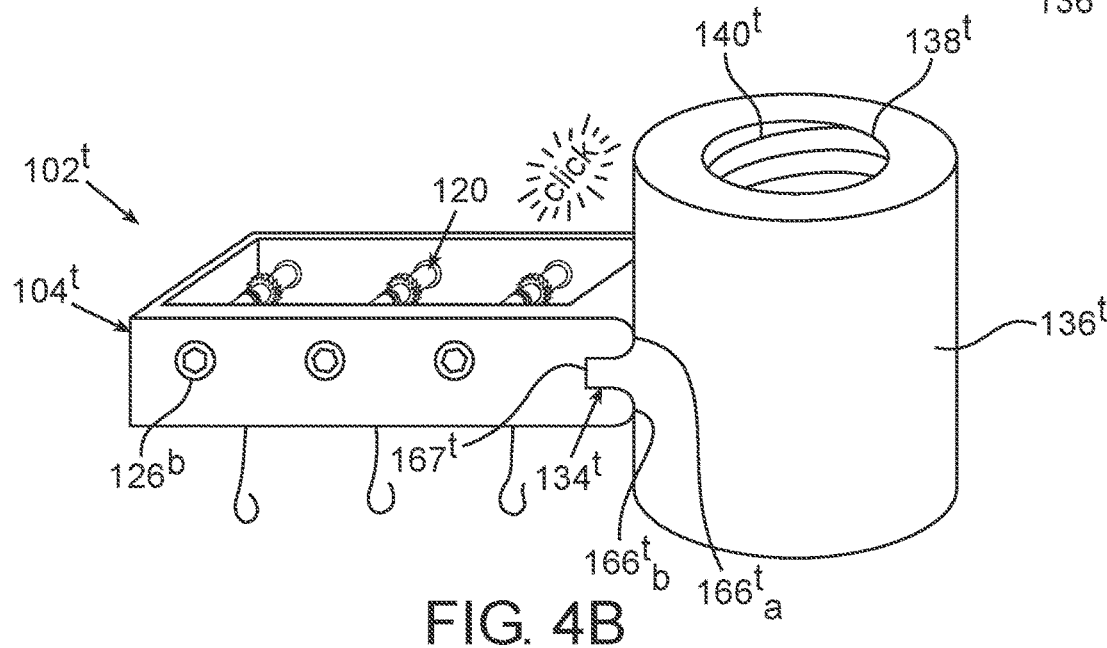
FIG. 4B constitutes a view in perspective of the strings positioning member attached to the adaptor body of FIG. 4A.

FIG. 4B constitutes a view in perspective of string positioning member 104$^t$ attached to adaptor member 136$^t$, for example by moving string positioning member 104$^t$ in the direction of arrows 92 (see FIG. 4A) towards adaptor attachment means 134$^t$. Adaptor ribs of adaptor attachment means 134$^t$ are formed to be received in grooves 167$^t$, stably positioned therein by friction forces from ribs 166$^t$, thereby securing and preventing spontaneous movement of string positioning member 104$^t$ relative to adaptor member 136$^t$.

While FIG. 4A depicts an embodiment of the positioning member's attachment means having two frame ribs 166$^t$ and one frame groove 167$^t$, and adaptor attachment means 134$^t$ having one adaptor rib, it will be understood by those skilled in the art that rear panel 110$^t$a can include any other amount of positioning member's ribs 166$^t$ and positioning member's grooves 167$^t$, and that adaptor attachment means 134$^t$ can include any other amount of adaptor ribs. Preferably, the number of adaptor ribs is matching the number of positioning member's grooves 167$^t$.

According to some embodiments, positioning member's ribs 166ᵗ are formed with rounded edges, as depicted in FIG. 4A. According to some embodiments, positioning member's grooves 167ᵗ are formed as rounded grooves (embodiments not shown). According to some embodiments, the adaptor ribs are formed with rounded edges (embodiments not shown). According to some embodiments, the geometrical form of the adaptor ribs matches the geometrical form of positioning member's grooves 167ᵗ.

According to some embodiments, positioning member's ribs 166ᵗ further comprise dimples (not numbered) facing matching surfaces of the adaptor ribs of adaptor attachment means 134ᵗ (see FIG. 4A), configured to press against the adaptor ribs when received within frame grooves 167ᵗ to further secure and prevent movement of string positioning member 104ᵏ relative to adaptor member 136ᵗ. According to some embodiments, the adaptor ribs of adaptor attachment means 134ᵗ further comprise notches (not shown) configured for alignment with the dimples of positioning member's ribs 166ᵗ.

According to some embodiments, the adaptor ribs of adaptor attachment means 134ᵗ further comprises dimples facing matching surfaces of positioning member's ribs 166ᵗ, configured to press against positioning member's ribs 166ᵗ to further secure and prevent movement of string positioning member 104ᵗ relative to adaptor member 136ᵗ (embodiments not shown). According to some embodiments, positioning member's ribs 166ᵗ the adaptor ribs further comprise notches (not shown) configured for alignment with the adaptor ribs of adaptor attachment means 134ᵗ.

Figure 5A:
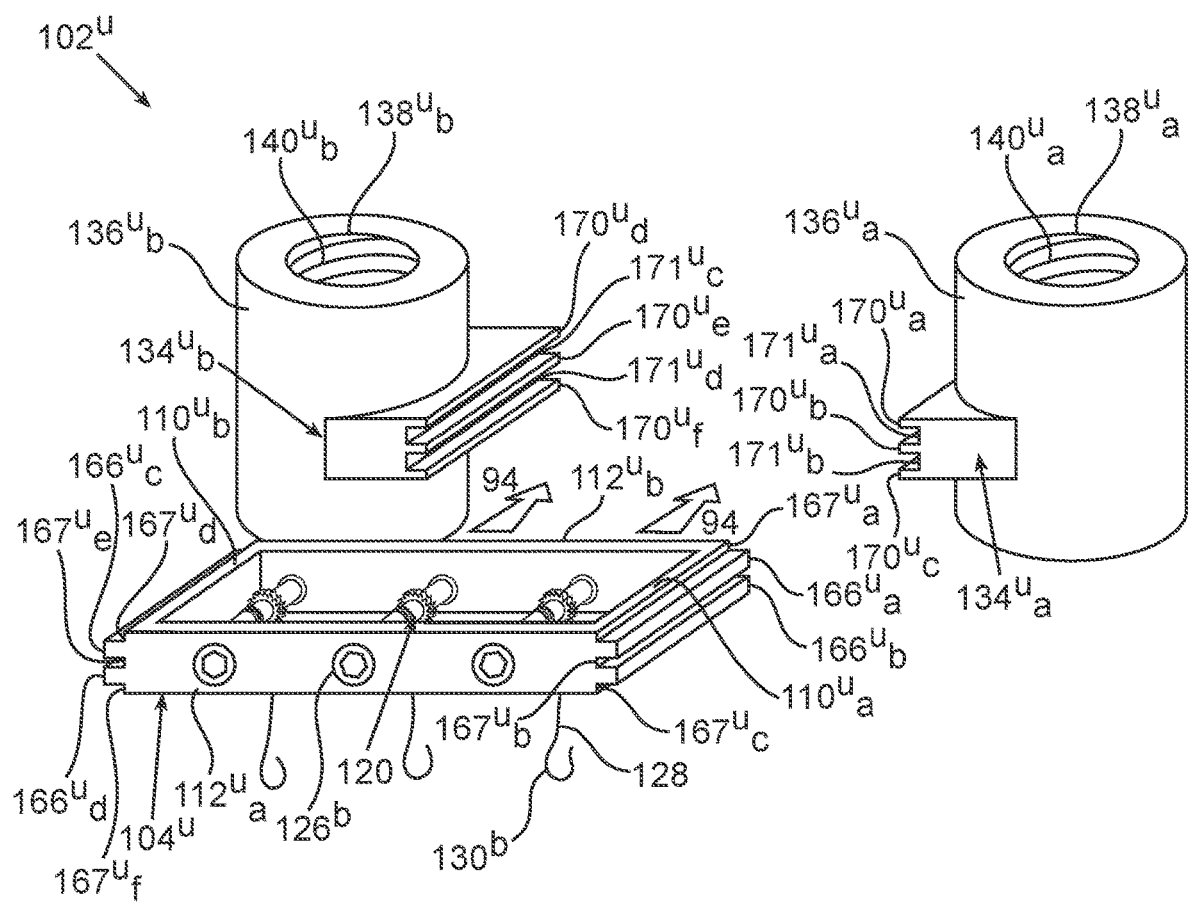
FIG. 5A constitutes a view in perspective of a strings positioning member detached from two adaptor bodies, according to some embodiments.

FIG. 5A constitutes a view in perspective of a main body 102ᵘ of a distraction device 100ᵘ, comprising string positioning member 104ᵘ detachably attachable to first adaptor member 136ᵘa and to second adaptor member 136ᵘb, via quick-snap type of attachments. String positioning member 104ᵘ comprises first and second sidewalls 112ᵘa and 112ᵘb, and rear and front panels 110ᵘa and 110ᵘb, respectively. Each of rear and front panels 110ᵘa and 110ᵘb comprises positioning member's attachment means having positioning member's ribs 166ᵘ and positioning member's grooves 167ᵘ. Each of first and second adaptor bodies 136ᵘa and 136ᵘb comprises first and second adaptor attachment means 134ᵘa and 134ᵘb, respectively, having adaptor ribs 170ᵘ and adaptor grooves 171ᵘ, formed along at least a portion of first and second adaptor bodies 136ᵘa and 136ᵘb, respectively.

Figure 5B:
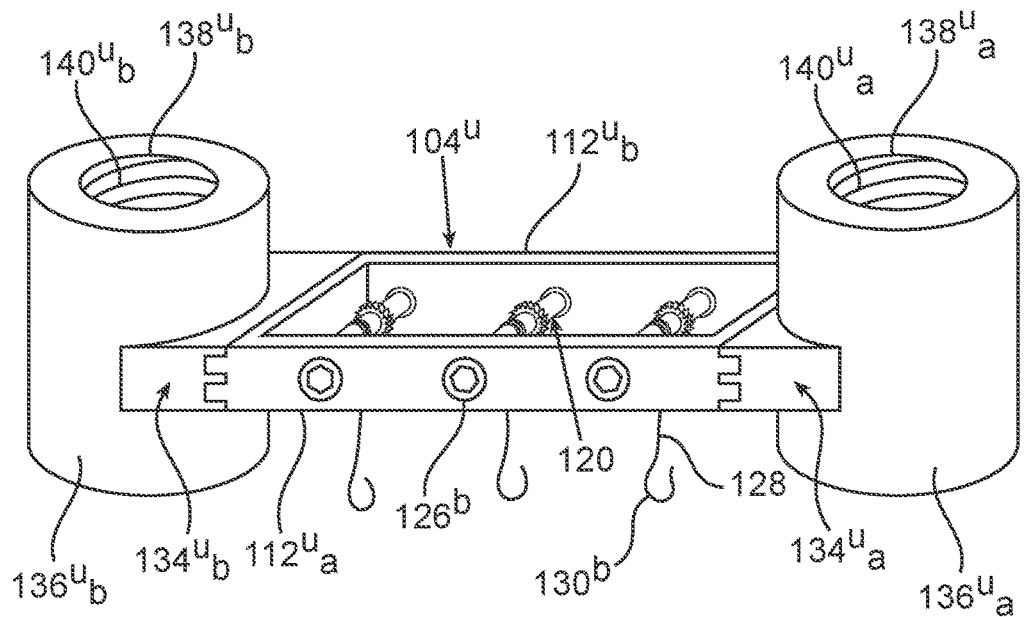
FIG. 5B constitutes a view in perspective of the strings positioning member attached to both adaptor bodies of FIG. 5A.

In the example depicted in FIGS. 5A-5B, rear panel 110ᵘa comprises positioning member's ribs 166ᵘa and 166ᵘb, and positioning member's grooves 167ᵘa, 167ᵘb and 167ᵘc. First adaptor attachment means 134ᵘa comprises adaptor ribs 170ᵘa, 170ᵘb and 170ᵘc, configured to be accommodated by positioning member's grooves 167ᵘa, 167ᵘb and 167ᵘc, respectively. First adaptor attachment means 134ᵘa further comprises adaptor grooves 171ᵘa and 171ᵘb, configured to accommodate positioning member's ribs 166ᵘa and 166ᵘb, respectively. Front panel 110ᵘb comprises positioning member's ribs 166ᵘc and 166ᵘd, and positioning member's grooves 167ᵘd, 167ᵘe and 167ᵘf. Second adaptor attachment means 134ᵘb comprises adaptor ribs 170ᵘd, 170ᵘe and 170ᵘf, configured to be accommodated by positioning member's grooves 167ᵘd, 167ᵘe and 167ᵘf, respectively. Second adaptor attachment means 134ᵘb further comprises adaptor grooves 171ᵘc and 171ᵘd, configured to accommodate positioning member's ribs 166ᵘc and 166ᵘd, respectively.

FIG. 5B constitutes a view in perspective of string positioning member 104ᵘ attached to first and second adaptor members 136ᵘa and 136ᵘb, respectively, for example by moving string positioning member 104ᵘ in the direction of arrows 94 (see FIG. 5A) to facilitate engagement between the frame attachment means of rear and front panels 110ᵘa and 110ᵘb and adaptor attachment means 134ᵘa and 134ᵘb, respectively. Adaptor ribs 170ᵘ and adaptor grooves 171ᵘ are formed for engagement with positioning member's grooves 167ᵘ and positioning member's ribs 166ᵘ, respectively, stably positioned therein by friction forces, thereby securing and preventing spontaneous movement of string positioning member 104ᵗ relative to any of first or second adaptor members 136ᵘa and 136ᵘb, respectively.

While FIGS. 5A and 5B depict an embodiment of each positioning member's attachment means having two frame ribs 166ᵘ and three grooves 167ᵘ, and each of first and second adaptor attachment means 134ᵘa and 134ᵘb having three adaptor ribs 170ᵘ and two adaptor grooves 171ᵘ, it will be understood by those skilled in the art that each of rear panel 110ᵘa and 110ᵘb can include any other amount of positioning member's ribs 166ᵘ and positioning member's grooves 167ᵘ, and that each of first and second adaptor attachment means 134ᵘa and 134ᵘb can include any other amount of adaptor ribs 170ᵘ and adaptor grooves 171ᵘ. Preferably, the number of adaptor ribs adaptor ribs 170ᵘ is matching the number of positioning member's grooves 167ᵘ configured to engage each other, and the number of adaptor ribs adaptor grooves 171ᵘ is matching the number of positioning member's ribs 166ᵘ configured to engage each other.

FIG. 6A constitutes a view in perspective of a main body 102ᵛ of a distraction device 100ᵛ, comprising a string positioning member 104ᵛ detachably attachable to a first adaptor member 136ᵛa and to a second adaptor member 136ᵛb, via quick-snap type of attachments. String positioning member 104ᵛ comprises first and second sidewalls 112ᵛa and 112ᵛb, and rear and front panels 110ᵛa and 110ᵛb, respectively. Each of rear and front panels 110ᵛa and 110ᵛb comprises positioning member's attachment means in the form of positioning member's ribs 166ᵛ and positioning member's grooves 167ᵛ. Each of first and second adaptor members 136ᵛa and 136ᵛb comprises first and second adaptor attachment means 134ᵛa and 134ᵛb, respectively, having circumferential adaptor ribs 170ᵛ and circumferential adaptor grooves 171ᵛ formed along the complete circumference first and second adaptor member 136ᵛa and 136ᵛb, respectively.

In the example depicted in FIGS. 6A-6B, rear panel 110ᵛa comprises positioning member's ribs 166ᵛa and 166ᵛb, and positioning member's grooves 167ᵛa, 167ᵛb and 167ᵛc. First adaptor attachment means 134ᵛa comprises adaptor ribs 170ᵛa, 170ᵛb and 170ᵛc, configured to be accommodated by positioning member's grooves 167ᵛa, 167ᵛb and 167ᵛc, respectively. First adaptor attachment means 134ᵛa further comprises adaptor grooves 171ᵛa and 171ᵛb, configured to accommodate positioning member's ribs 166ᵛa and 166ᵛb, respectively. Front panel 110ᵛb comprises positioning member's ribs 166ᵛc and 166ᵛd, and positioning member's grooves 167ᵛd, 167ᵛe and 167ᵛf. Second adaptor attachment means 134ᵛb comprises adaptor ribs 170ᵛd, 170ᵛe and 170ᵛf, configured to be accommodated by positioning member's grooves 167ᵛd, 167ᵛe and 167ᵛf, respectively. Second adaptor attachment means 134ᵛb further comprises adaptor grooves 171ᵛc and 171ᵛd, configured to accommodate positioning member's ribs 166ᵛc and 166ᵛd, respectively.

Rear and front panels 110ᵛa and 110ᵛb, respectively, along with positioning member's ribs 166ᵛ and positioning member's grooves 167ᵛ, are curved arcuately, formed to match the circumferential shape of first and second adaptor attachment means 134ᵛa and 134ᵛb, along with circumferential adaptor ribs 170ᵛ and circumferential adaptor grooves 171ᵛ, respectively.

FIG. 6B constitutes a view in perspective of string positioning member $104^V$ attached to first and second adaptor members $136^V$a and $136^V$b, for example by moving string positioning member $104^V$ in the direction of arrows 96 (see FIG. 6A) to facilitate engagement between the positioning member's attachment means of rear and front panels $110^V$a and $110^V$b and adaptor attachment means $134^V$a and $134^V$b, respectively. Adaptor ribs $170^V$ and adaptor grooves $171^V$ are formed for engagement with positioning member's grooves $167^V$ and positioning member's ribs $166^V$, respectively, stably positioned therein by friction forces, thereby securing and preventing spontaneous movement of positioning member's $104^V$ relative to any of first or second adaptor bodies $136^V$a and $136^V$b, respectively.

Advantageously, the arcuate shape of the frame attachment means of rear and front panels $110^V$a and $110^V$b, matching the circumferential shape of adaptor attachment means $134^V$a and $134^V$b, respectively, enables an operator of distraction device $100^V$ to rotate any one of first and second adaptor members $136^V$a and $136^V$b, respectively, while string positioning member $104^V$ remains engaged thereto. This may be achieved by designing the positioning member's attachment means of rear and front panels $110^V$a and $110^V$b, and adaptor attachment means $134^V$a and $134^V$b, to generate frictional force when engaged with each other so as to prevent spontaneous relative movement when no other external force, higher than the frictional force, is acting against any of string positioning member $104^V$ or first or second adaptor members $136^V$a and $136^V$b, respectively. However, manual rotation of any one of first and second adaptor members $136^V$a and $136^V$b, respectively, at a force higher than the frictional force, enables such relative movement, and once such forced rotation is complete, the frictional force once again acts to prevent spontaneous movement between string positioning member $104^V$ and any of first or second adaptor members $136^V$a and $136^V$b, respectively.

While FIGS. 6A-6B depict an embodiment of string positioning member 104 formed to engage with two adaptor members 136, in a manner which enables rotation of each one of adaptor members 136 while keeping string positioning member 104 engaged thereto, it will be understood by those skilled in the art that similar configuration may be adapted to string positioning member 104 being formed to engage with a single adaptor member 136.

In the example depicted in FIGS. 6A-6B, distraction device $100^V$ comprises vertical string pull assemblies $120^V$ (not shown) disposed between proximal panel $106^V$ (not shown) and distal panel $108^V$, each comprising tooling interface $126^V$ (similar to vertical string pull assemblies $120^C$ depicted in FIG. 12 and further described herein below). It will be understood by those skilled in the art that distraction device $100^V$ may alternatively include any other embodiments of string pull assemblies 120, disclosed throughout the specification.

While FIGS. 6A-6B depict an embodiment of each frame attachment means having two positioning member's ribs $166^V$ and three grooves $167^V$, and each of first and second adaptor attachment means $134^V$a and $134^V$b, respectively, having three adaptor ribs $170^V$ and two adaptor grooves $171^V$, it will be understood by those skilled in the art that each of rear panel $110^V$a and $110^V$b can include any other amount of positioning member's ribs $166^V$ and positioning member's grooves $167^V$, and that each of first and second adaptor attachment means $134^V$a and $134^V$b, respectively, can include any other amount of adaptor ribs $170^V$ and adaptor grooves $171^V$. Preferably, the number of adaptor ribs $170^V$ is matching the number of positioning member's grooves $167^V$ configured to engage each other, and the number of adaptor grooves $171^V$ is matching the number of positioning member's ribs $166^V$ configured to engage each other.

Figure 7A:
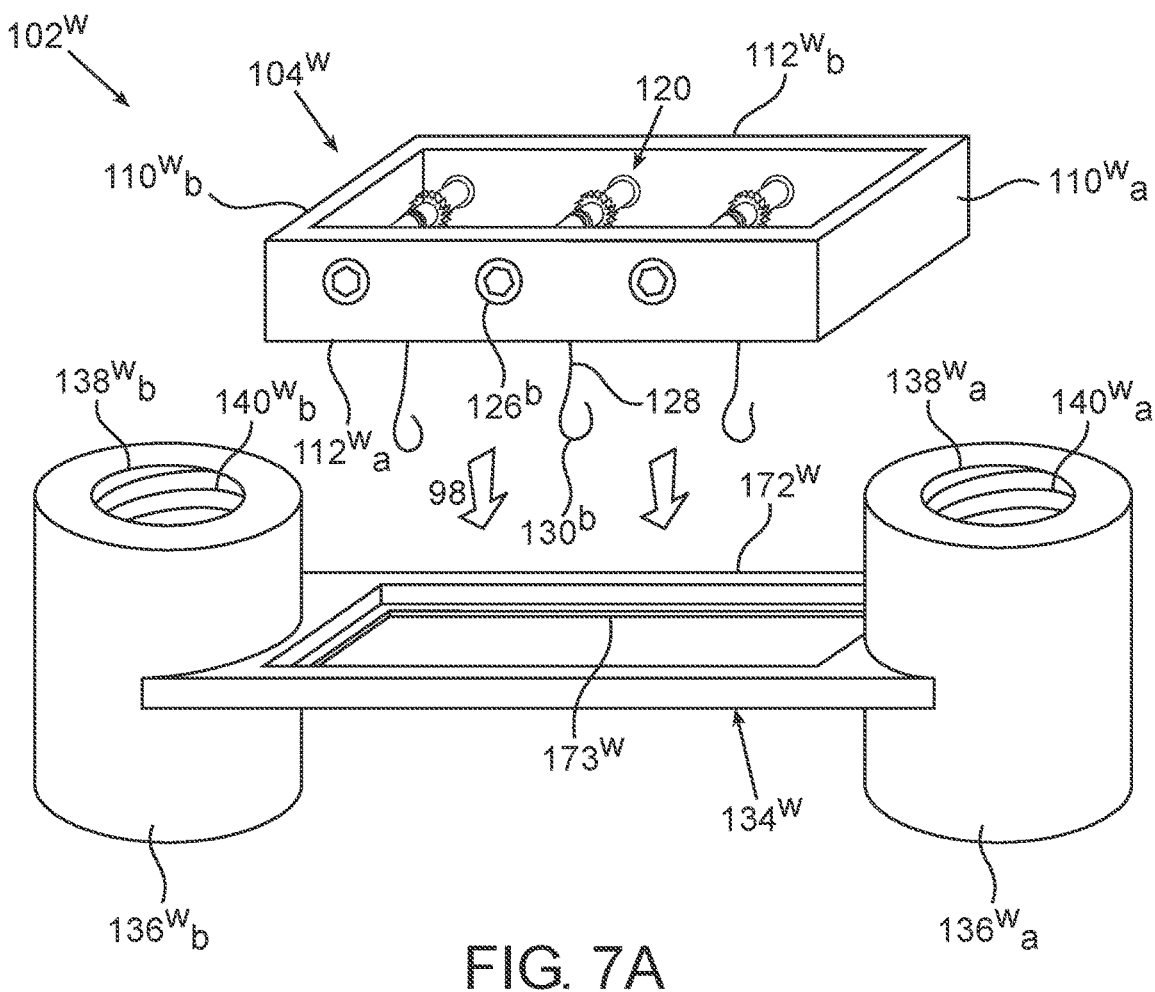
FIG. 7A constitutes a view in perspective of a strings positioning member detached from two connected adaptor bodies, according to some embodiments.

FIG. 7A constitutes a view in perspective of a main body $102^W$ of a distraction device $100^W$, comprising a string positioning member $104^W$ detachably attachable to a first adaptor member $136^W$a and a second adaptor member $136^W$b, via quick-snap type of attachments, wherein first and second adaptor members $136^W$a and $136^W$b are connected to each other via adaptor attachment means $134^W$. String positioning member $104^W$ comprises first and second sidewalls $112^W$a and $112^W$b, and rear and front panels $110^W$a and $110^W$b, respectively. Adaptor attachment means $134^W$ comprises an adaptor attachment socket $172^W$, formed to receive string positioning member $104^W$ therein.

Figure 7B:
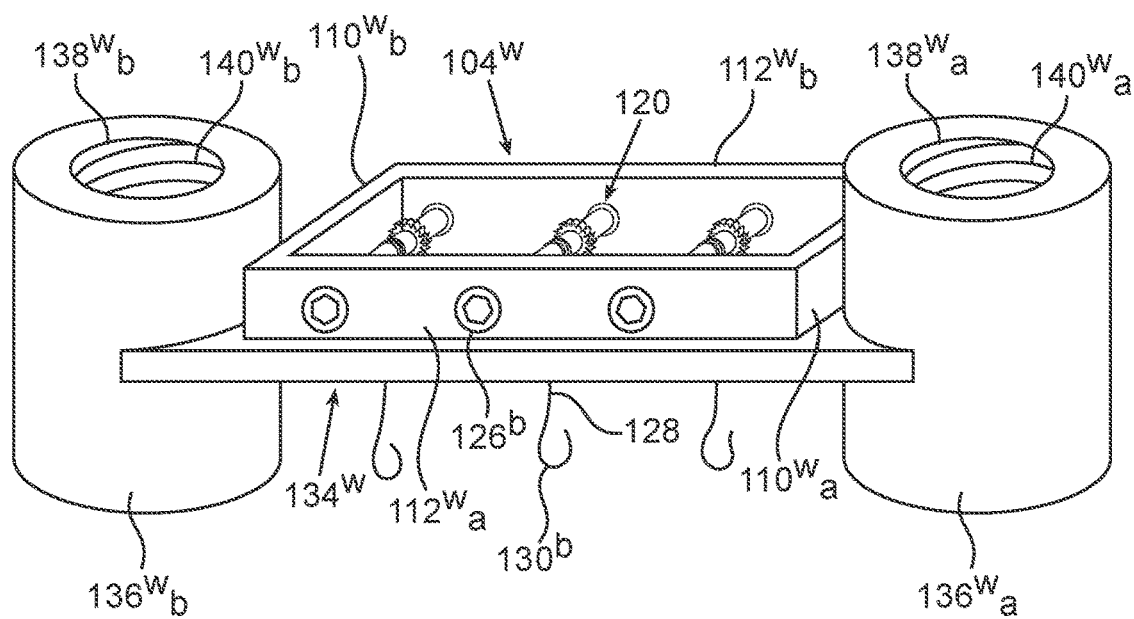
FIG. 7B constitutes a view in perspective of the strings positioning member attached to the two connected adaptor bodies of FIG. 7A.

FIG. 7B constitutes a view in perspective of string positioning member $104^W$ attached to first and second adaptor members $136^W$a and $136^W$b, for example by moving string positioning member $104^W$ in the direction of arrows 98 (see FIG. 7A) to facilitate engagement between the sidewalls of adaptor attachment socket $172^W$ (not numbered) and rear panel $110^W$a, front panel $110^W$b, first sidewall $112^W$a and second sidewall $112^W$b. String positioning member $104^W$ is stably positioned within adaptor attachment socket $172^W$ by friction forces acting there between, thereby securing and preventing spontaneous movement of string positioning member $104^W$ relative to any of first or second adaptor members $136^W$a and $136^W$b.

According to some embodiments, adaptor attachment means $134^W$ is rigidly attached to first and second adaptor members $136^W$a and $136^W$b. According to some embodiments, adaptor attachment means $134^W$ is integrally formed with first and second adaptor members $136^W$a and $136^W$b. According to some embodiments, adaptor attachment means $134^W$ is detachably attached to first and second adaptor members $136^W$a and $136^W$b.

According to some embodiments, string positioning member $104^W$ is pushed in the direction of arrows 98 (see FIG. 7A), such that only a portion of rear panel $110^W$a, front panel $110^W$b, first sidewall $112^W$a and second sidewall $112^W$b are engaged with the sidewalls of adaptor attachment socket $172^W$, leaving tooling interface 126, such as tooling interface $126^W$ disposed along at least first sidewall $112^W$a, exposed for access (for example, access to rotation tools 76 described herein below) and unblocked by adaptor attachment socket $172^W$ (see FIG. 7B).

According to some embodiments, adaptor attachment socket $172^W$ further comprises a socket seat $173^W$ (see FIG. 7A), such that string positioning member $104^W$ can be pushed in the direction of arrows 98 until it abuts against socket seat $173^W$. Socket seat $173^W$ is configured to prevent further movement of string positioning member $104^W$ in the direction of arrows 98, at a position such that tooling interfaces 126 are exposed for access and unblocked by adaptor attachment socket $172^W$ (see FIG. 7B).

Figure 7C:
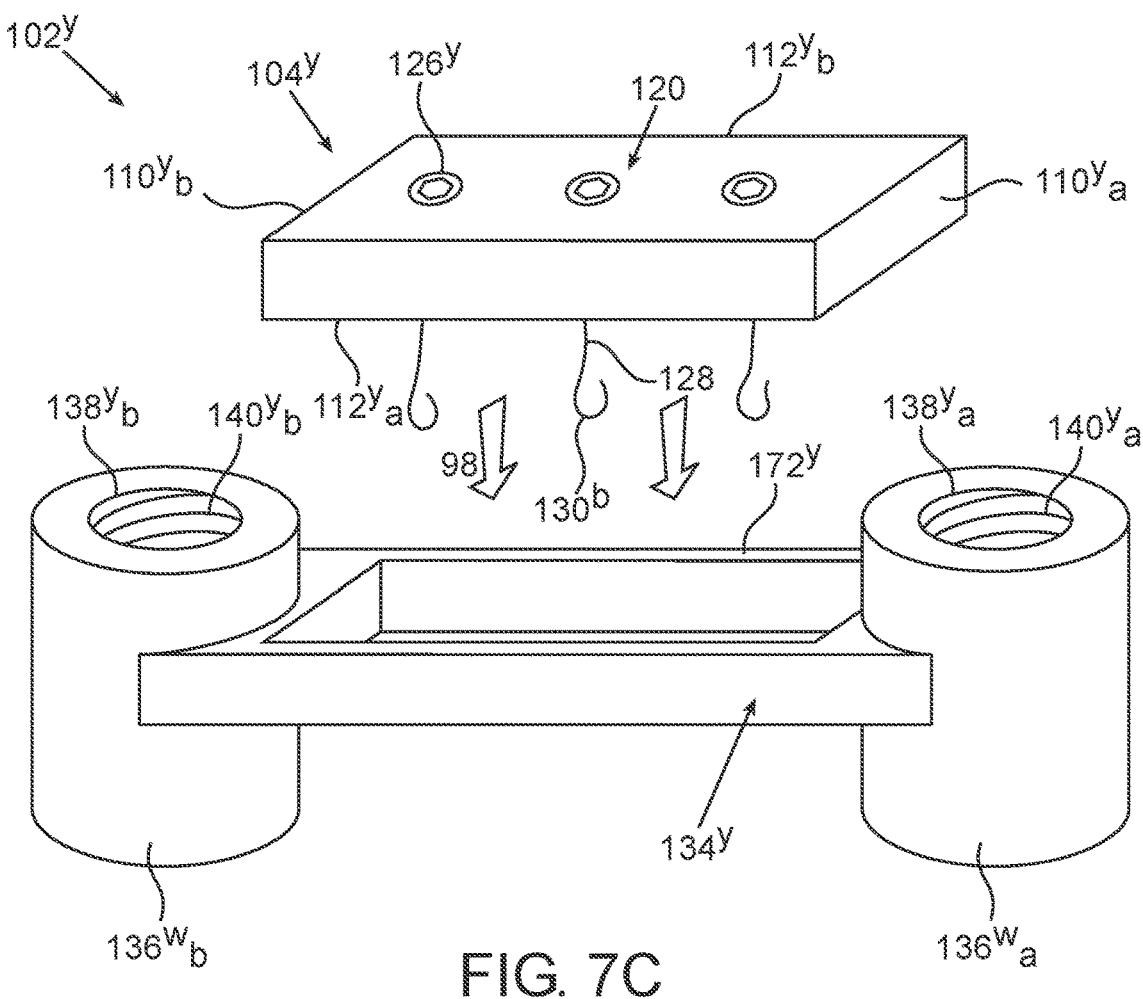
FIG. 7C constitutes a view in perspective of a strings positioning member detached from two connected adaptor bodies, according to some embodiments.

FIG. 7C constitutes a view in perspective of a main body $102^W$ of a distraction device $100^Y$, comprising a string positioning member $104^W$ detachably attachable to a first adaptor member $136^Y$a and a second adaptor member $136^Y$b, via quick-snap type of attachments, wherein first and second adaptor members $136^Y$a and $136^Y$b are connected to each other via adaptor attachment means $134^W$. String positioning member $104^W$ comprises first and second sidewalls $112^Y$a and $112^Y$b, and rear and front panels $110^Y$a and $110^Y$b, respectively. Adaptor attachment means $134^W$ comprises an adaptor attachment socket 172$^w$, formed to receive string positioning member 104$^w$ therein.

Figure 7D:
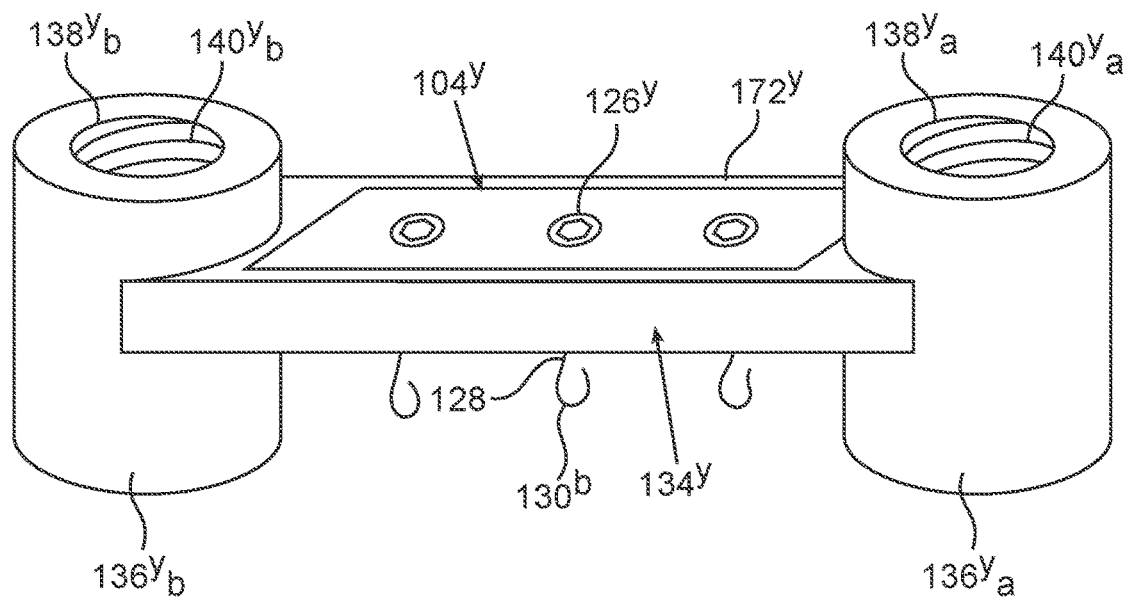
FIG. 7D constitutes a view in perspective of the strings positioning member attached to the two connected adaptor bodies of FIG. 7C.

FIG. 7D constitutes a view in perspective of string positioning member 104$^w$ attached to first and second adaptor members 136$^y$a and 136$^y$b, for example by moving string positioning member 104$^w$ in the direction of arrows 98 (see FIG. 7C) to facilitate engagement between the sidewalls of adaptor attachment socket 172$^w$ (not numbered) and rear panel 110$^y$b, front panel 110$^y$b, first sidewall 112$^y$y and second sidewall 112$^y$b. String positioning member 104$^w$ is stably positioned within adaptor attachment socket 172$^w$ by friction forces acting there between, thereby securing and preventing spontaneous movement of string positioning member 104$^w$ relative to any of first or second adaptor members 136$^y$a and 136$^y$b.

According to some embodiments, adaptor attachment means 134$^w$ is rigidly attached to first and second adaptor members 136$^y$a and 136$^y$b. According to some embodiments, adaptor attachment means 134$^w$ is integrally formed with first and second adaptor members 136$^y$a and 136$^y$b. According to some embodiments, adaptor attachment means 134$^w$ is detachably attached to first and second adaptor members 136$^y$a and 136$^y$b.

In the example depicted in FIGS. 7C-7D, string positioning member 104$^w$ comprises vertical string pull assemblies 120$^w$ (not shown, similar to vertical string pull assemblies 120$^c$ depicted in FIG. 12 and further described herein below) with tooling interfaces 126$^w$ disposed along distal panel 108$^w$, thereby enabling insertion of string positioning member 104$^w$ into adaptor attachment socket 172$^w$ for engagement therewith, without the risk of tooling interfaces 126$^w$ being blocked by adaptor attachment socket 172$^w$.

Advantageously, string positioning member 104$^y$ having tooling interfaces 126$^w$ disposed along distal panel 108$^y$ enables rear panel 110$^y$a, front panel 110$^y$b, first sidewall 112$^y$a and second sidewall 112$^y$b, according to some embodiments, to be designed to engage with the sidewalls of adaptor attachment socket 172$^w$ along the entire vertical height thereof (see FIGS. 7C-7D), thereby providing a larger engagement surface between string positioning member 104$^y$ and adaptor attachment socket 172$^w$, for example in comparison to distraction device 100$^w$.

According to some embodiments, at least one adaptor member 136 is configured for attachment to string positioning member 104 using alternative mechanical affixation methods, including, but not limited to soldering, prongs, fasteners, biocompatible adhesives and/or via alternative structures that may extend either from at least one adaptor member 136, from string positioning member 104, or from both.

According to some embodiments, distraction device 100 is supplied as a kit including string positioning member 104 and at least one adaptor member 136, separated from one another and configured for to be coupled together prior to placement over a jawbone as further disclosed herein.

According to some embodiments, string positioning member 104 is symmetrical such that rear and front panels 110a and 110b, respectively, are interchangeably, and string positioning member 104 may be rotated to either side such that rear panel 110a acts as front panel 110b, and front panel 110b acts as rear panel 110a.

As used herein, the term "front panel 110", when mentioned in embodiments not specifically discriminating between rear and front panels 110a and 110b, refers to front panel 110b.

It will be clear that string positioning member 104 and at least one adaptor member 136 are not limited to the geometries or attachment type exemplified hereinabove, and that the configurations depicted in FIGS. 4A-7D serve as mere examples, while a person skilled in the art may utilize any other attachment methods and supporting structures between string positioning member 104 and at least one adaptor member 136, as known in the art.

According to some embodiments, string positioning member 104 is symmetrical such that first and second sidewalls 112a and 112b are interchangeably, and string positioning member 104 may be rotated to either side such that first sidewall 112a acts as second sidewall 112b, and second sidewall 112b acts as first sidewall 112a.

According to some embodiments, at least one component of the distraction device 100, such as a main body 102, a strings positioning member 104, at least one string pull assembly 120, at least one adaptor member 136 or the like, is manufactured via the use of CAD-CAM software and CAD-CAM operated machines, based on at least one design file supplied to the CAD-CAM software.

The term CAD, as used herein, refers to Computer Aided Design.

The term CAM, as used herein, refers to Computer Aided Manufacturing.

According to some embodiments, the design file includes instructions for manufacturing the at least one component of the distraction device 100 according to a design specific to a patient, accounting for various parameters such as the geometry of the patient's jaw, the geometry of a patent-specific alveolar ridge atrophy, the geometry of mounts such as dentures or the patient's native teeth, the size and geometry of adjacent components of the distraction device 100.

As used herein, the terms "adaptor member" and "at least one adaptor member" are interchangeable, and refer to either a single adaptor member 136 or a plurality of adaptor members 136.

According to some embodiments, tooling interface 126 comprises a screw-drive (not numbered). In FIG. 8A, the screw-drive of tooling interface 126 is in the form of a Phillips or Fearson socket. In FIG. 8B, the screw-drive of tooling interface 126$^a$ is in the form of a hex or an Allen screw-head. In FIG. 8C, the screw-drive of tooling interface 126$^b$ is in the form of a hex or an Allen socket. It will be understood by those skilled in the art that other screw-drive shapes may be implemented, such as, but not limited to, Slot, Square, Robertson, Torx, TA, Tri-Wing, Clutch, Spanner-Head, Double-Square, Triple-Square, Double-Hex, Bristol and the like.

The term "screw-drive", as used herein, refers to either screw-heads adapted to fit with a rotation tool in the form of screwdrivers, or to extension s formed with facets, adapted to fit rotation tools such as wrenches.

FIG. 9A depicts rotation tool 76, engaged with tooling interface 126$^b$ in the direction of arrow 80. FIG. 9B shows rotation of rotation tool 76 in the direction of arrow 82. Such rotation, while rotation tool 76 is engaged with tooling interface 126$^b$, will cause movable element 122 formed as a shaft to rotate in the same direction 82, thereby shortening the length of the unwrapped portion of string 128. According to some embodiments, rotation of rotation tool 76 in the direction opposite to arrow 82 is limited due to engagement of pawl 114 with gear 124.

According to some embodiments, rotation of tooling interface 126 is performed with optional proprietary and/or customized tools. FIG. 9A depicts an embodiment of rotation tool 76$^a$, engaged with tooling interface 126$^b$ and rotating in direction 84.

The profile of rotation tool 76 corresponds with the screw-drive shape of tooling interface 126. FIGS. 9A-9C depict embodiments of a rotation tool 76 or 76$^a$, shaped with an Allen head, inserted into the screw-drive socket of tooling interface 126$^b$. However, rotation tool 76 may comprise other engagement forms, configured either for engagement with an inner socket or an outer circumferential profile of the tooling interface 126, such as but not limited to, a screwdriver, a wrench, or a spanner.

FIGS. 8A-8C depict embodiments of tooling interfaces 126 having a screw-drive, configured for engagement with a rotation tool 76. However, it will be understood by those skilled in the art, that tooling interfaces 126 may comprise other features that enable its rotation, such as handles or extensions (not illustrated) that can be grasped either by tool or by hand, to be rotated in a similar manner.

According to some embodiments, mounting bore 138 comprises socket screw thread 140 (see FIGS. 1A-4B). According to some embodiments, mounting bore 138 comprises a polyhedral-shaped structure (see FIGS. 10A-10B).

FIGS. 1A-10C depict exemplary embodiments of distraction device 100 comprising three string pull assemblies 120. However, it will be understood by those skilled in the art that distraction device 100 may comprise any other amount of string pull assemblies, for example with corresponding pawls, such as one, two, four and so on.

According to some embodiments, the plurality of string pull assemblies 120 are aligned in parallel with each other. According to some embodiments, the plurality of string pull assemblies 120 are horizontally spaced from each other at even distances. According to some embodiments, the plurality of string pull assemblies 120 are horizontally spaced from each other at uneven distances.

The term plurality, as used herein, refers to more than one.

The terms horizontal or horizontal plane, as used herein, are interchangeable and refer to a plane parallel to proximal panel 106 or to distal panel 108, as illustrated and oriented in FIGS. 1A-10A. The terms vertical of vertical direction, as used herein, are interchangeable and refer to a direction perpendicular to the horizontal plane, for example parallel to axis 32 (see FIG. 1A).

The terms "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

According to some embodiments, proximal panel 106 spans along a single horizontal plane. According to some embodiments, distal panel 108 spans along a single horizontal plane. According to some embodiments, string positioning member 104 is formed as a fully straight frame, meaning that the proximal and distal edges (not numbered) of each of first sidewall 112$a$ and second sidewall 112$b$, are straight between adaptor member 136 and front panel 110.

According to some embodiments, string positioning member 104 is formed as a fully straight frame, such that the proximal and distal edges of each of first sidewall 112$a$ and second sidewall 112$b$ are parallel to a horizontal plane, each edge being perpendicular to the vertical direction (see FIGS. 1A-10A). According to some embodiments, string positioning member 104 is formed as a fully straight frame, such that the proximal and distal edges of each of first sidewall 112$a$ and second sidewall 112$b$ are angled relative to a horizontal plane, each edge being angled at a non-perpendicular angle relative to the vertical direction.

According to some embodiments, string positioning member 104 is formed as a plate, which spans along a single horizontal plane (embodiments not shown).

According to some embodiments, string positioning member 104 is formed as a partially straight frame, meaning that only either the proximal edges or the distal edges of each of first sidewall 112$a$ and second sidewall 112$b$, are straight between adaptor member 136 and front panel 110.

According to some embodiments, string positioning member 104 is formed as a partially straight frame, such that the proximal edges or the distal edges of each of first sidewall 112$a$ and second sidewall 112$b$ are arcuate.

According to some embodiments, string positioning member 104 is formed as a partially straight frame, such that the proximal edges or the distal edges of each of first sidewall 112$a$ and second sidewall 112$b$ are shaped to conform to a shape of a jawbone, such as the maxilla.

According to some embodiments, string positioning member 104 is formed as a non-straight frame, meaning that none of the proximal and the distal edges of each of first sidewall 112$a$ and second sidewall 112$b$, are straight between adaptor member 136 and front panel 110. According to some embodiments, string positioning member 104 is formed as a non-straight plate (embodiments not shown).

According to some embodiments, string positioning member 104 is formed as a non-straight frame, such that at least the proximal edges or the distal edges of each of first sidewall 112$a$ and second sidewall 112$b$ are arcuate.

According to some embodiments, string positioning member 104 is formed as a non-straight frame, such that at least the proximal edges or the distal edges of each of first sidewall 112$a$ and second sidewall 112$b$, are shaped to conform to a shape of a jawbone, such as the maxilla.

Figure 11A:
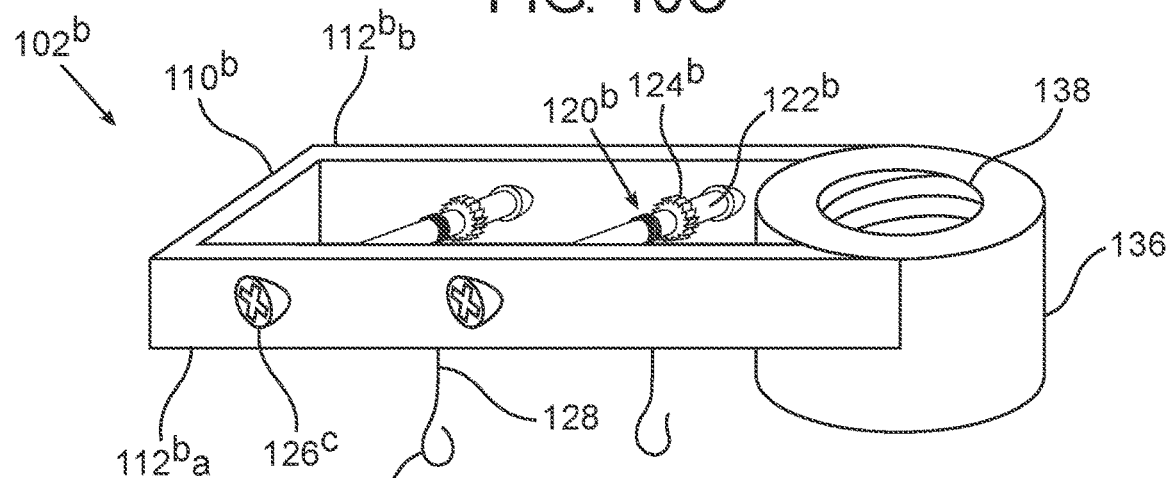
FIG. 11A constitutes a view in perspective of a distraction device having diagonal string pull assemblies, according to some embodiments.
Figure 11B:
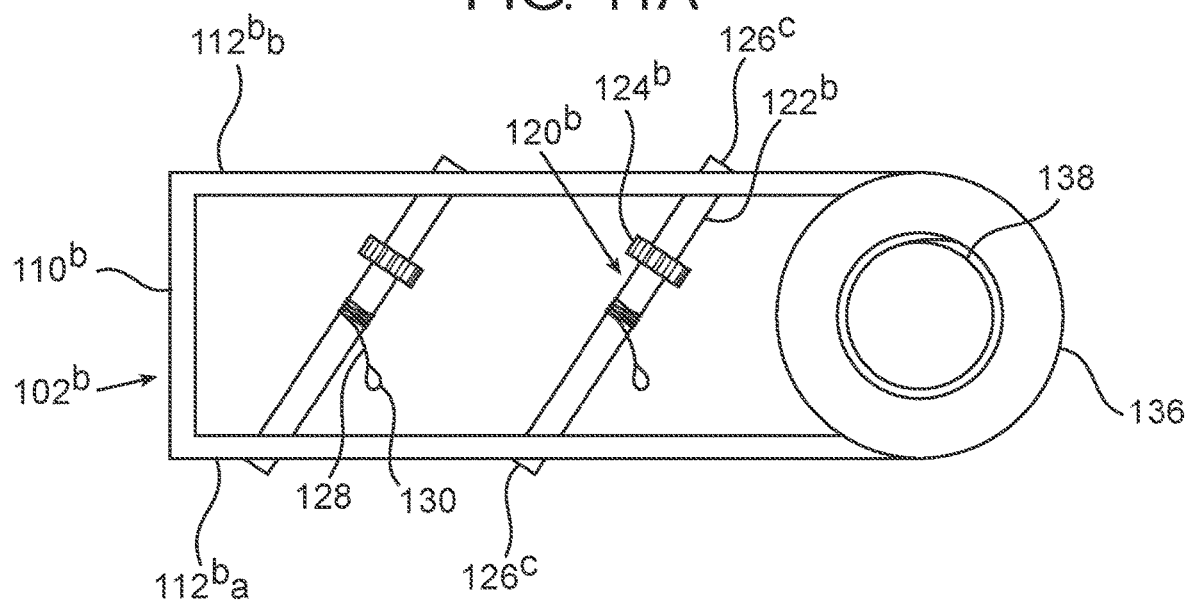
FIG. 11B constitutes a top view of a distraction device having diagonal string pull assemblies, according to some embodiments.

Reference is now made to FIGS. 11A-13D, depicting different embodiments of string pull assemblies 120 attached to a string positioning member 104. According to some embodiments, at least one string pull assembly 120 is oriented diagonally relative sidewalls 112, so as to be angled at an angle greater or smaller than 90° relative to either first sidewall 112$a$ or second sidewall 112$b$. FIGS. 11A and 11B constitute a view in perspective and a top view, respectively, of a distraction device 100$^b$ having two exemplary parallel diagonal string pull assemblies 120$^b$ attached to main body 102$^b$, horizontally angled relative to either first sidewall 112$^b$a or second sidewall 112$^b$b. Each string pull assembly 120$^b$ comprises a movable element 122$^b$, a gear 124$^b$ rigidly attached to movable element 122$^b$, a string 128 affixed to movable element 122$^b$, and at least one tooling interface 126, extending through at least one sidewall 112$^b$.

According to some embodiments, at least one string pull assembly 120 is rotateably attached to distal panel 108, such that at least one tooling interface 126 is exposed there through. According to some embodiments, the at least one string pull assembly 120 is oriented vertically between proximal panel 106 and distal panel 108. According to some embodiments, the at least one vertical string pull assembly 120 is attached to both proximal panel 106 and distal panel 108, such that a tooling interface 126 extends through the distal panel 108. According to some embodiments, the at least one vertical string pull assembly 120 is attached to distal panel 108 but not to proximal panel 106, such that a tooling interface 126 is exposed through the distal panel 108.

Figure 12:
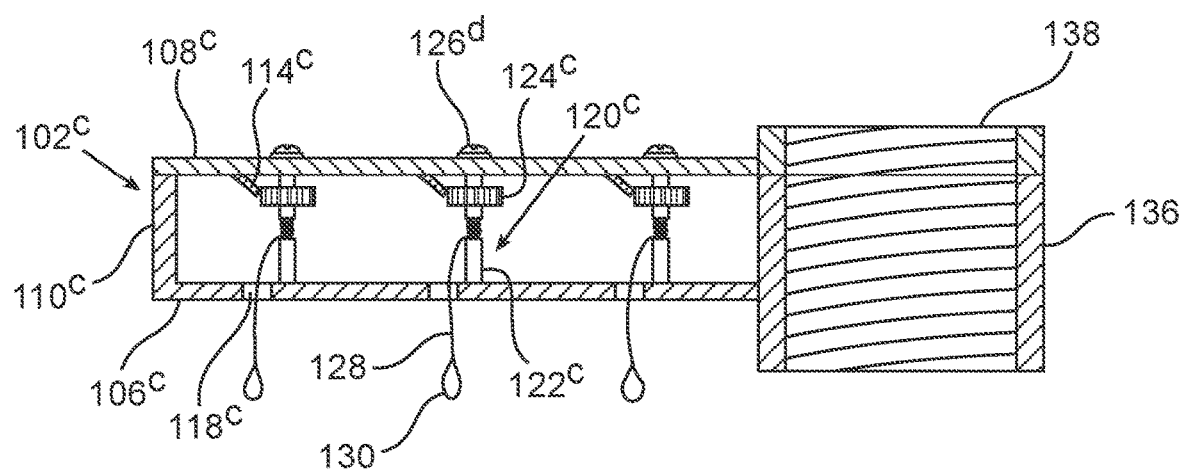
FIG. 12 constitutes a cross-sectional side view of a distraction device having vertical string pull assemblies, according to some embodiments.

FIG. 12 constitutes a cross-sectional side view of a distraction device 100$^c$ having three exemplary vertical string pull assemblies 120$^c$, disposed between proximal panel 106$^c$ and distal panel 108$^c$ of main body 102$^c$, and in parallel with front panel 110$^c$. Each string pull assembly 120$^c$ comprises a movable element 122$^c$, a gear 124$^c$ rigidly attached to movable element 122$^c$, string 128 affixed to movable element 122$^b$ and extending through an positioning feature 118$^c$ of proximal panel 106$^c$, and tooling interface 126$^d$, extending through distal panel 108$^d$.

According to some embodiments, at least one string pull assembly 120 is rotateably attached to front panel 110, such that at least one tooling interface 126 is exposed there through. According to some embodiments, at least one longitudinal string pull assembly 120 is attached to both front panel 110 and an outer surface (not numbered) of adaptor member 136. According to some embodiments, the at least one string pull assembly 120 is attached to front panel 110 but not to an outer surface of adaptor member 136.

Figure 13A:
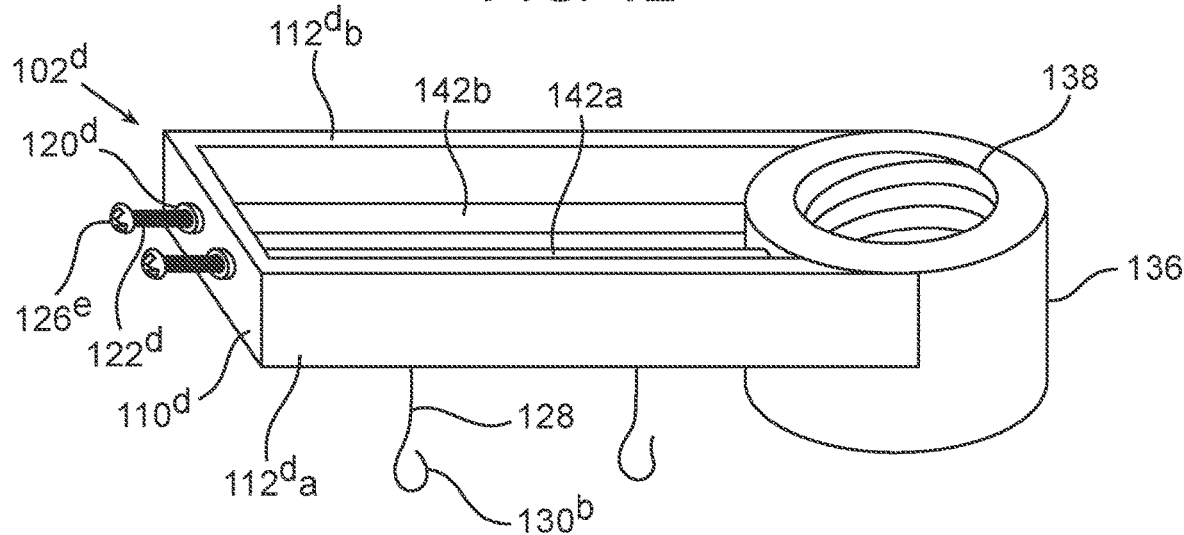
FIG. 13A constitutes a view in perspective of a distraction device having longitudinal string pull assemblies, according to some embodiments.
Figure 13B:
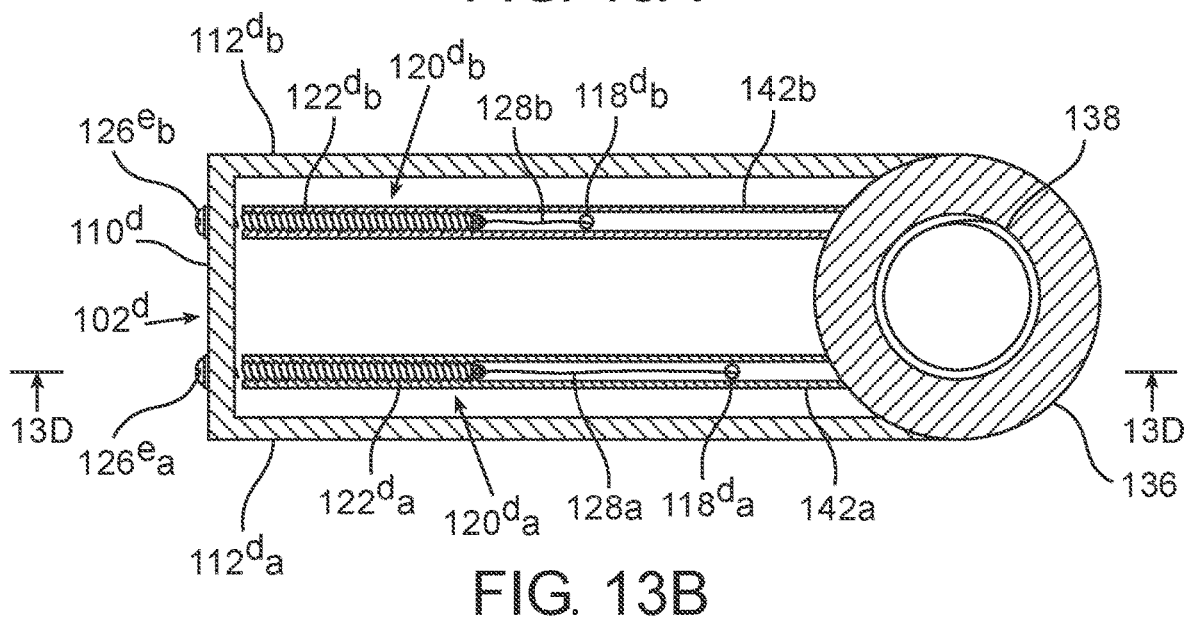
FIG. 13B constitutes a cross-sectional top view of the distraction device of FIG. 13A, showing the string pull assemblies in a first position, according to some embodiments.

FIGS. 13A and 13B constitute a view in perspective and a cross-sectional top view, respectively, of distraction device 100$^d$ having two exemplary longitudinal string pull assemblies 120$^d$a and 120$^d$b, disposed between front panel 110$^d$ and an outer surface of adaptor member 136, and in parallel with first sidewall r and second sidewall 112$^d$b. Each string pull assembly 120$^d$ comprises a movable element 122$^d$, a string 128 affixed to movable element 122$^d$ and extending through an aperture 118$^d$ of proximal panel 106$^d$, and a tooling interface 126$^e$, extending through front panel 110$^d$. Each movable element 122$^d$ is formed as a screw having a screw threading (not numbered). Each string pull assembly 120$^d$ further comprises a channel 142, having a threading along at least a portion of its length, corresponding to the screw threading of movable element 122$^d$ formed as a shaft, configured to enable longitudinal movement of movable element 122$^d$ along its length. Channel 142 further comprises an opening (not numbered) through which string 128 may pass towards positioning feature 118$^d$.

Figure 13C:
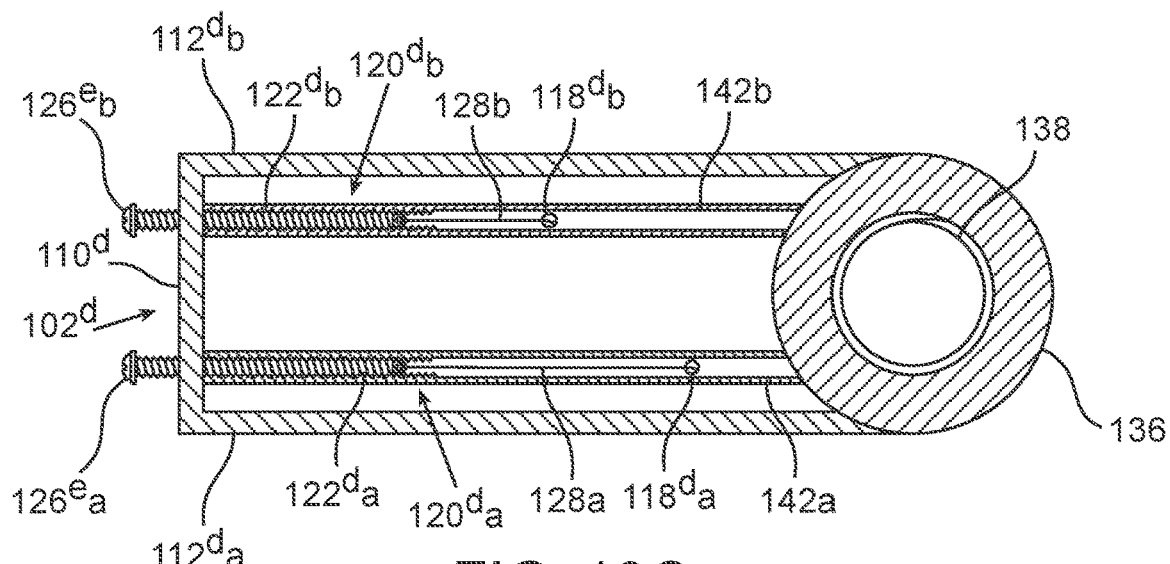
FIG. 13C constitutes a cross-sectional top view of the distraction device of FIG. 13B, showing the string pull assemblies in a second position, according to some embodiments.
Figure 13D:
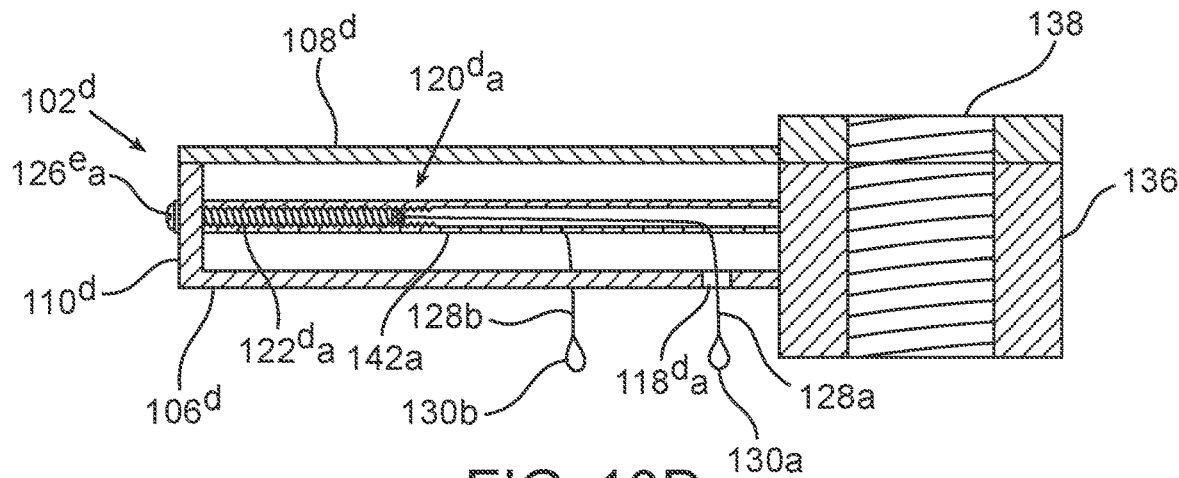
FIG. 13D constitutes a cross-sectional side view marked in FIG. 13B.

FIGS. 13B and 13D constitute a cross-sectional top view and a cross-sectional side view marked in FIG. 13B, respectively, of longitudinal string pull assemblies 120$^d$a and 120$^d$b in a first position, defined as a position in which both tooling interface 126$^e$a and tooling interface 126$^e$b are in contact with front panel 110$^d$. A rotation tool 76 can be engaged with either tooling interface 126$^e$ (bot shown), used to rotate it, thereby distancing tooling interface 126$^e$ away from front panel 110$^d$, and distancing movable element 122$^d$ away from adaptor member 136.

FIGS. 13A and 13C constitute a view in perspective and a cross-sectional top view, respectively, of longitudinal string pull assemblies 120$^d$a and 120$^d$b in a second position, defined as a position in which both tooling interfaces 126$^e$a and 126$^e$b are spaced from front panel 110$^d$, and both corresponding movable elements 122$^d$a and 122$^d$b are spaced father away from adaptor member 136, relative to the first position. Consequently, strings 128a and 128b, affixed at one end to movable element 122$^d$a and 122$^d$b, respectively, are pulled during the disposition of movable element 122$^d$a and 122$^d$b from the first to the second position, such that the string engagement portion 130 moves vertically towards proximal plate 106$^c$ from first position to second position.

According to some embodiments, the at least one string pull assembly 120 is rotateably attached to adaptor member 136. Reference is now made to FIGS. 15A-16B, depicting different embodiments of string pull assemblies 120 rotateably attached to adaptor member 136 having a mounting bore 138. According to some embodiments, at least one end of at least one string pull assembly 120 is rotateably attached to adaptor member 136, such that at least one tooling interface 126 extends through a sidewall (not numbered) of adaptor member 136. According to some embodiments, both ends of at least one string pull assembly 120 are rotateably attached to adaptor member 136, such that at least one tooling interface 126 extends through a sidewall (not numbered) of adaptor member 136.

Figure 14A:
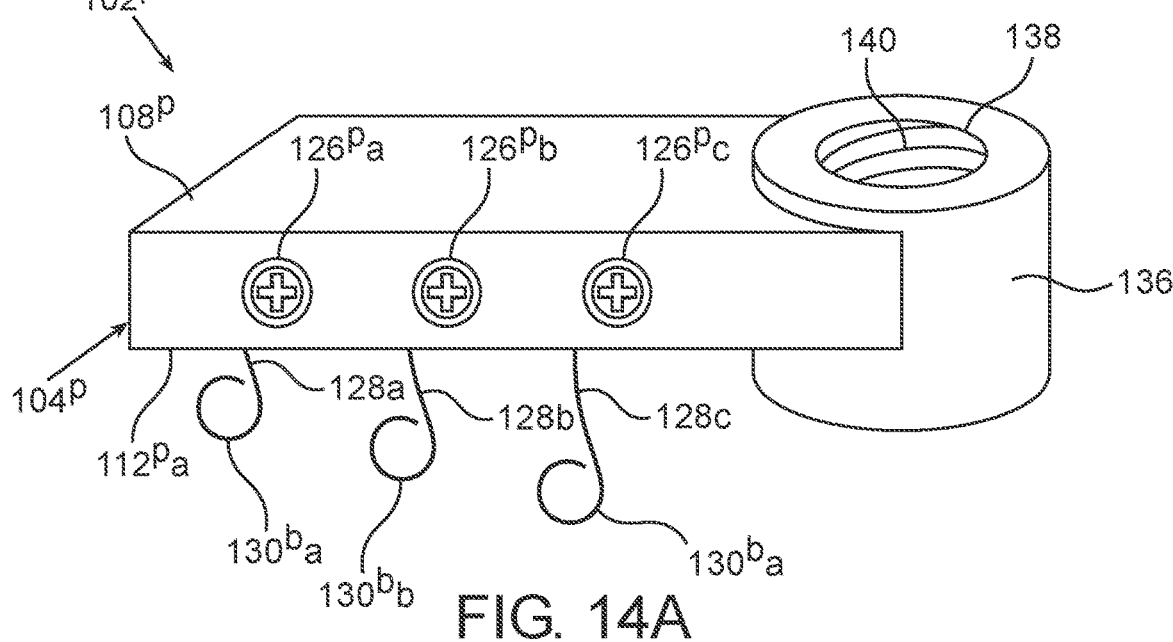
FIG. 14A constitutes a view in perspective of a distraction device having threaded channels, according to some embodiments.
Figure 14B:
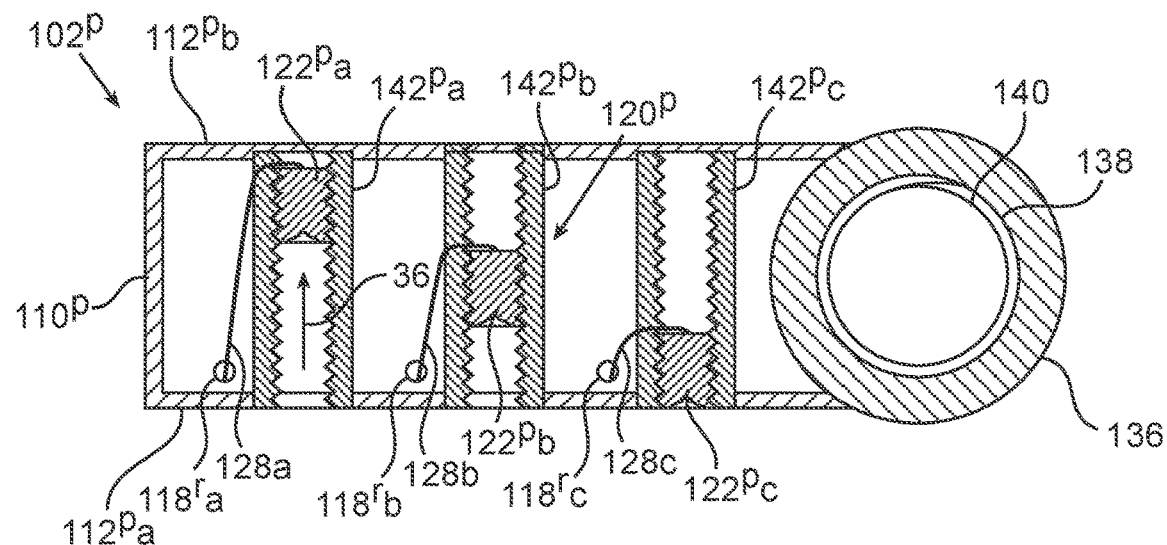
FIG. 14B constitutes a cross-sectional top view of the distraction device of FIG. 14A.

Reference now is made to FIGS. 14A-H, depicting different embodiments of string pull assemblies 120. FIGS. 14A and 14B constitute a view in perspective and a cross-sectional top view of a distraction device 100$^p$ comprising a plurality of string pull assemblies 120$^p$. In the embodiments depicted in FIGS. 14A-B, three string pull assemblies 120$^p$ are attached to a strings positioning member 104$^p$ of main body 102$^p$. According to some embodiments, string positioning member 104$^p$ comprises a distal panel 108$^p$, shown in FIG. 14A.

According to some embodiments, string pull assemblies 120 comprises a channel, such that the movable element 122 is configured to axially move along at least one direction within the channel 120.

According to some embodiments, string pull assemblies 120$^p$ comprises a channel 142$^p$, having a threading along at least a portion of its length, corresponding to a screw threading of movable element 122$^p$ formed as an inner screw, configured to enable longitudinal movement of movable element 122$^p$ along channel 142$^p$. According to some embodiments, movable element 122$^p$ formed as an inner screw is threadedly engaged with channel 142$^p$.

According to some embodiments, channel 142$^p$ has a fully closed circular profile along a plane perpendicular to its length, provided with a thread there along.

According to some embodiments, a sidewall, such as first sidewall 112$^d$a, comprises at least one opening to allow access to tooling interface 126$^p$ of movable element 122$^p$. String 128 is affixed at first string end to movable element 122$^p$, such that axial displacement of movable element 122$^p$ is configured to drag the string 128 in the same direction, without wrapping the string 128 around the movable element 122$^p$ it is attached to.

According to some embodiments, movable element 122$^p$ further comprises an inner core connected to an outer shell of the movable element 122$^p$ via a bearing, in order to allow axial displacement of a string 128 attached to the movable element 122$^p$ without being wrapped there around during rotational movement of the movable element 122$^p$ (embodiments not shown).

According to some embodiments, string positioning member 104 comprises a plurality of positioning features 118, for example formed as apertures, through which string 128 are configured to extend, such that the positioning features 118 are closer to one sidewall of string positioning member 104 than the opposite sidewall String positioning member 104$^p$ comprises a plurality of positioning features 118$^p$, for example formed as apertures, through which string 128 are configured to extend. According to some embodiments, the positioning features 118$^p$ are closer to a first sidewall 112$^p$a than the second sidewall 112$^p$b (see FIG. 14B).

In use, rotation of movable element 122$^p$ formed as an inner screw, in one direction, for example by rotation tool 76, leads the movable element 122$^p$ along channel 142$^p$ in direction 36 (the direction from the first sidewall 112$^p$a to the second sidewall 112$^p$b). The first string end of string 128 is axially displace along with movable element 122$^p$ in direction 36, in a manner that retracts the string engagement portion 130, such as the open ended string engagement portion 130$^b$, in the distal direction.

FIGS. 14A-B show an exemplary embodiment of the string pull assemblies 120$^p$, wherein each movable element $122^p a$, $122^p b$ and $122^p c$ is positioned at a different position along channel $142^p a$, $142^p b$ and $142^p c$, corresponding to a different position of string engagement portion $130^b a$, $130^b b$ and $130^b c$ of FIG. 14A, respectively.

According to some embodiments, distal panel 108 comprises at least one viewing window 117, overlaying the position of channel 142, configured to enable a user of the distraction device $100^p$ to see the position of movable element 122 within channel 142. According to some embodiments, the at least one viewing window 117 is formed as an opening in distal panel 108. According to some embodiments, the at least one viewing window 117 comprises a transparent material.

Figure 14C:
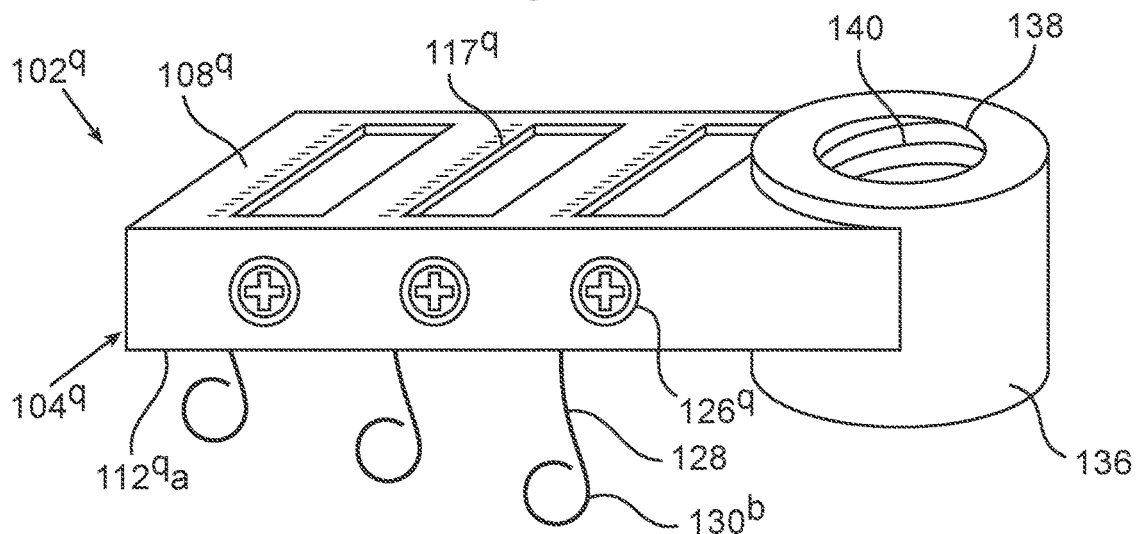
FIG. 14C constitutes a view in perspective of a distraction device having windows overlaid over threaded channels, according to some embodiments.
Figure 14D:
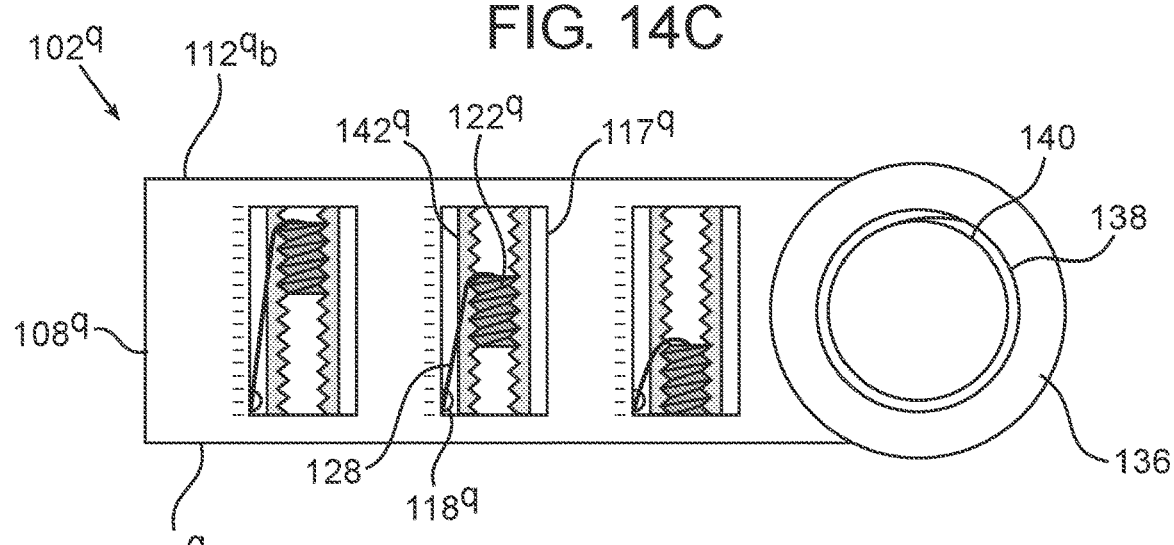
FIG. 14D constitutes a top view of the distraction device of FIG. 14C.

FIGS. 14C and 14D constitute a view in perspective and a top view of a distraction device $100^q$ comprising a plurality of string pull assemblies $120^q$. In the embodiments depicted in FIGS. 14C-D, three string pull assemblies $120^q$ are attached to a strings positioning member $104^q$ of main body $102^q$.

According to some embodiments, string positioning member $104^p$ comprises a distal panel $108^q$, shown in FIG. 14C but removed from view in FIG. 14D in order to expose the inner components housed within string positioning member $104^q$. According to some embodiments, distal panel $108^q$ comprises at least one viewing window $117^q$, overlaying the position of a respective channel $142^q$, configured to enable a user of the distraction device $100^q$ to see the position of movable element $122^q$ within channel $142^q$.

According to some embodiments, the at least one viewing window $117^q$ comprises markings, such as graduation marks, indicating the position of the movable element $122^q$. According to some embodiments, distal panel $108^q$ comprises markings, such as graduation marks, adjacent to the at least one viewing window $117^q$.

According to some embodiments, other regions of strings positioning member 104 comprise at least one viewing window, to allow viewing current position of movable element 122, such as sidewalls 112a and 112b or front panel 110 (embodiments now shown).

According to some embodiments, string pull assemblies $120^q$ comprises a channel $142^q$, having a threading along at least a portion of its length, corresponding to a screw threading of movable element $122^q$ formed as an inner screw, configured to enable longitudinal movement of movable element $122^q$ along channel $142^q$. According to some embodiments, movable element $122^q$ formed as an inner screw is threadedly engaged with channel $142^q$.

According to some embodiments, channel $142^q$ has a partially open circular profile along a plane perpendicular to its length, extending along less than 360 degrees, such that a slot is formed along a distal portion thereof. The position of movable element $122^q$ within channel $142^q$, as seen through viewing window $117^q$, can be visible through the slot disposed axially in direction 36 at the distal portion of channel $142^q$.

Figure 14E:
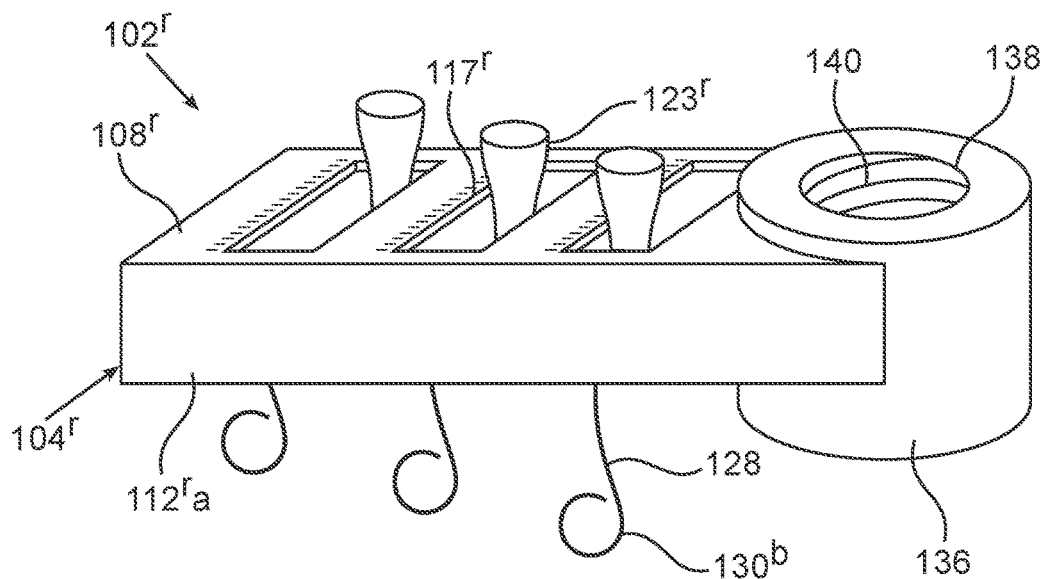
FIG. 14E constitutes a view in perspective of a distraction device having ratcheting channels, according to some embodiments.
Figure 14F:
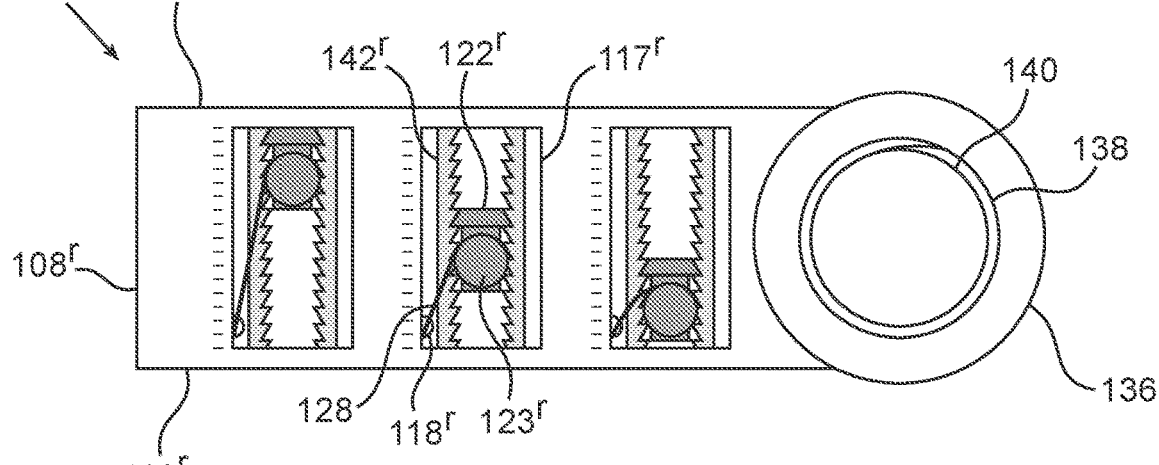
FIG. 14F constitutes a top view of the distraction device of FIG. 14E.

FIGS. 14E and 14F constitute a view in perspective and a top view of a distraction device $100^r$ comprising a plurality of string pull assemblies $120^r$. In the embodiments depicted in FIGS. 14C-D, three string pull assemblies $120^r$ are attached to a strings positioning member $104^r$ of main body $102^r$.

According to some embodiments, string positioning member $104^r$ comprises a distal panel $108^r$, shown in FIG. 14E but removed from view in FIG. 14F in order to expose the inner components housed within string positioning member $104^r$.

According to some embodiments, string pull assemblies $120^r$ comprises a channel $142^r$, having ratcheting teeth along at least a portion of its length, corresponding to at least one complementary ratcheting tooth or pawl of movable element $122^r$ formed as ratcheting element, configured to enable longitudinal one-directional movement of movable element $122^r$ along channel $142^r$.

According to some embodiments, movable element 122 further comprises an extension 123, configured to allow grasping thereof, either by hand or by a tool. Extension 123 is configured to allow axial displacement of movable element 122 by pushing or moving the extension 123 in a desired direction, to a desired new position.

According to some embodiments, movable element $122^r$ further comprises an extension $123^r$ in the form of a vertical extension (see FIGS. 14E-F). According to some embodiments, distal panel $108^q$ comprises at least one window $117^r$, overlaying the position of a respective channel $142^r$.

According to some embodiments, window $117^r$ is configured to enable extension $123^q$ to extend there through (for example, in the vertical direction), and move there along, for example in direction 36. According to some embodiments, distal panel $108^q$ comprises markings, such as graduation marks, adjacent to the at least one window $117^r$.

String 128 is affixed at first string end to movable element $122^r$, such that axial displacement of movable element $122^r$ is configured to drag the string 128 in the same direction, without wrapping the string 128 around the movable element $122^r$ it is attached to.

According to some embodiments, movable element $122^r$ further comprises an inner core connected to an outer shell of the movable element $122^r$ via a bearing, in order to allow axial displacement of a string 128 attached to the movable element $122^r$ without being wrapped there around during rotational movement of the movable element $122^r$ (embodiments not shown).

String positioning member $104^q$ comprises a plurality of positioning features $118^r$, for example formed as apertures, through which string 128 are configured to extend. According to some embodiments, the positioning features $118^r$ are closer to a first sidewall $112^r a$ than the second sidewall $112^r b$ (see FIG. 14F).

In use, axial displacement of movable element $122^r$ formed as ratcheting element, for example by grasping extension $123^r$ and pushing it in direction 36, results in axial displacement of the first string end of string 128 there along, in a manner that pulls the string engagement portion 130 at the second string end in the distal direction.

FIGS. 14E-F show an exemplary embodiment of string pull assemblies $120^r$, wherein each movable element $122^r$ is positioned at a different position along its respective channel $142^r$, similar to the positions exemplified in FIGS. 14A-B.

Figure 14G:
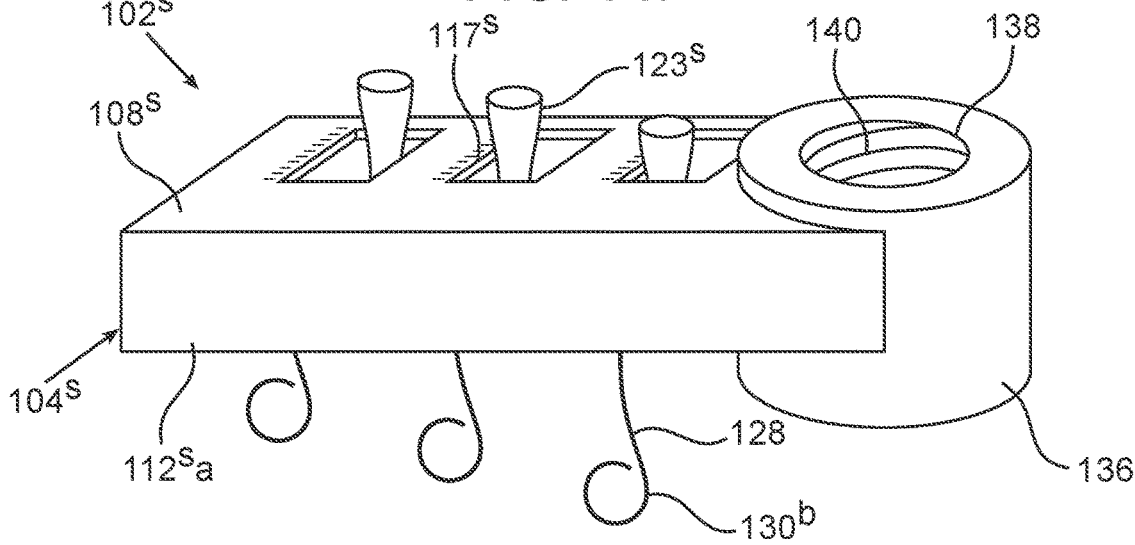
FIG. 14G constitutes a view in perspective of a distraction device having ratcheting channels, according to some embodiments.
Figure 14H:
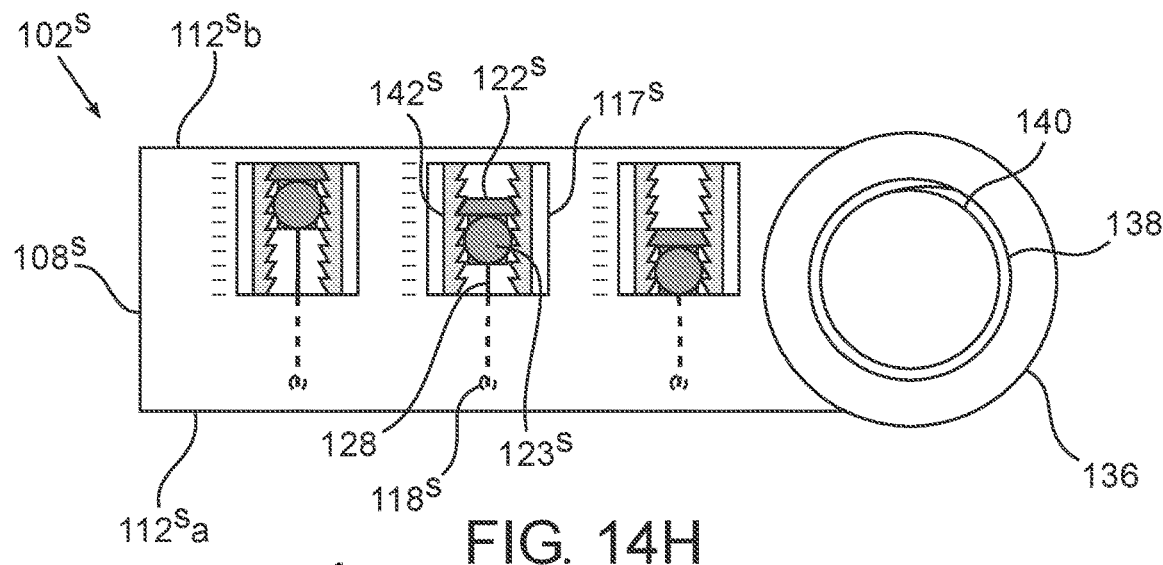
FIG. 14H constitutes a top view of the distraction device of FIG. 14G.

FIGS. 14G and 14H constitute a view in perspective and a top view of a distraction device $100^r$ comprising a plurality of string pull assemblies $120^s$. Distraction device $100^s$, along with all of its internal components, are similar in structure and function to the embodiments of distraction device main body $102^r$ and its respective components, as described herein and shown in FIGS. 14E-F, except that the channels $142^s$, and potentially windows $117^s$, extend longitudinally along a shorter path than channels $142^r$, and that the positioning features $118^s$ are positioned at different positions along the proximal panel $106^s$, for example evenly spaced from both sidewalls $112^s a$ and $112^s b$.

According to some embodiments, string pull assembly 120 comprises a pump, and movable element 122 is formed as a piston configured to move within the pump (embodiments not shown).

According to some embodiments, string pull assembly 120 comprises a spring, and movable element 122 is configured to axially displace against the force of the spring (embodiments not shown).

According to some embodiments, movement of movable element 122, including rotational and axial movement, is facilitated by manual force application, such as gripping an extension 123 and moving it in an axial direction, or rotating movable element 122 via rotation tool 76.

According to some embodiments, movement of movable element 122, including rotational and axial movement, is facilitated by electronic control means.

Figure 15A:
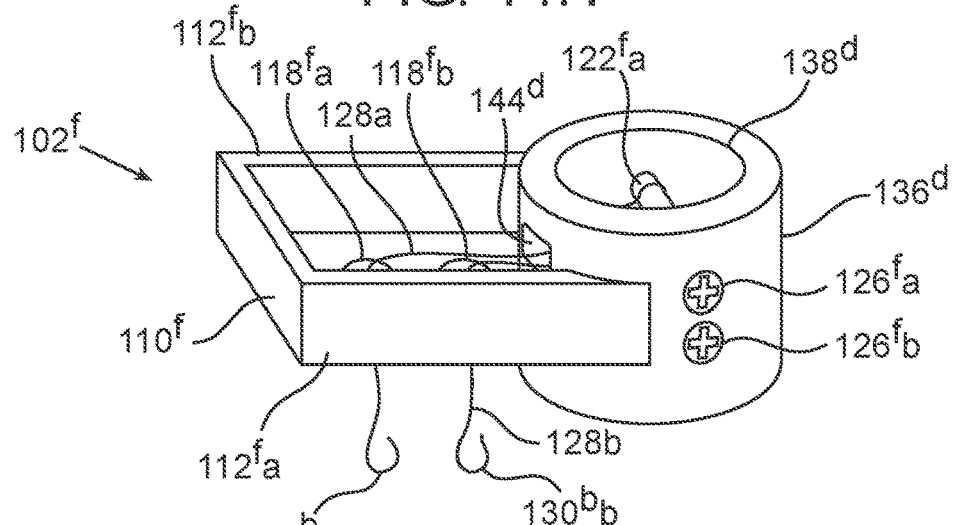
FIG. 15A constitutes a view in perspective of a distraction device having two string pull assemblies positioned within an adaptor boy, according to some embodiments.
Figure 15B:
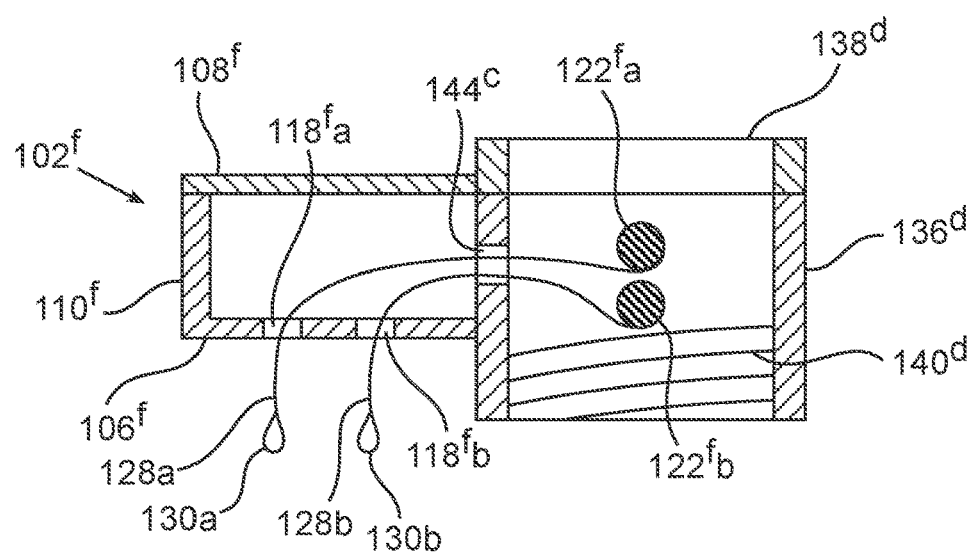
FIG. 15B constitutes a cross-sectional side view of the distraction device of FIG. 15A.

FIGS. 15A and 15B constitute a view in perspective and a cross-sectional side view, respectively, of a distraction device $100^f$ having two exemplary string pull assemblies $120^f$ disposed within adaptor member $136^d$. Adaptor member $136^d$ comprises mounting bore $138^d$, within which two string pull assemblies $120^f$a and $120^f$b are disposed, each of which are attached at both ends thereof to the sidewall of adaptor member $136^d$. Each string pull assembly $120^f$ comprises a movable element $122^f$ formed as a shaft, a string 128 affixed to movable element $122^f$ and extending through an adaptor aperture $144^d$ of adaptor member $136^d$ towards positioning feature $118^f$ formed as an aperture within proximal panel $106^f$, and a tooling interface $126^f$, extending through a sidewall of adaptor member $136^d$. According to some embodiments, string pull assemblies $120^f$a and $120^f$b are vertically aligned in parallel to each other. According to some embodiments, bore screw thread $140^d$ extends along a proximal portion of the vertical length of mounting bore $138^d$, such that it does not cross the region of contact between the most proximal movable element $122^f$b and mounting bore $138^d$.

Figure 16A:
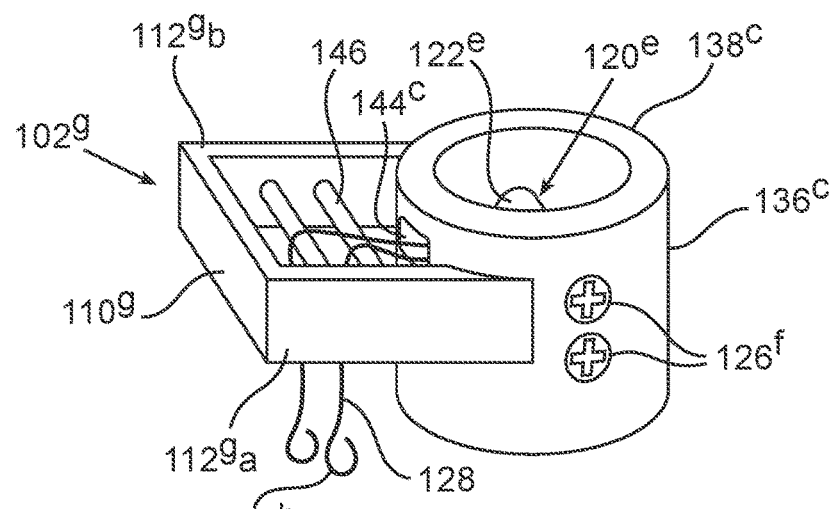
FIG. 16A constitutes a view in perspective of a distraction device having two string pull assemblies positioned within an adaptor body, and a two support rods position within a strings positioning member, according to some embodiments.
Figure 16B:
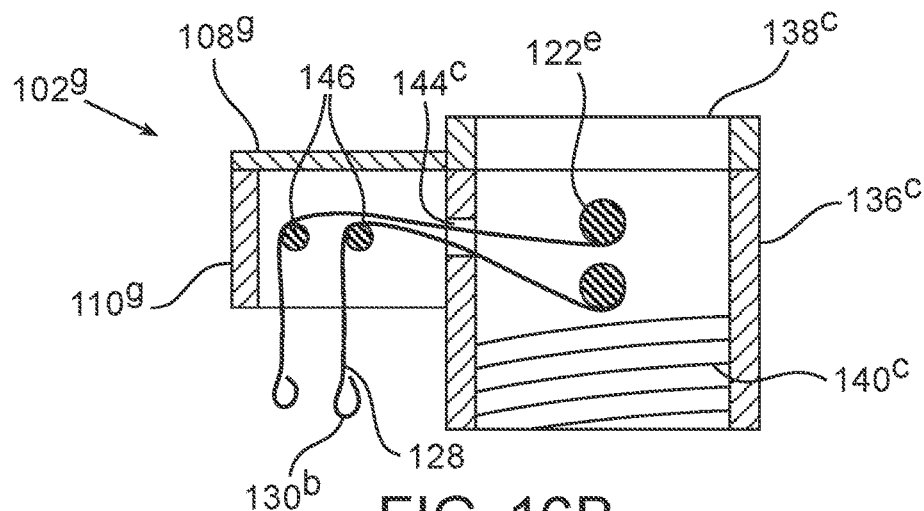
FIG. 16B constitutes a cross-sectional side view of the distraction device of FIG. 16A.

FIGS. 16A and 16B constitute a view in perspective and a cross-sectional side view, respectively, of a distraction device $100^g$ having two exemplary single string pull assemblies $120^f$ of FIGS. 15A and 15B, and at least one support rod 146 positioned within and attached to string positioning member $104^g$. In the exemplary embodiments of FIGS. 16A-16B, positioning features 118 are formed as the contact point between the strings 128 and the support rods 146. Specifically, each support rod 146 is configured to direct a corresponding string's 128 path, passing through adaptor aperture 144, over the support rod 146 and towards the jaw when in use. According to some embodiments, each support rod 146 is attached at both ends to sidewalls $112^g$.

According to some embodiments, adaptor member 136 is fittable to any implant abutment 150 as is known in the art. According to some embodiments, a distraction system 200 is a system comprising at least a distraction device 100, and an abutment 150 configured to be associated with the at least one connection platform of the adaptor member 136 of the distraction device 100.

Figure 29A:
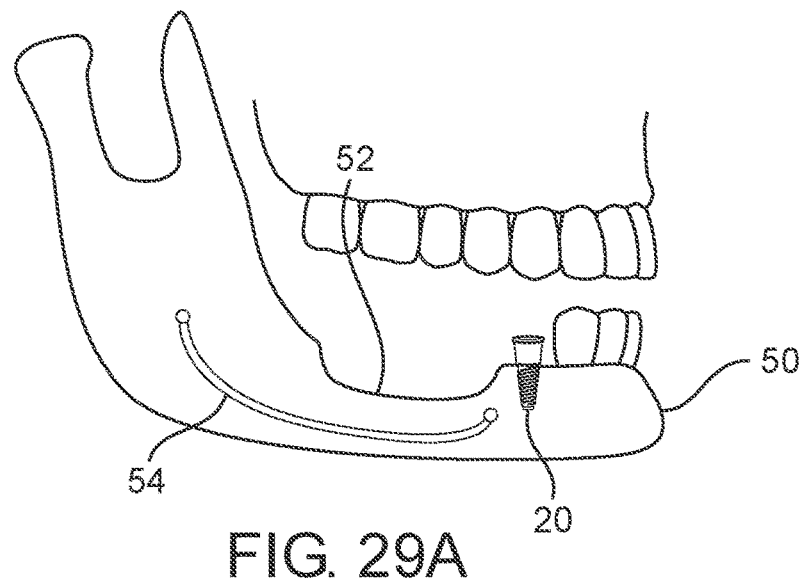
FIG. 29A constitutes a side view of the mandible, with a bone screw positioned adjacent to an alveolar ridge, according to some embodiments.
Figure 29B:
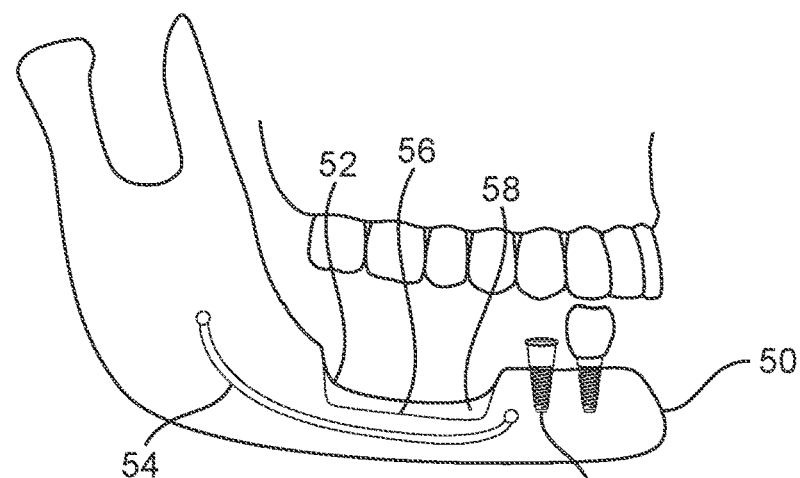
FIG. 29B constitutes a side view of the mandible of FIG. 29A, with a crestal osteotomy line formed therein, according to some embodiments.
Figure 29C:
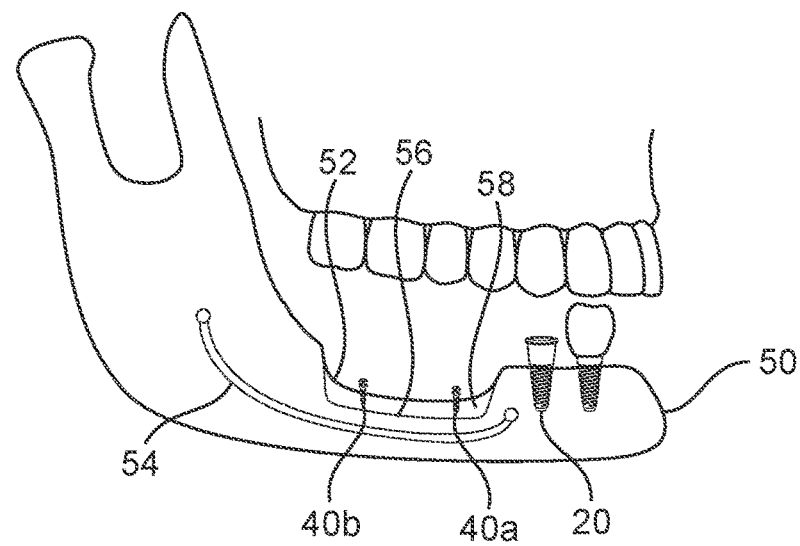
FIG. 29C constitutes a side view of miniscrews inserted into an osteotomized bone segment of the mandible of FIG. 29B, according to some embodiments.
Figure 29D:
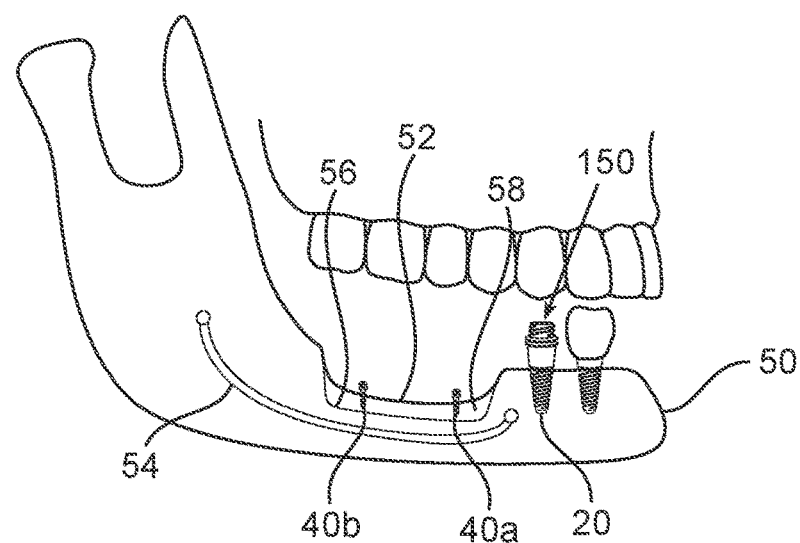
FIG. 29D constitutes a side view of an abutment engaged with the miniscrews of FIG. 29A, according to some embodiments.
Figure 29E:
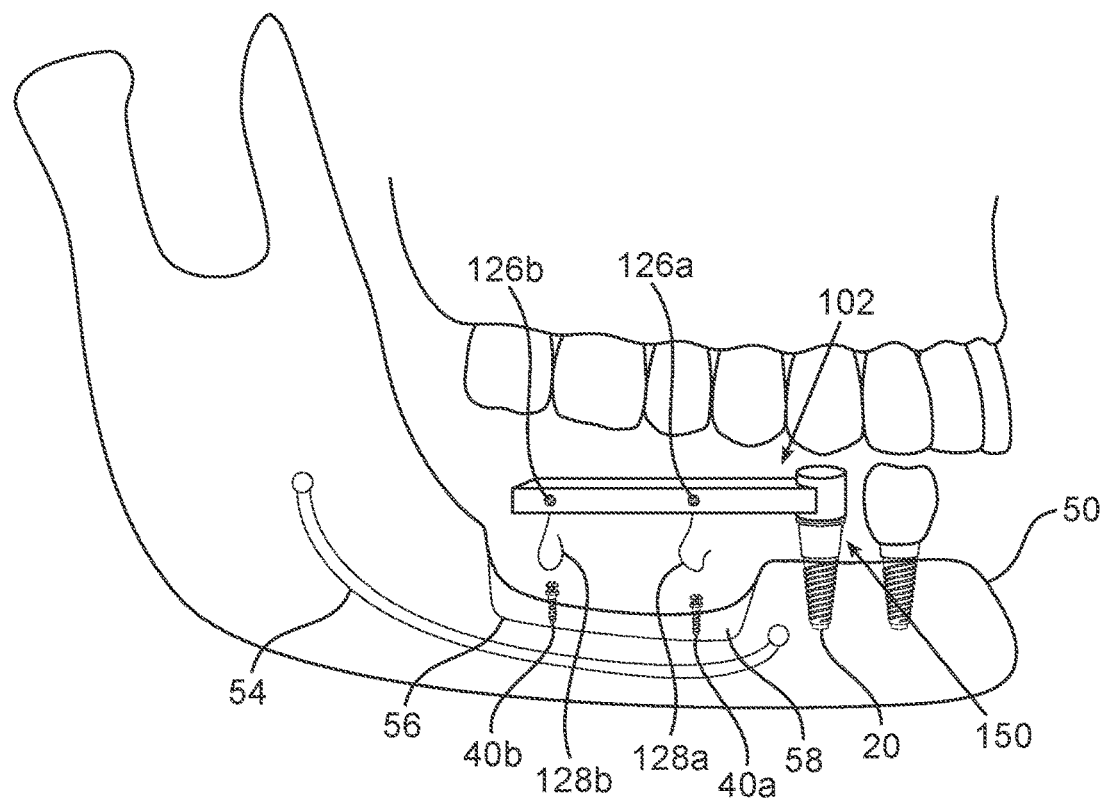
FIG. 29E constitutes a side view of the distraction device engaged with the abutment of FIG. 29D, according to some embodiments.

According to some embodiments, the at least one connection platform of adaptor member 136 is formed as a mounting socket (not numbered, see FIG. 29E for example). The main difference between a mounting socket and a mounting bore 138, is that mounting bore 138 is open-ended at both a proximal and a distal end thereof, while a mounting socket is open-ended only at the proximal end thereof. Otherwise, the mounting socket can include any of the other features or components described throughout the specification for all embodiments of mounting bore 138, such as being formed with internal threading, being formed with internal polygonal facets and the like, and not described here for the sake of brevity.

Figure 17A:
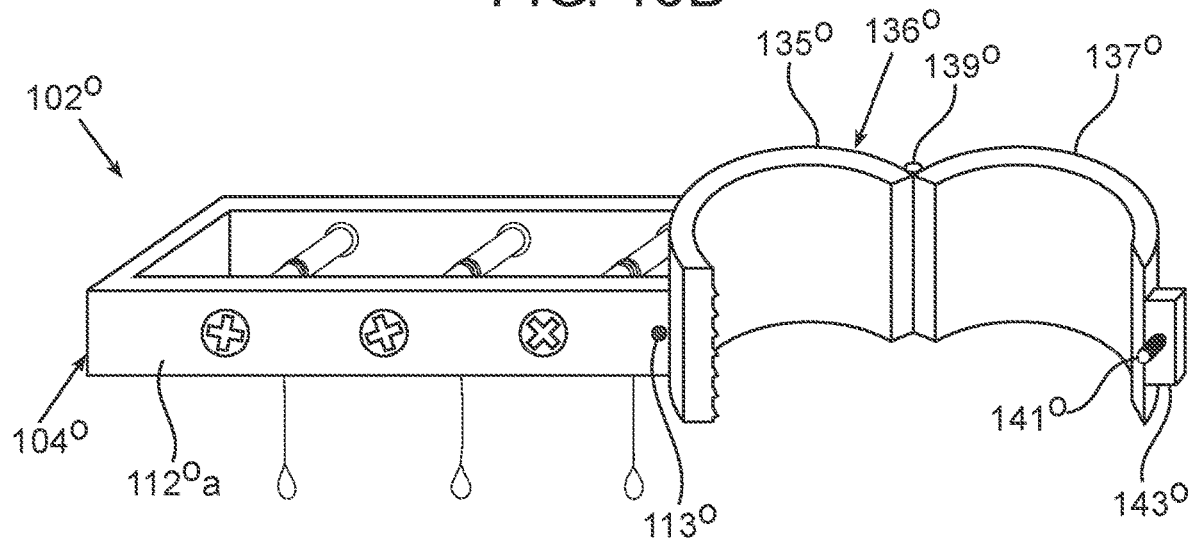
FIG. 17A constitutes a view in perspective of a distraction device having an adaptor member in a loose state, according to some embodiments.
Figure 17B:
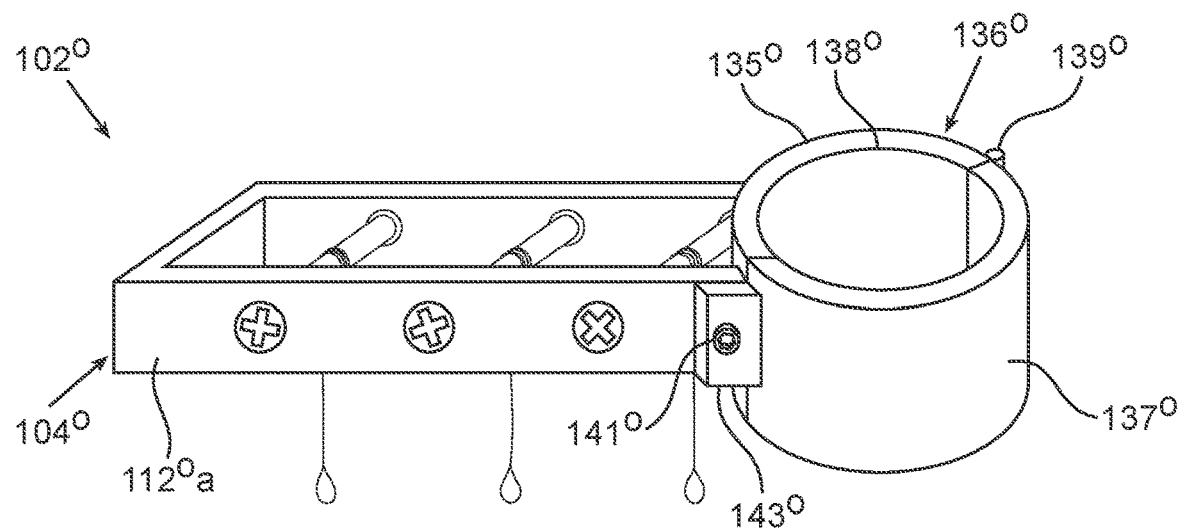
FIG. 17B constitutes a view in perspective of the distraction device of FIG. 17A in a tight state.
Figure 17C:
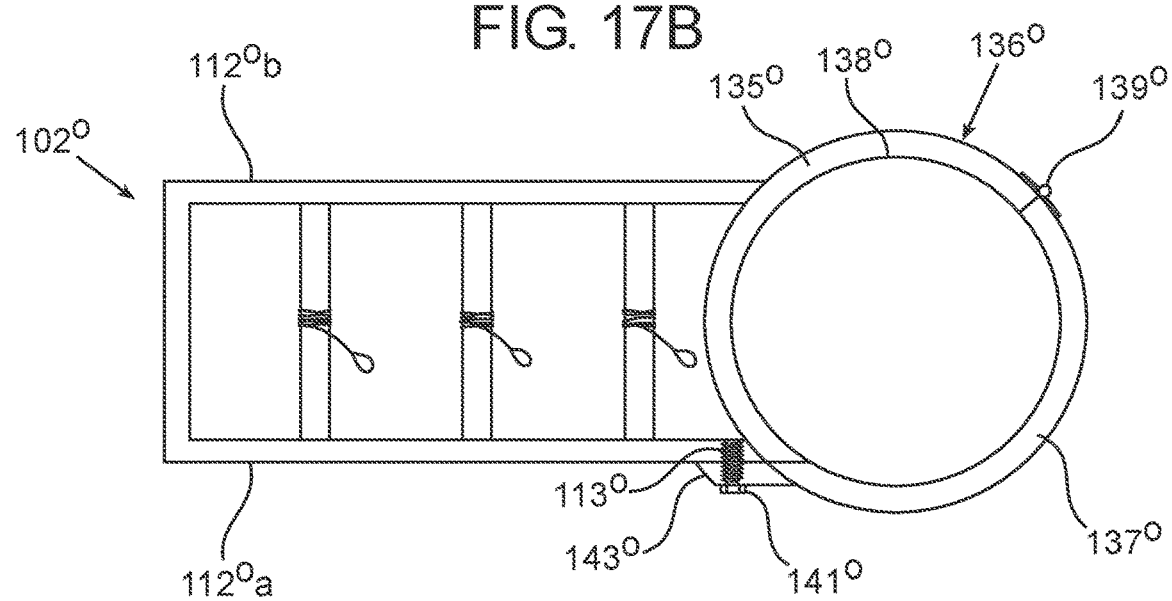
FIG. 17C constitutes a top view of the distraction device of FIG. 17B in a tight state.

Reference now is made to FIGS. 17A-G, depicting different embodiments of adaptor member 136. FIGS. 17A and 17B constitute views in perspective of a distraction device $100^o$ comprising an adaptor member $136^o$ in a loose and tight states, respectively. FIG. 17C constitutes a top view of distraction device $100^o$ in a tight state.

Adaptor member $136^t$ is formed as a hinged ring, having a stationary ring portion $135^o$ and a dynamic ring portion $137^o$ hinged thereto via hinge $139^o$ at its hinged end, and detachably attachable to the main body $102^o$ at its opposite dynamic end equipped with tightening mechanism $143^o$.

FIG. 17A shows the adaptor member $136^o$ in a loose state, defined as a state in which the dynamic end having the tightening mechanism $143^o$ is detached from the main body $102^o$.

FIGS. 17B-C show the adaptor member $136^o$ in a tight state, defined as a state in which the dynamic end having the tightening mechanism $143^o$ is attached to the main body $102^o$, such that the static ring portion $135^o$ and the dynamic ring portion $137^o$ together form central bore $138^o$.

According to some embodiments, the tightening mechanism $143^o$ is configured to attach to adaptor member $136^o$, for example to an end of static ring portion 135 opposite to the hinge 139.

According to some embodiments, the tightening mechanism $143^o$ is configured to attach to string positioning member $104^o$, for example a sidewall $112^o$ at a position adjacent to its connection to adaptor body $136^o$.

According to some embodiments, the dynamic end of the dynamic portion $137^o$ is detachably attachable to the main body $102^o$ via tightening member $141^o$, such as a screw (exemplified in FIGS. 17A-C) configured to screw through the tightening mechanism $143^o$ into a screw-bore $113^o$ of sidewall $112^o$a.

According to some embodiments, the dynamic end of the dynamic portion 137 is detachably attachable to the main body 102 via According to some embodiments, the dynamic end of the dynamic portion $137^o$ is detachably attachable to the main body $102^o$ via attachment means $143^o$ comprising a snap-fit (not shown) or other attachment means known in the art.

According to some embodiments, the tightening mechanism $143^o$ is configured to adjust the diameter of central bore $138^o$. Advantageously, tightening member $141^o$ comprising a screw enable adjusting the degree of tightening of adaptor body $136^o$, essentially by adjusting the diameter of central bore $138^o$.

Figure 17D:
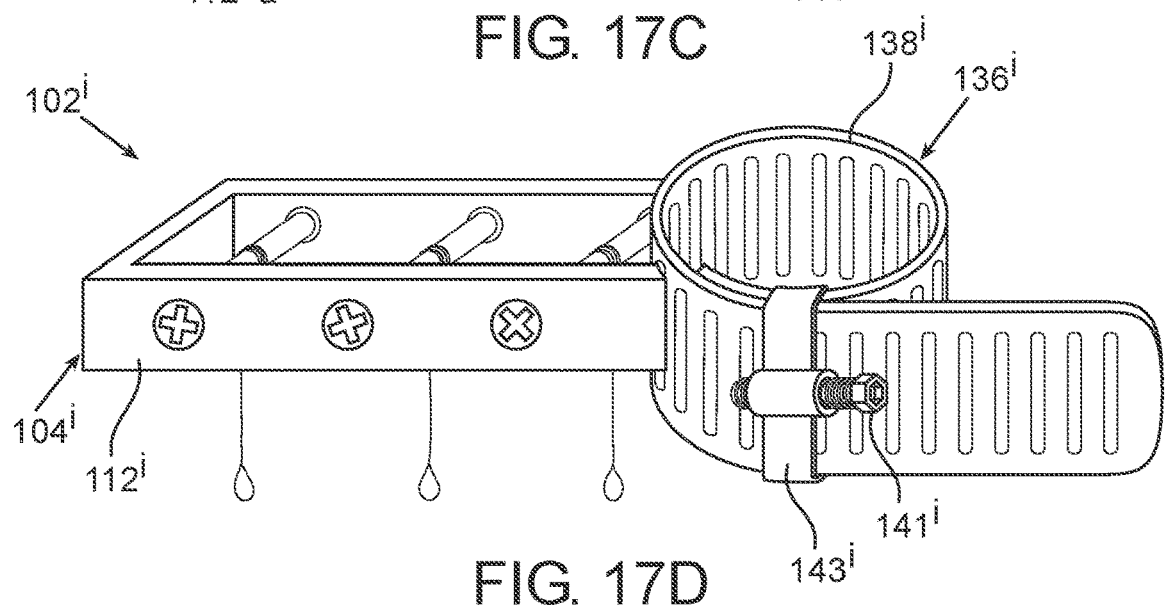
FIG. 17D constitutes a view in perspective of a distraction device having an adaptor member formed as a ring clamp, according to some embodiments.
Figure 17E:
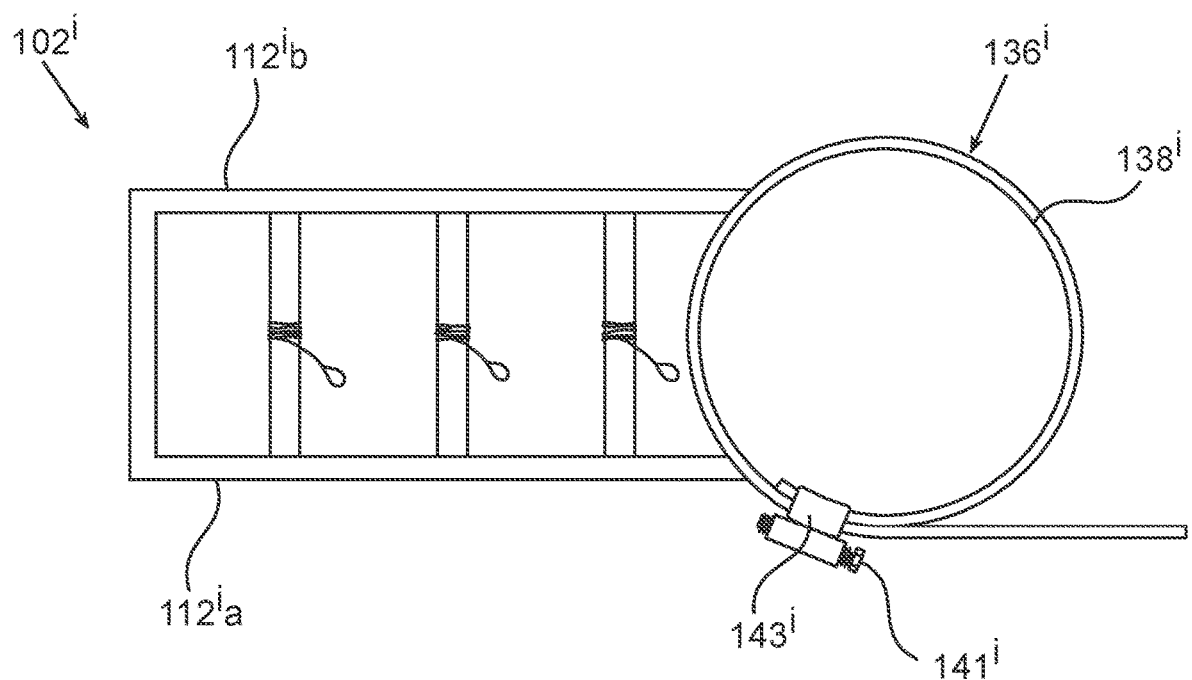
FIG. 17E constitutes a top view of the distraction device of FIG. 17D.

FIGS. 17D and 17E constitute a view in perspective and a top view, respectively, of a distraction device $100^i$ comprising an adaptor member $136^i$, according to some embodiments. Adaptor member $136^i$ is formed as ring clamp having a tightening mechanism $143^i$ comprising a tightening member $141^i$, for example in the form of a screw (see FIGS. 17D-E). According to some embodiments, the tightening mechanism $143^i$ is configured to adjust the diameter of central bore $138^i$.

According to some embodiments, at least one end of adaptor member $136^i$ is configured for advancement through a respective receiving portion of tightening mechanism $143^i$, wherein tightening member $141^i$ can affix the position of both ends of the adaptor member $136^i$ relative to each other, thereby retaining central bore $138^i$ at a desired diameter.

Figure 17F:
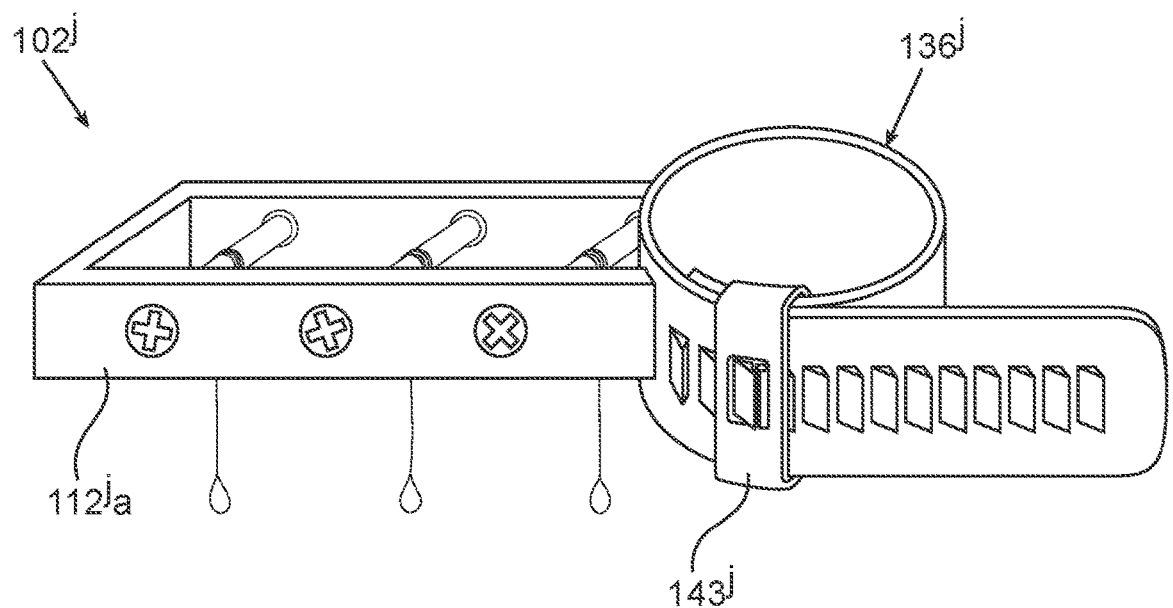
FIG. 17F constitutes a view in perspective of a distraction device having an adaptor member comprising a tongue configured for ratcheting engagement with a tightening mechanism, according to some embodiments.
Figure 17G:
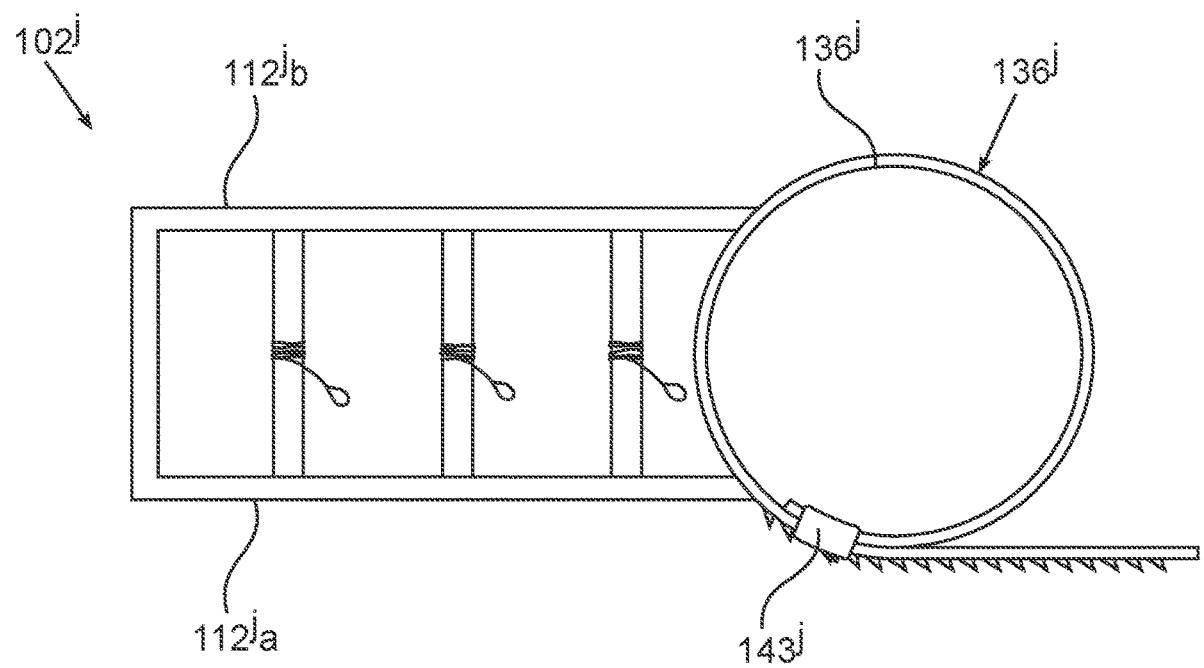
FIG. 17G constitutes a top view of the distraction device of FIG. 17F.

FIGS. 17F and 17G constitute views in perspective of a distraction device $100^j$ comprising an adaptor member $136^i$ in a loose and tight states, respectively. Adaptor member 136$^j$ is formed as an adjustable ring or clamp having a tightening mechanism 143$^j$.

According to some embodiments, dynamic end 143$^j$ comprises a tongue having ridges there along, configured for a ratcheting engagement with a receiving portion of tightening mechanism 143$^j$. According to some embodiments, the tightening mechanism 143$^j$ is configured to adjust the diameter of central bore 138$^j$.

According to some embodiments, adaptor member 136 is formed as ring clamp, wherein the tightening mechanism 143 comprises a pair of diametrically opposed jaws that are biased radially inwardly toward each other (embodiments not shown).

Figure 18A:
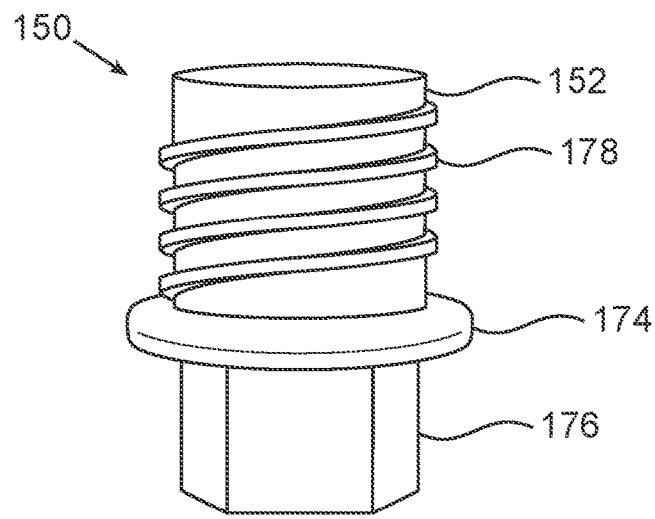
FIG. 18A constitutes a view in perspective of an abutment having a threaded cylindrical abutment distal portion, according to some embodiments.
Figure 18B:
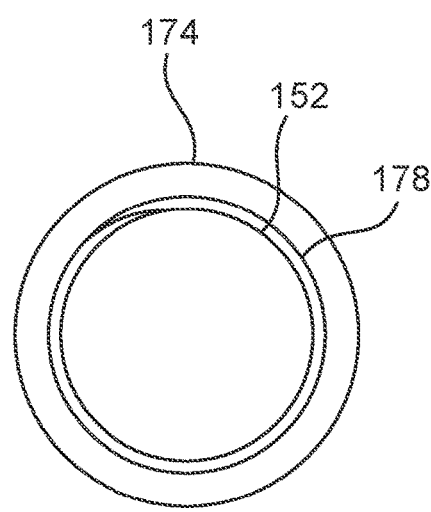
FIG. 18B constitutes a top view of the abutment of FIG. 18A.

Reference is now made to FIGS. 18A-18D, depicting different embodiments of abutment 150. FIGS. 18A and 18B constitute a view in perspective and a top view, respectively, of abutment 150, according to some embodiments. Abutment 150 comprises an abutment distal portion 152, an abutment proximal portion 176, and an abutment mid-portion 174 fluidly connected to abutment distal portion 152 and to abutment proximal portion 176. Abutment proximal portion 176 is configured to be inserted into a matching socket (not shown) of a bone screw 20. According to some embodiments, abutment proximal portion 176 comprises a screw thread (not illustrated), matching a screw thread of a bone screw 20. According to some embodiments, abutment proximal portion 176 comprises a polyhedral-shaped structure (see FIG. 18A), matching a similarly shaped structure within a bone screw 20. According to some embodiments, abutment distal portion 152 comprises an abutment distal portion screw thread 178, matching bore screw thread 140. According to some embodiments, the largest cross-sectional diameter of abutment mid-portion 174 is larger than any of the largest cross-sectional diameter of abutment distal portion 152, and the largest cross-sectional diameter of abutment proximal portion 176. According to some embodiments, abutment distal portion 152, abutment mid-portion 174 and abutment proximal portion 176 are integrally formed.

Figure 18C:
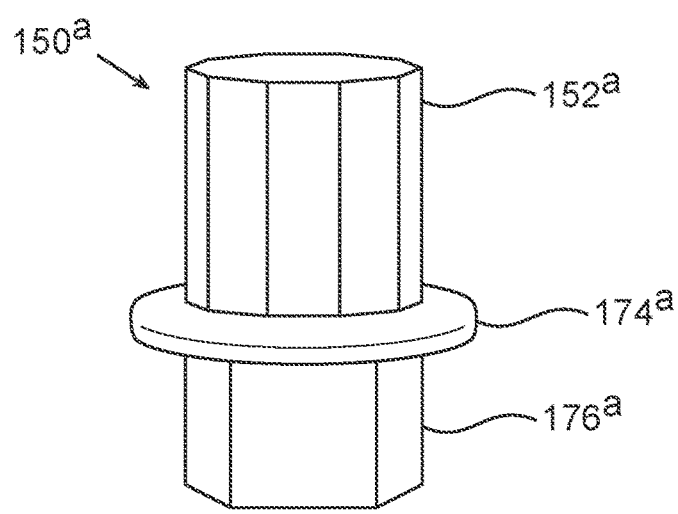
FIG. 18C constitutes a view in perspective of an abutment having a polygonal abutment distal portion, according to some embodiments.
Figure 18D:
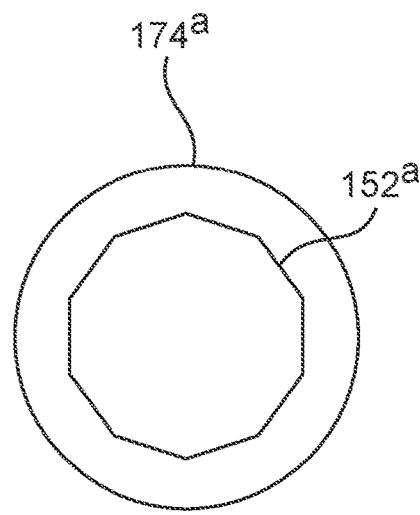
FIG. 18D constitutes a top view of the abutment of FIG. 18C.

FIGS. 18C and 18D constitute a view in perspective and a top view, respectively, of abutment 150$^a$, according to some embodiments. Abutment 150$^a$ comprises an abutment distal portion 152$^a$, abutment mid-portion 174$^a$ and abutment proximal portion 176$^a$. Abutment proximal portion 176$^a$ is configured to be inserted into a matching socket (not shown) of a bone screw 20. According to some embodiments, abutment proximal portion 176$^a$ comprises a polyhedral-shaped structure, such as a hexagon (see FIG. 18C), matching a similarly shaped structure within a bone screw 20. According to some embodiments, abutment distal portion 152 comprises a polyhedral-shaped structure, such as a decagon (see FIGS. 18C-18D), matching a similarly shaped, matching polyhedral-shaped mounting bore 138. According to some embodiments, the largest cross-sectional diameter of abutment mid-portion 174$^a$ is larger than either the largest cross-sectional diameter of abutment distal portion 152$^a$, or the largest cross-sectional diameter of abutment proximal portion 176$^a$. According to some embodiments, abutment distal portion 152$^a$, abutment mid-portion 174$^a$ and abutment proximal portion 176$^a$ are integrally formed.

According to some embodiments, abutment 150 further comprises a channel through which an internal screw can be inserted, to couple abutment 150 with a bone screw 20 having a threaded receiving channel for the internal screw.

According to some embodiments, adaptor member 136 comprises a mounting extension (not illustrated) instead of a mounting socket, which can be either threaded or shaped as a polyhedral extension, configured to be received within a matching socket of an abutment 150 or a bone screw 20.

Bone screw 20 is an implant provided with means (such as screw threads) to securely engage bone surfaces of a bone socket, such as a socket created in a jaw bone. According to some embodiments, bone screw 20 comprises any bone implant know in the art, configured to receive and securely engage with either abutment 150 or distraction device 100.

Figure 19A:
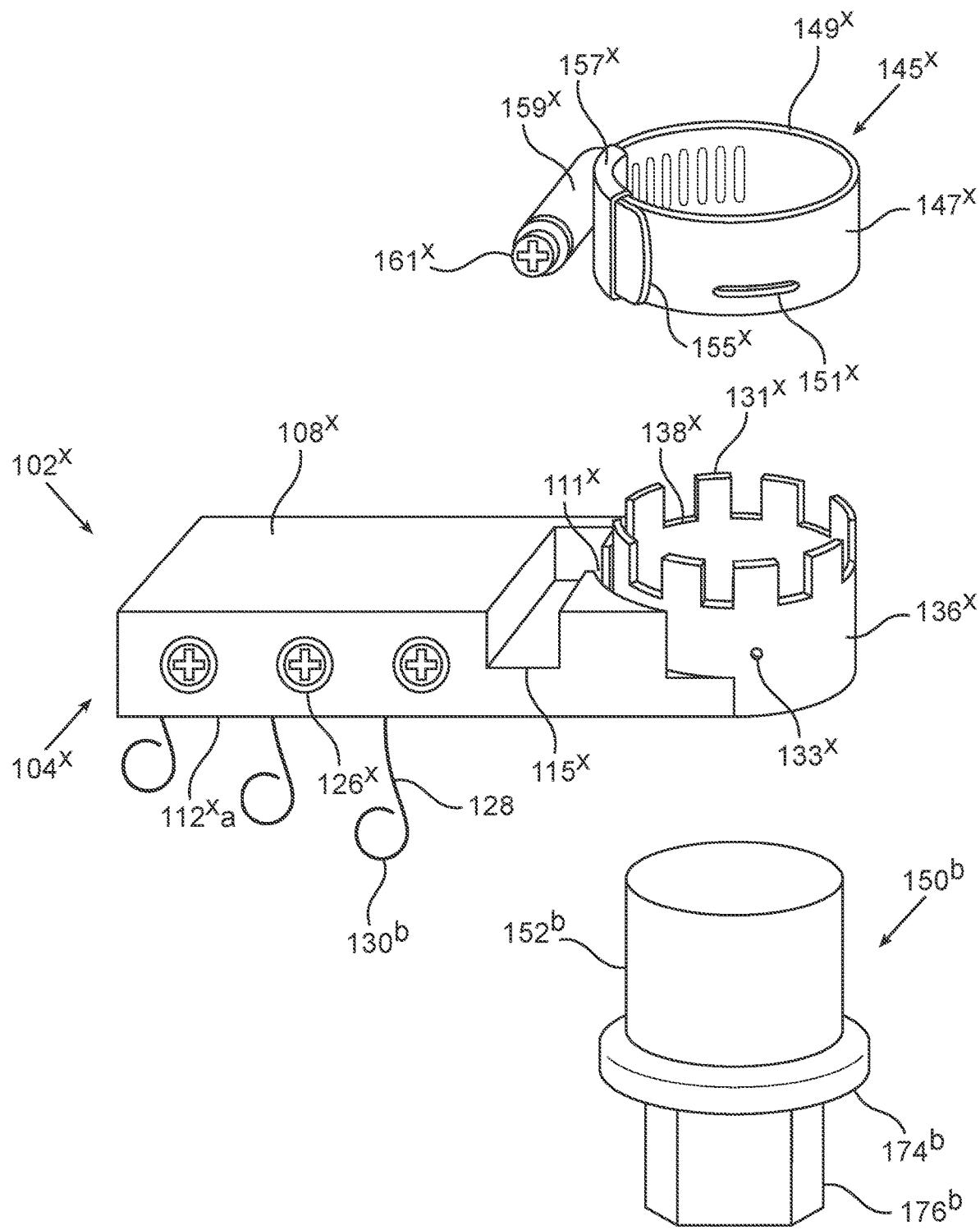
FIG. 19A constitutes an exploded view in perspective of a distraction assembly, according to some embodiments.
Figure 19B:
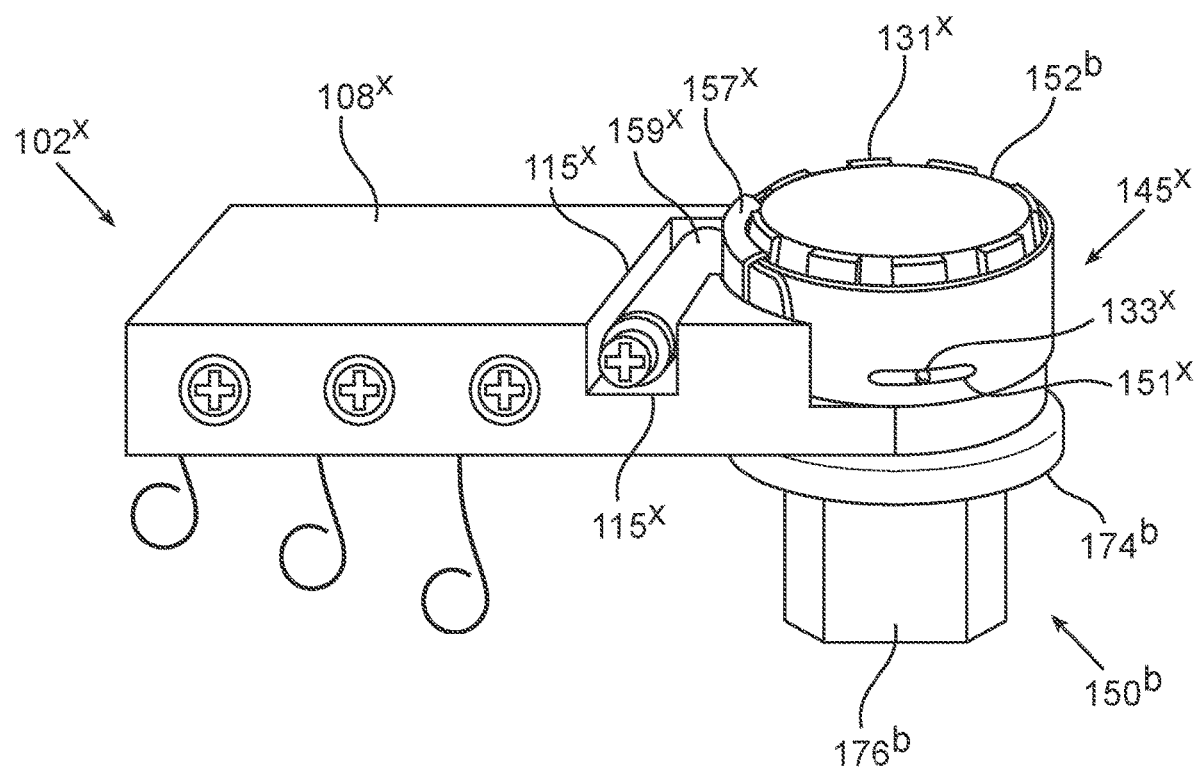
FIG. 19B constitutes a view in perspective of an assembled distraction assembly, according to some embodiments.
Figure 20A:
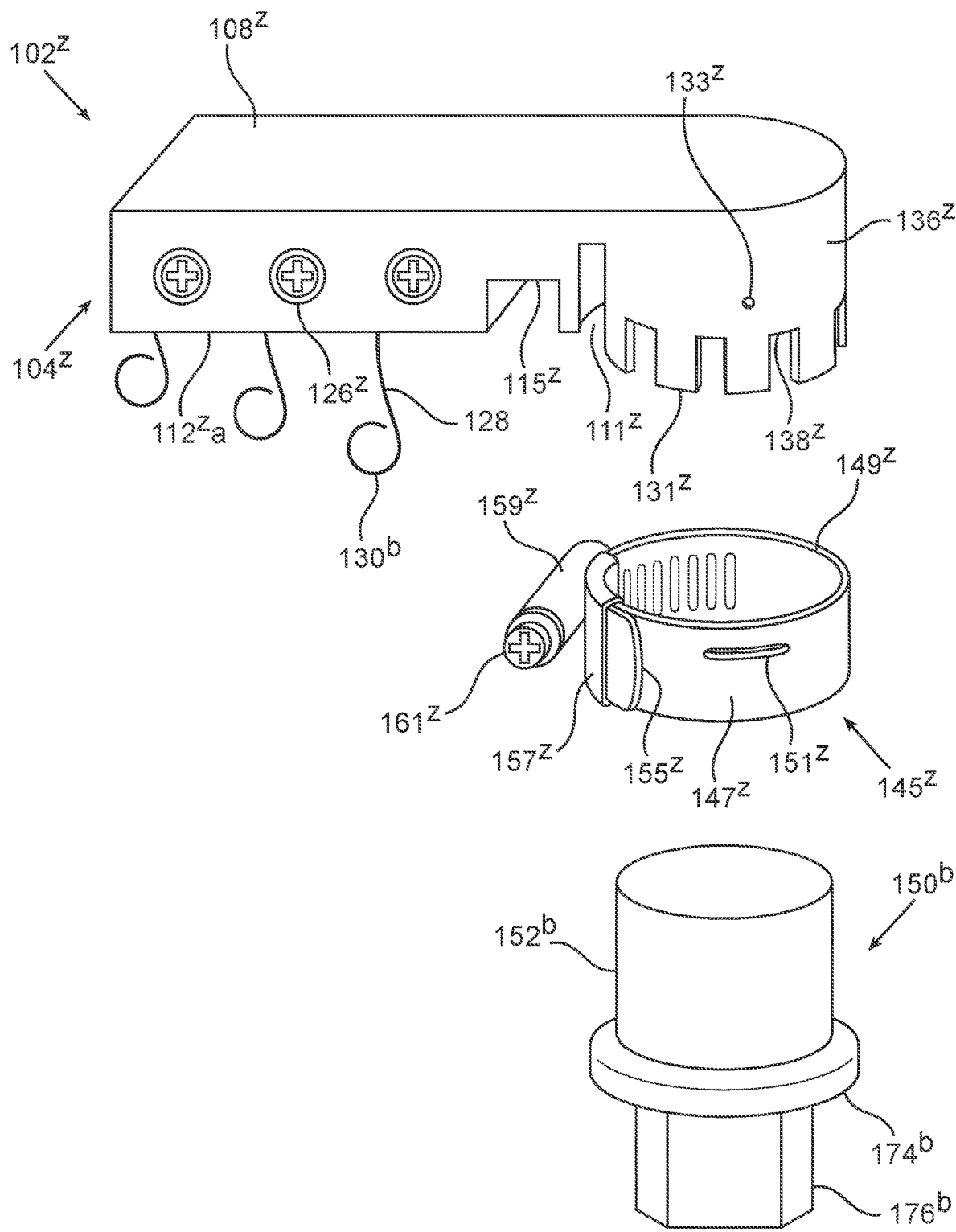
FIG. 20A constitutes an exploded view in perspective of a distraction assembly, according to some embodiments.
Figure 20B:
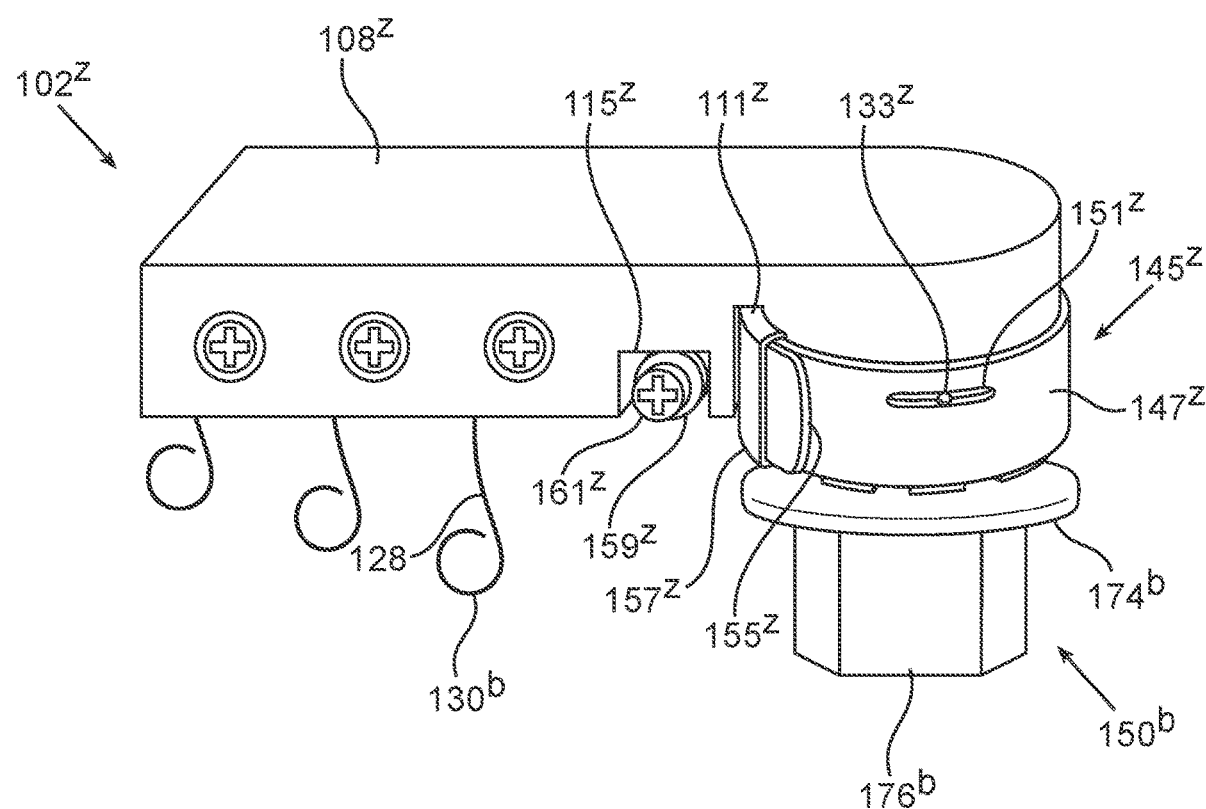
FIG. 20B constitutes a view in perspective of an assembled distraction assembly, according to some embodiments.

Reference now is made to FIGS. 19A-20B, depicting different embodiments of a distraction assembly. FIGS. 19A and 19B constitute exploded and assembled views in perspective of a distraction assembly comprising a distraction device 100$^x$ and a contraction ring 145$^x$, according to some embodiments. FIGS. 20A and 20B constitute exploded and assembled views in perspective of a distraction assembly comprising a distraction device 100$^z$ and a clamp 145$^z$, according to some embodiments.

According to some embodiments, there is provided a distraction assembly comprising a distraction device 100 equipped with a contractible adaptor member 136, and a clamp 145 configured to engage with the distraction device 100 by placement thereof over the exterior of the contractible adaptor member 136, and is further configured to exert force on the contractible adaptor member 136, sufficient bend at least a portion of the contractible adaptor member 136 radially inwards, for example against an implant abutment 150.

Aside from the contractible adaptor member 136, the distraction device 100 of such a distraction assembly can be similar in structure and function to any other embodiment of a distraction device 100 disclosed throughout the specification.

A contractible adaptor member 136 is configured such that at least a portion thereof can bend or contract radially inwards, upon application of an external force thereon. According to some embodiments, the contractible adaptor member 136 is configured to contract along at least a portion thereof, by an amount sufficient to press against or engage an abutment 150 in a manner that will prevent spontaneous disengagement thereof.

According to some embodiments, the contractible adaptor member 136 comprises a plurality of axial extensions 131, separated by notches 138 there between. The plurality of axial extensions 131 are configured to bend or contract radially inwards, upon application of an external force along their circumference. According to some embodiments, the material properties and/or dimension of the plurality of axial extensions 131, including their thickness, are chosen to enable a desired amount of radial inward bending, responsive to a predetermined range of forces applied thereon.

According to some embodiments, the clamp 145 is configured for placement over the circumference contractible adaptor member 136, such that at least a portion of the clamp 145 may encircle and contact at least a portion of the plurality of axial extensions 131.

According to some embodiments, the clamp 145 comprises a band 147 and a worm gear mechanism 159 configured to contract or expand a formed by the band 147. According to some embodiments, the worm gear mechanism 159 comprises a worm gear 161. According to some embodiments, the clamp 145 comprises a backing support 157.

The band 147 comprises a first end portion 155 and a second end portion (hidden from view in FIG. 19A-20B). According to some embodiments, the second end portion 155 is connected to the worm gear mechanism 159, but could be connected to the backing support 157, or could be connected to both. According to some embodiments, the first end portion 155 is threaded in the worm gear mechanism 159 and mechanically interconnected with the worm gear mechanism 159. According to some embodiments, the second end portion moves in response to operation of the worm gear mechanism 159.

According to some embodiments, the band 147 comprises a plurality of laterally extending slots (not numbered). The amount of slots can be determined according to the expected or desired contraction adjustment amount. According to some embodiments, the slots extend only along a relatively small portion of the band 147, for example only along less than a quarter of the total length of the band 147, since the desired contraction adjustment amount is relatively small (e.g. reduction of less than 2 mm. of the diameter of the loop formed by the band 147 when placed over the contractible adaptor member 136).

The worm gear mechanism 159 is configured to cause contraction or expansion of the clamp 145 and keep the clamp 145 at the adjusted position. According to some embodiments, the worm gear mechanism 159 comprises a worm 161, configured to rotate within a cavity of the worm gear mechanism 159 and engage the slots of the band 147 to adjust the diameter of the clamp 145. The worm 161 comprises a tooling interface exposed for engagement with a tooling device. The tooling interface of the worm 161 can be similar to any embodiments disclosed herein for the tooling interface 126.

The backing support 157 supports the worm gear mechanism 159 and guides the band 147 along a portion of its circumferential extent.

According to some embodiments, the main body 102 of the distraction device further comprises an arcuate slot 111 disposed between the strings positioning member 104 and the contractible adaptor member 136, configured to accommodate at least a portion of the clamp 145 when place therein. According to some embodiments, the arcuate slot 111 is dimensioned to accommodate at least a portion of the band 147. According to some embodiments, the arcuate slot 111 is dimension to accommodate at least a portion of the band 147 and the backing support 157.

According to some embodiments, the strings positioning member 104 further comprises a worm recess 115 adjacent the contractible adaptor member 136, preferably adjacent the arcuate slot 111. The worm recess 115 is configured to accommodate the worm gear mechanism 159. According to some embodiments, the worm recess 115 is open ended at least along one of the sidewalls 112, to provide access to the tooling interface of the worm 161. According to some embodiments, there is a continuity formed between the arcuate slot 111 and the worm recess 115 along at least a portion of their interfacing border.

According to some embodiments, the band 147 further comprises at least one retaining slot 151 extending in a circumferential direction, and the contractible adaptor member 136 comprises at least one retaining protrusion 133 extending radially outwards therefrom, and configured to be positioned within the respective retaining slot 151 when the clamp 145 is engaged with the distraction device 100, thereby preventing axial movement of the clamp 145 in the distal or proximal directions, to minimize the risk of the clamp 145 slipping out of position when engaged with the distraction device 100.

FIG. 19A constitutes an exploded view in perspective of a distraction assembly comprising a distraction device 100$^x$ and a contraction ring 145$^x$, configured to be used in conjunction with an implant abutment 150$^b$, according to some embodiments.

The clamp 145$^x$ comprises a band 147$^x$, a worm gear mechanism 159$^x$ having a worm 161$^x$, and a backing support 157$^x$. The distraction device 100$^x$ comprises a contractible adaptor member 136$^x$ having a plurality of axial extensions 131$^x$, separated by notches 138$^x$ there between. The distraction device 100$^x$ further comprises an arcuate slot 111$^x$ and a worm recess 115$^x$.

The contractible adaptor member 136$^x$ further comprises a retaining protrusion 133$^x$ in the form of a radially extending pin, and the clamp 145$^x$ further comprises a retaining slot 151$^x$, preferably located closer to a proximal edge of the band 147$^x$, so as to be able to accommodate a respective retaining protrusion 133$^x$ located at a region proximal to the axial extensions 131$^x$.

The contractible adaptor member 136 comprises a connection platform in the form of a mounting bore (similar to mounting bore 138 disclosed herein), configured to connect with a mount. In the embodiment exemplified in FIGS. 19A-20B, the mount is an abutment 150$^b$, which can be either a standard abutment as used by and known to persons skilled in the art, or an abutment specifically designed for use with a distraction system having a distraction device 100 equipped with a contractible adaptor member 136.

The abutment 150$^b$ exemplified in the embodiments shown in FIGS. 19A-20B differs from the embodiments shown in FIGS. 18A-D in that the abutment distal portion 152$^x$ is formed as a cylinder extending distally from the abutment mid-portion 174$^b$, devoid of screw threads or polyhedral circumferential surfaces. However, it will be clear that in according to other embodiments, a distraction device 100 equipped with a contractible adaptor member 136 can be used with any other type of a mount, including abutments 150 having a threaded or polyhedral formed abutment distal portions 152, a dental crown, a dental screw, a dental bridge, a denture, a native tooth and the like.

FIG. 19B shows the distraction assembly of FIG. 19A assembled over the abutment 150$^b$, wherein the abutment distal portion 152$^b$ is received within the mounting bore of the contractible adaptor member 136$^x$, and the clamp 145$^x$ is engaged with the distraction device 100$^x$ such that the band 147$^x$ and backing support 157$^x$ are accommodated within the arcuate slot 111$^x$, the worm gear mechanism 159$^x$ is accommodate within the worm recess 115$^x$, and the retaining protrusion 133$^x$ is accommodated within the retaining slot 151$^x$.

In use, rotating the worm 161$^x$ in a predefined directing facilitates contraction of the clamp 145$^x$ over the contractible adaptor member 136$^x$, thereby exerting sufficient force to bend the axial extensions 131$^x$ radially inwards, until they are pressed against the abutment distal portion 152$^b$ at a force sufficient to prevent relative spontaneous movement between the distraction device 100$^x$ and the abutment 150$^b$.

The retaining slot 151$^x$ is configured to allow it to move over the retaining protrusion 133$^x$ extending there through in a circumferential direction, thereby enabling contraction or expansion of the clamp 145$^x$ while preventing it from slipping in a proximal or distal directions.

FIG. 20A constitutes an exploded view in perspective of a distraction assembly comprising a distraction device 100$^z$ and a contraction ring 145$^z$, configured to be used in conjunction with an implant abutment 150$^b$, according to some embodiments. FIG. 20B shows the distraction assembly of FIG. 20A assembled over the abutment 150$^b$.

The main difference between the distraction assembly comprising a distraction device $100^z$ and a contraction ring $145^z$ from the distraction assembly comprising a distraction device $100^x$ and a contraction ring $145^x$, is that while the contraction ring $145^x$ is configured to engage with distraction device $100^x$ from a proximal direction, such that the proximal edge of the clamp $145^x$ is distally spaced from the proximal edge of the contractible adaptor member $136^x$ when engaged therewith, the contraction ring $145^z$ is configured to engage with distraction device $100^z$ from a distal direction, such that the distal edge of the clamp $145^z$ is proximally spaced from the distal edge of the contractible adaptor member $136^z$ when engaged therewith.

FIG. 20B shows the distraction assembly of FIG. 20A assembled over the abutment $150^b$, wherein the clamp $145^z$ is positioned between the abutment mid-portion $174^b$ and a distal end of the arcuate slot $111^z$. Accordingly, the retaining slot $151^z$ is located closer to a distal edge of the band $147^z$, so as to be able to accommodate a respective retaining protrusion $133^z$ located at a region proximal to the axial extensions $131^z$.

According to some embodiments, the distraction assembly further comprises an abutment, such as abutment $150^b$. String engagement portion 130 is configured to engage a receiving area 42 of a miniscrew 40. According to some embodiments, miniscrew 40 comprises any orthodontic screw or other anchoring appliance such as bone plates or dental implants known in the art.

According to some embodiments, miniscrew 40 comprises proprietary and/or customized screws, configured for engagement with string engagement portion 130. According to some embodiments, distraction system 200 is a system comprising at least a distraction device 100, and any of: an abutment 150, bone screw 20, rotation tool 76, at least one miniscrew 40, and any combination thereof.

The terms "miniscrew" and "anchoring implant means", as used herein, are interchangeable.

Figure 21A:
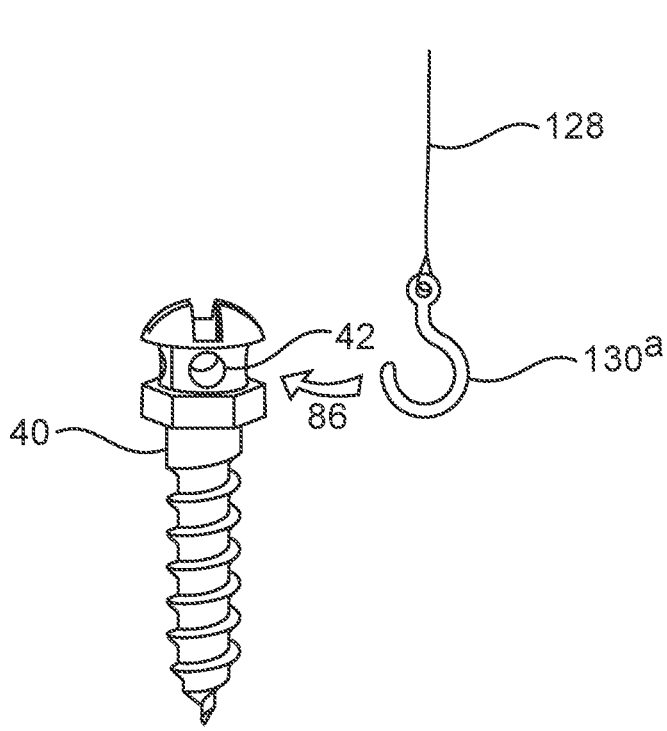
FIG. 21A constitutes a view in perspective of a miniscrew next to a string engagement portion in the form of a hook, according to some embodiments.
Figure 21B:
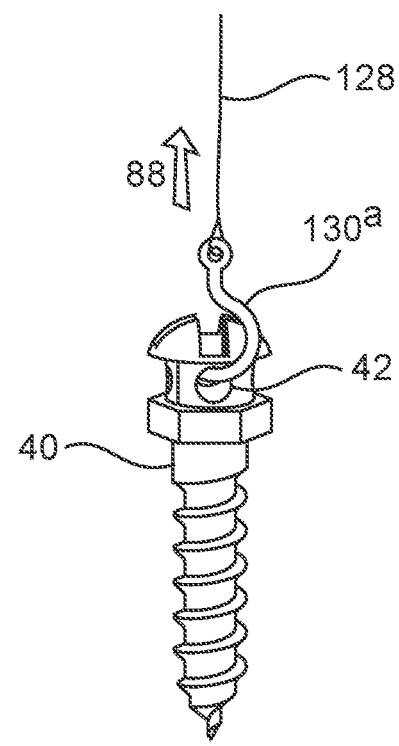
FIG. 21B constitutes a view in perspective of the hook engaged with the miniscrew of FIG. 21A, according to some embodiments.
Figure 21C:
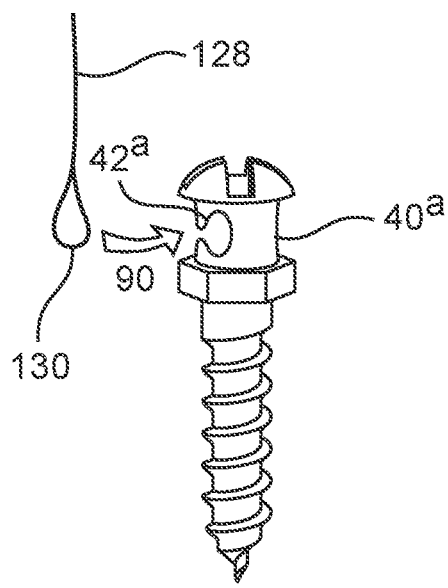
FIG. 21C constitutes a view in perspective of a miniscrew next to a string engagement portion in the form of a loop, according to some embodiments.
Figure 21D:
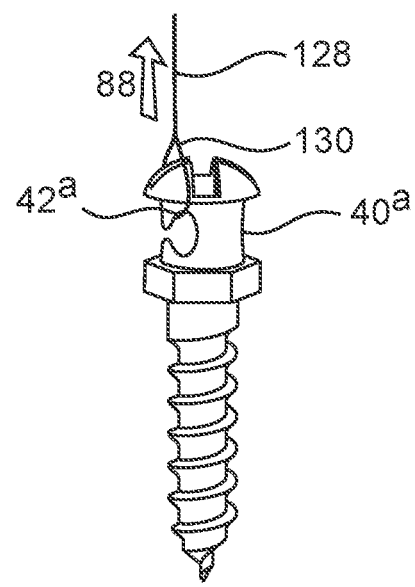
FIG. 21D constitutes a view in perspective of the loop engaged with the miniscrew of FIG. 21C, according to some embodiments.

Reference now is made to FIGS. 21A-21G, depicting different embodiments of miniscrew 40. According to some embodiments, receiving area 42 of a miniscrew 40 is formed as a through-hole (see FIGS. 21A-21B). FIG. 21A illustrates a string engagement portion formed as a hook $130^a$, configured to be received, in the direction of arrow 86, within receiving area 42. Once hook $130^a$ is inserted within receiving area 42, pulling string 128 in the direction of arrow 88 (see FIG. 21B) exerts a pull-force in the same direction on miniscrew 40.

According to some embodiments, receiving area 42 of miniscrew 40 is formed as a recess having at least one distal vertical extension (not numbered). FIG. 20C illustrates a string engagement portion formed as loop 130, configured to be received, in the direction of arrow 90, within receiving area $42^a$. Once string engagement portion 130 is accepted within receiving area $42^a$, pulling string 128 in the direction of arrow 88 (see FIG. 20D) exerts a pull-force in the same direction on miniscrew $40^a$. The distal vertical extension (not numbered) prevents string engagement portion 130 from slipping out of receiving area $42^a$ as long as string 128 is kept in vertically tensed.

Figure 21E:
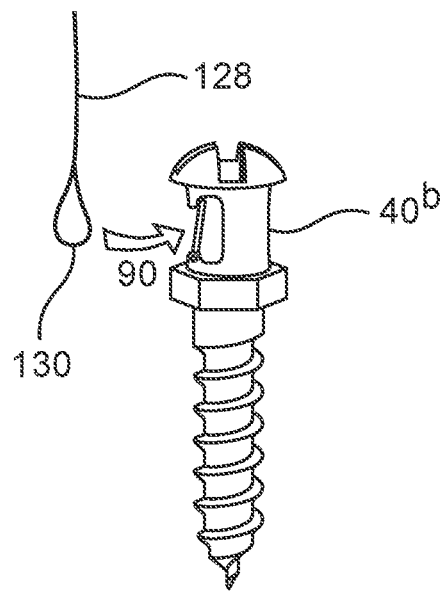
FIG. 21E constitutes a view in perspective of a miniscrew having a latch, next to a string engagement portion in the form of a hook, according to some embodiments.
Figure 21F:
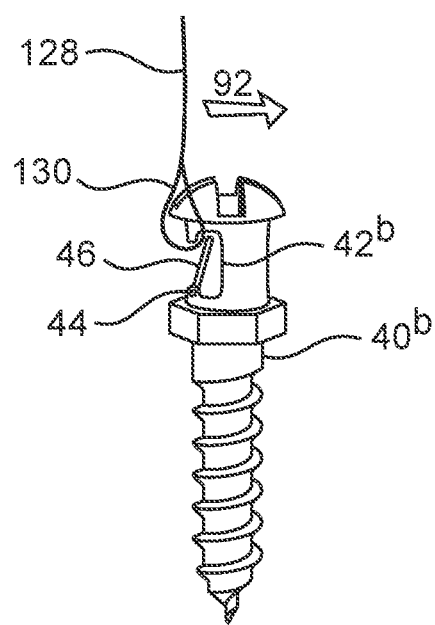
FIG. 21F constitutes a view in perspective of the loop being inserted into a receiving portion past the latch of FIG. 21E.
Figure 21G:
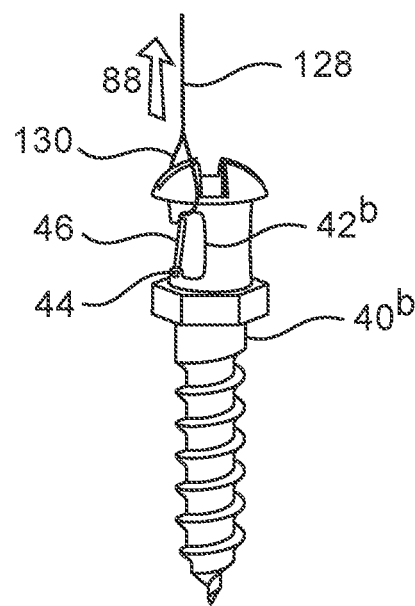
FIG. 21G constitutes a view in perspective of the loop engaged with the miniscrew of FIG. 21E, according to some embodiments.

According to some embodiments, receiving area 42 of a miniscrew 40 comprises an opening with a latch 46. FIG. 21E illustrates a string engagement portion formed as a loop 130, configured to be received, in the direction of arrow 90, within receiving area $42^b$. A latch 46 is movably connected to an edge of receiving area $42^b$ via a pivot 44. Latch 46 is movable between an open position (see FIG. 21F) and a closed position (see FIG. 21G). String engagement portion 130 can force latch 46 to pivotally rotate about pivot 44 in the direction of arrow 92. According to some embodiments, pivot 44 comprises a spring, such as a coil spring, configured to force latch 44 to a closed position when string engagement portion 130 no longer interacts there with. Once string engagement portion 130 is accepted within receiving area $42^b$, pulling string 128 in the direction of arrow 88 (see FIG. 21G) exerts a pull-force in the same direction on miniscrew $40^b$. Latch 46, while in a closed position, prevents string engagement portion 130 from slipping out of receiving area $42^b$.

Figure 22A:
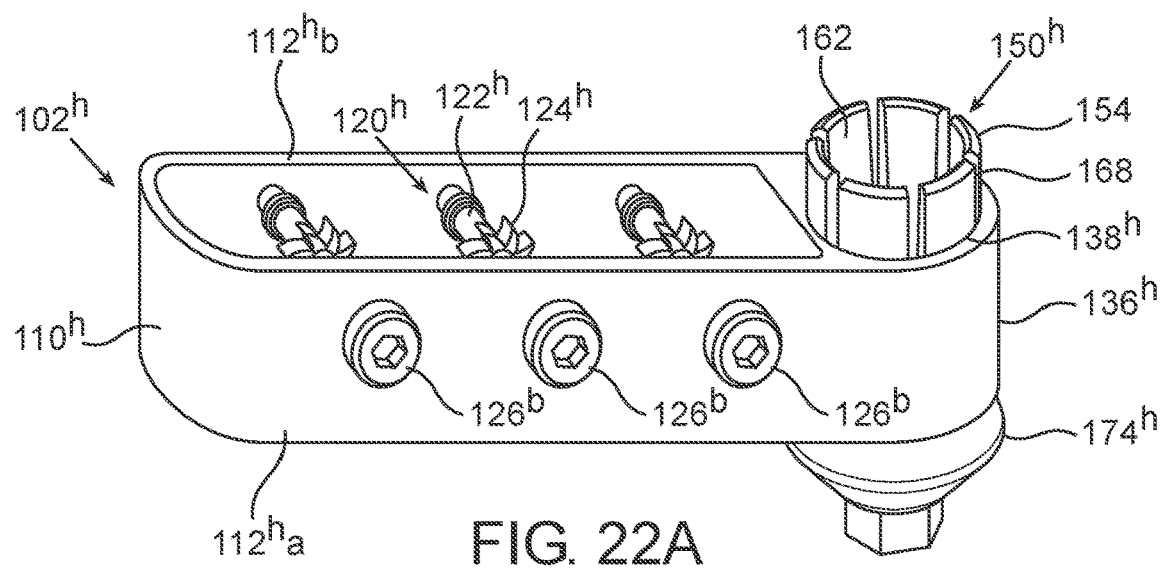
FIG. 22A constitutes a view in perspective of a distraction device without a distal panel, engaged with an abutment, according to some embodiments.

Reference now is made to FIGS. 22A-27, illustrating a more particular embodiments of distraction device $100^h$ or $100^k$, abutment $150^h$, and distraction system $200^h$. FIGS. 22A, 22B and 22C constitute a view in perspective, a top view and a cross-sectional side view, respectively, of a distraction device $100^h$ mounted on an abutment $150^h$, according to some embodiments.

Distraction device $100^h$ comprises a string positioning member $104^h$ integrally formed with an adaptor member $136^h$. String positioning member $104^h$ comprises first and second sidewalls $112^h$a and $112^h$b, respectively. String positioning member $104^h$ further comprises a curved front panel $110^h$, integrally formed with sidewalls $112^h$. According to some embodiments, string positioning member $104^h$ further comprises a distal panel $108^h$ (shown in FIG. 22C, but not shown in FIGS. 22A-22B in order to expose components housed within string positioning member $104^h$). According to some embodiments, string positioning member $104^h$ further comprises a proximal panel $106^h$, provided with at least one positioning feature $118^h$ formed as an aperture.

Figure 22B:
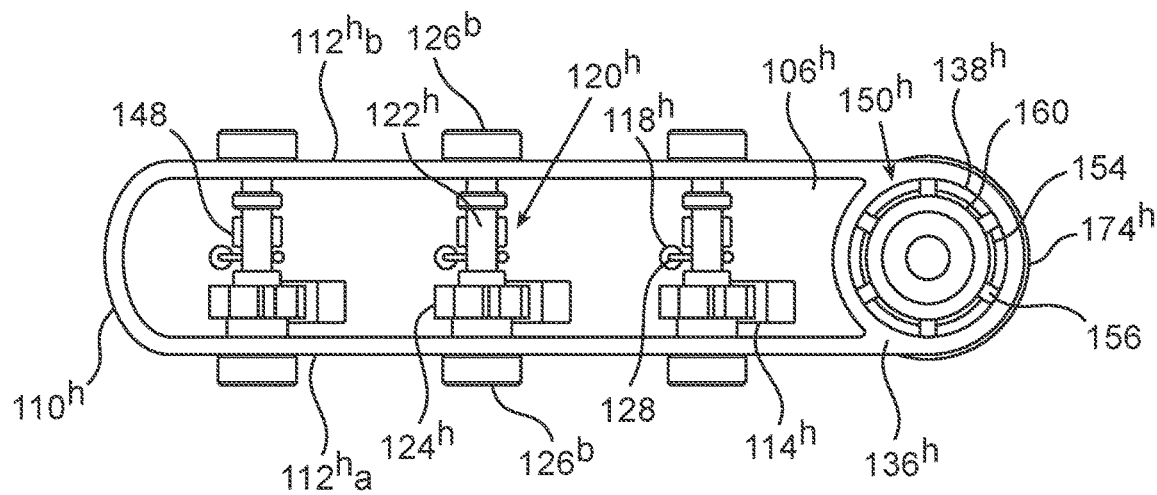
FIG. 22B constitutes a top view of the distraction device and abutment of FIG. 22A.
Figure 22C:
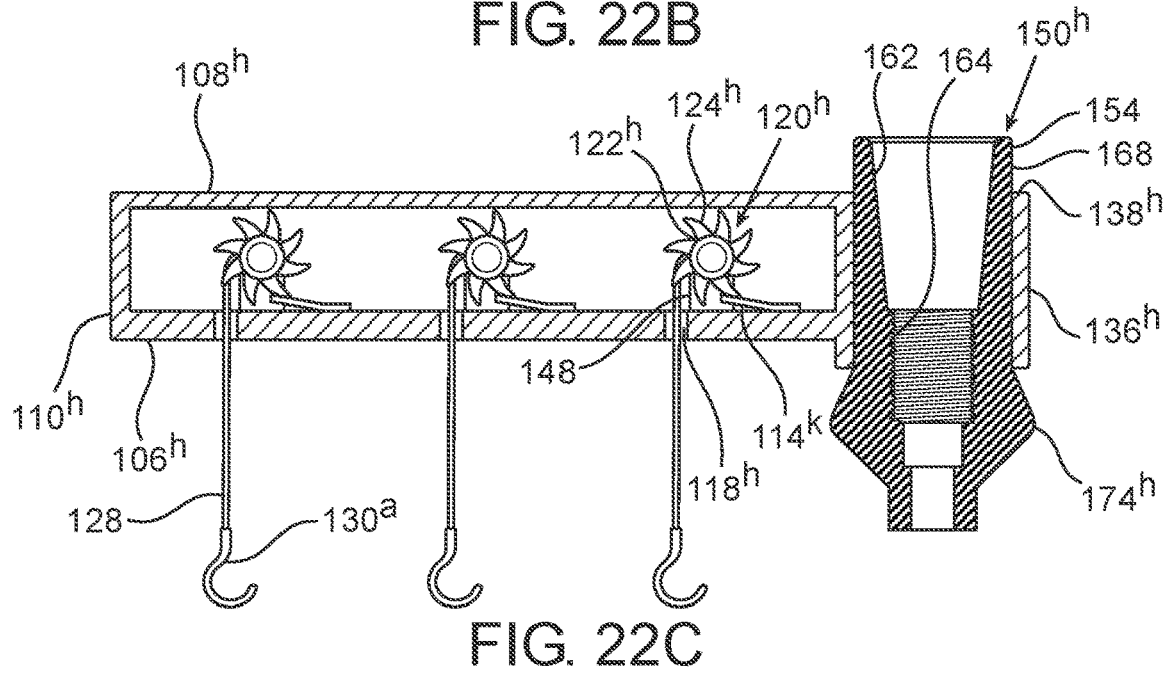
FIG. 22C constitutes a side cross-sectional view of a distraction device engaged with an abutment, according to some embodiments.

Distraction device $100^h$ further comprises at least one string pull assembly $120^h$. FIGS. 22A-22C illustrate an embodiment with three exemplary string pull assemblies $120^h$ formed as rotatable string pull assemblies. Each string pull assembly $120^h$ comprises a movable element $122^h$ formed as a shaft, at least one tooling interface $126^b$ extending through at least one sidewall $112^h$, a gear $124^h$ rigidly connected to movable element $122^h$, and a string 128 affixed at the first string end (not numbered) to movable element $122^h$, passing through the at least one positioning feature $118^h$, and having a string engagement portion 130, such as a hook $130^a$ (see FIG. 22C), at the second string end.

Distraction device $100^h$ further comprises at least one pawl 114, configured to engage with the at least one gear $124^h$. FIG. 18C illustrates an exemplary pawl $114^h$, attached to proximal panel $106^h$.

In the example provided by FIG. 22B, each string pull assemblies $120^h$ comprises two tooling interfaces $126^h$, one at each end of movable element $122^h$, while movable element $122^h$ is supported by both first sidewall $112^h$a and second sidewall $112^h$b. According to some embodiments, distraction device $100^h$ further comprises at least one movable element support 148. According to some embodiments, movable element $122^h$ is further supported by a movable element support 148 (see FIGS. 22B-22C), extending vertically from proximal panel $106^h$.

Adaptor member $136^h$ comprises mounting bore $138^h$, configured to receive abutment distal portion $152^h$ of abutment $150^h$. According to some embodiments, mounting bore $138^h$ comprises a circular cross section, devoid of any threading.

Figure 23A:
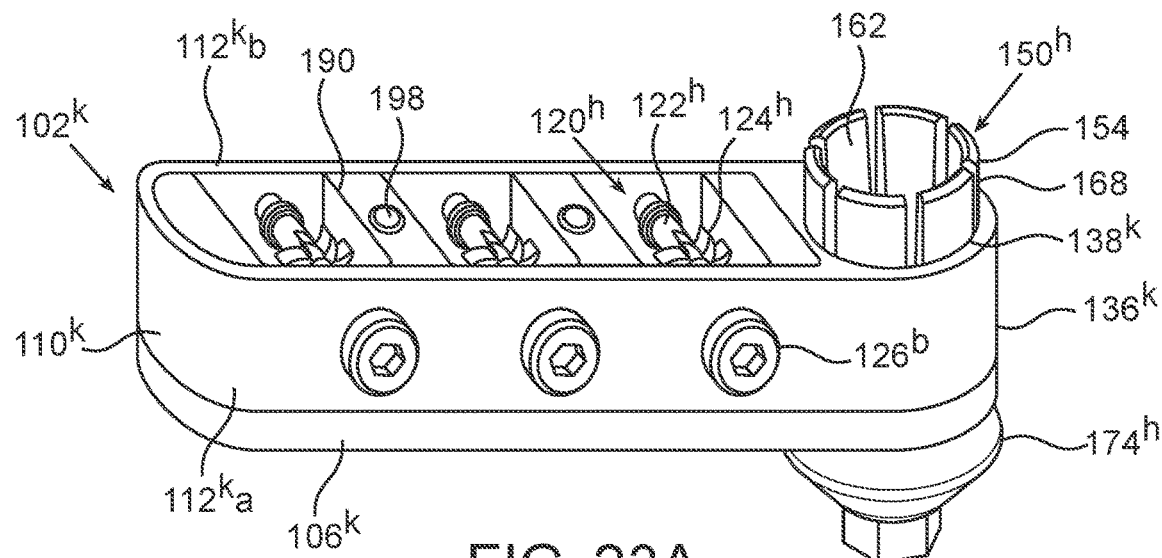
FIG. 23A constitutes a view in perspective of a distraction device having positioning member chambers, without a distal panel, engaged with an abutment, according to some embodiments.
Figure 23B:
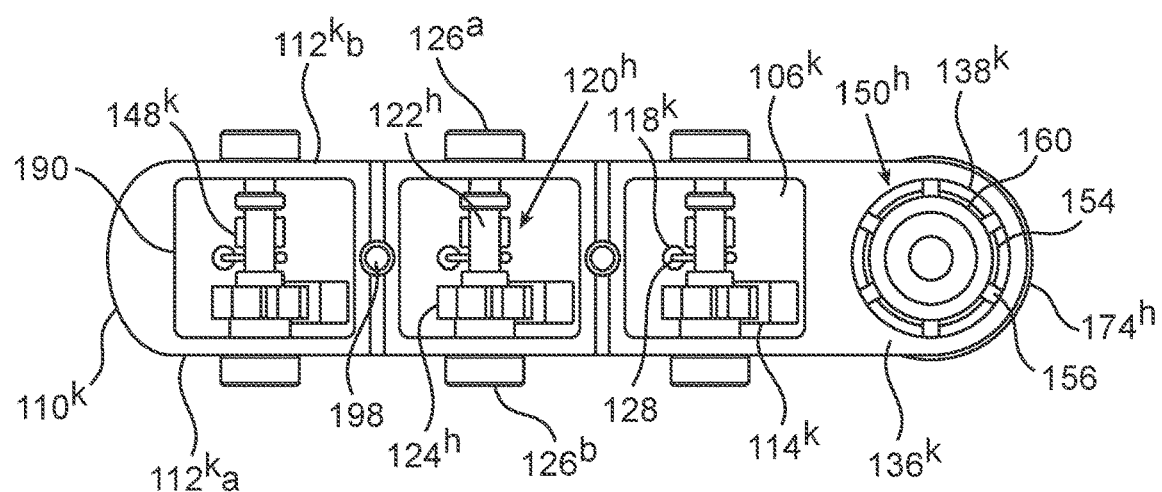
FIG. 23B constitutes a top view of the distraction device and abutment of FIG. 23A.
Figure 23C:
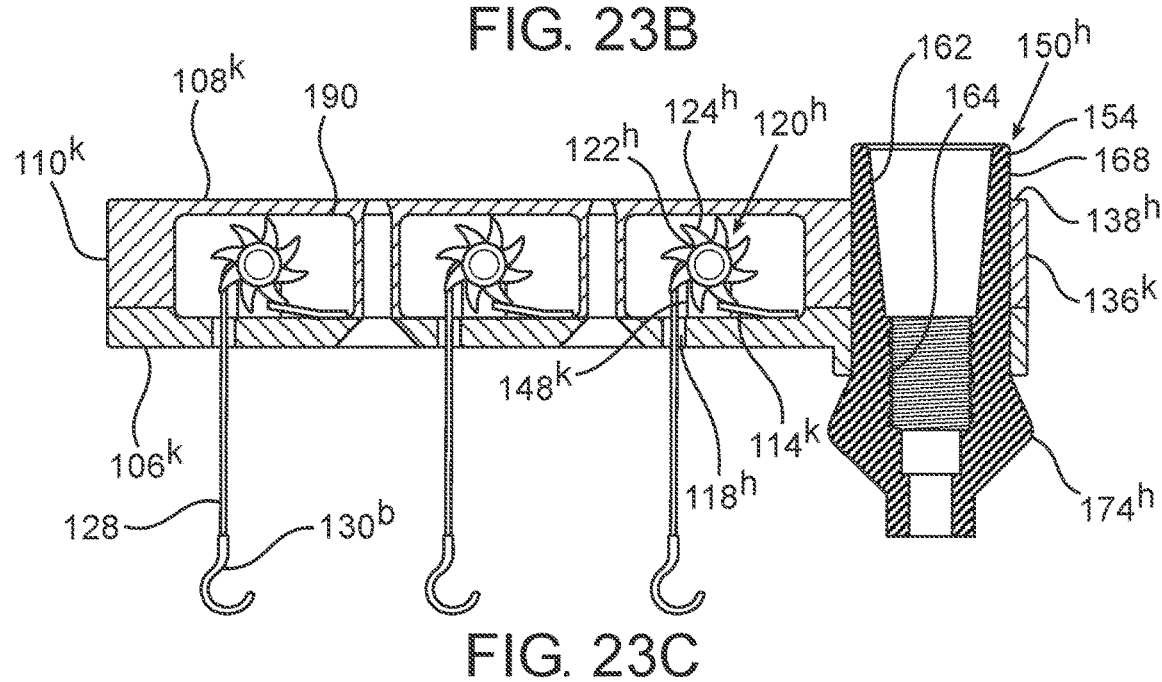
FIG. 23C constitutes a side cross-sectional view of a distraction device having positioning member chambers, engaged with an abutment, according to some embodiments.

FIGS. 23A, 23B and 23C constitute a view in perspective, a top view and a cross-sectional side view, respectively, of a distraction device $100^k$ mounted on an abutment $150^h$, according to some embodiments.

Distraction device 100$^k$ comprises a string positioning member 104$^k$ integrally formed with an adaptor member 136$^k$. String positioning member 104$^k$ comprises first and second sidewalls 112$^k$a and 112$^k$b, respectively. String positioning member 104$^k$ further comprises a curved front panel 110$^k$, integrally formed with sidewalls 112$^k$. Distraction device 100$^k$ further comprises at least one string pull assembly 120$^h$. FIGS. 23A-23C illustrate an embodiment with three exemplary string pull assemblies 120$^h$, formed as rotatable string pull assemblies.

According to some embodiments, string positioning member 104$^k$ further comprises a distal panel 108$^k$ (shown in FIG. 23C, but not shown in FIGS. 23A-23B in order to expose components housed within string positioning member 104$^k$). According to some embodiments, distal panel 108$^k$ comprises at least one distal panel opening (not numbered), configured to accommodate a distal portion of a fastening element 198. According to some embodiments, string positioning member 104$^h$ further comprises a proximal panel 106$^k$, provided with at least one positioning feature 118$^k$ formed as an aperture and at least one proximal panel opening (not numbered) configured to accommodate a proximal portion of fastening element 198. According to some embodiments, proximal panel 106$^k$ is detachably connected to any of: sidewalls 112$^k$, front panel 110$^k$, distal panel 108$^k$, and any combination thereof.

Distraction device 100$^k$ further comprises at least one pawl 114, configured to engage with the at least one gear 124$^h$. FIG. 23C illustrates an exemplary pawl 114$^k$, attached to proximal panel 106$^k$.

According to some embodiments, string positioning member 104$^k$ further comprises at least one positioning member chamber 190, bordered between first sidewall 112$^k$a and second sidewall 112$^k$b, and when present, between distal panel 108$^k$ and proximal panel 106$^k$. Each chamber 190 is configured to house a string pull assembly 120$^h$. FIGS. 23A-23C illustrate an exemplary embodiment of three positioning member chambers 190, each housing a string pull assembly 120$^h$, the movable element 122$^h$ extending through between first sidewall 112$^k$a and second sidewall 112$^k$b, and further supported by movable element support 148$^k$, vertically extending from proximal panel 106$^k$. Neighboring positioning member chambers 190 are spaced apart by a positioning member rib (not numbered). According to some embodiments, each positioning member rib comprises a channel (not numbered) configured to accommodate the body (not numbered) of fastening element 198.

According to some embodiments, string positioning member 104$^k$ comprises at least one fastening element 198, such as a bolt or a rivet, configured to fasten detachable elements of string positioning member 104$^k$. According to some embodiments, fastening elements 198 are configured to attach detachable proximal panel 106$^k$ to the remainder of frame 104$^k$ (see FIGS. 23A-23C). According to some embodiments, fastening elements 198 are configured to attach detachable distal panel 108$^k$ to the remainder of string positioning member 104$^k$ (embodiment not illustrated).

Advantageously, fastening elements 198 provide additional structural reinforcement to string positioning member 104$^k$ in the vertical direction.

Adaptor member 136$^k$ comprises mounting bore 138$^k$, configured to receive abutment distal portion 152$^h$ of abutment 150$^h$. According to some embodiments, mounting bore 138$^k$ comprises a circular cross section, devoid of any threading.

Figures 24A, 24B:
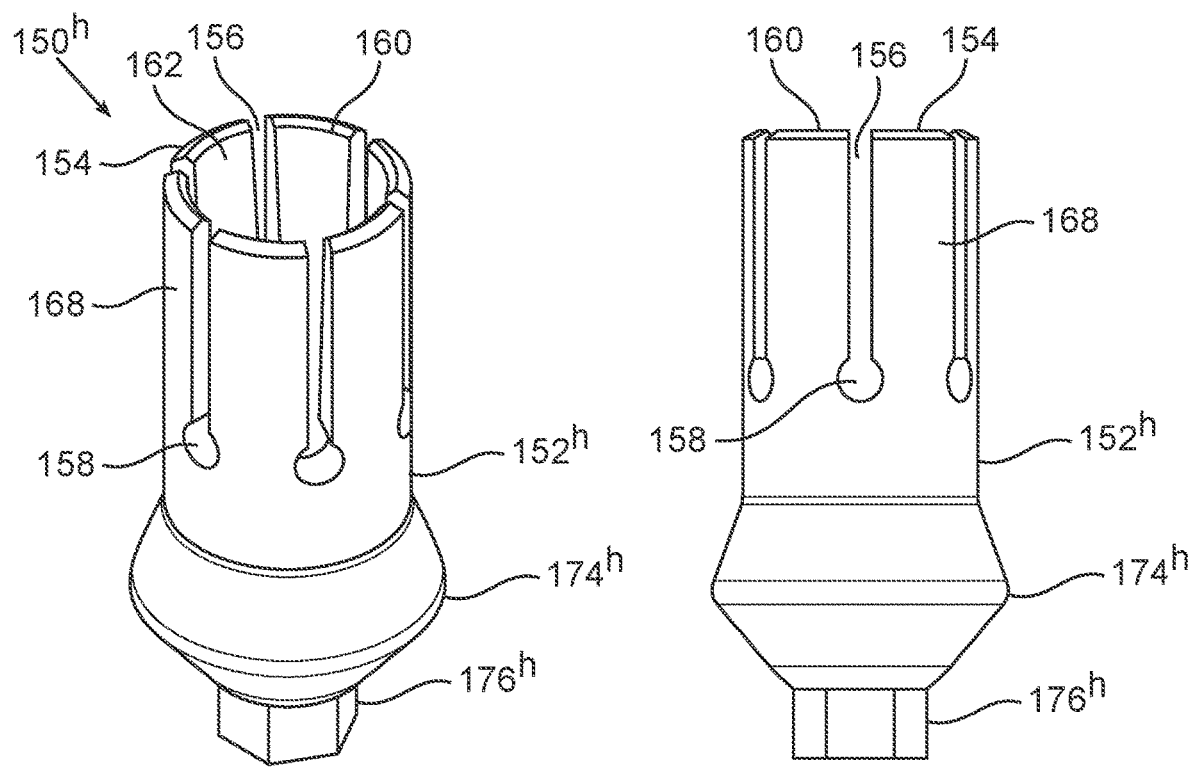
FIG. 24A constitutes a view in perspective of an abutment, according to some embodiments.
FIG. 24B constitutes a side view in of the abutment of FIG. 24A.

FIGS. 24A and 24B constitute a view in perspective and a side view, respectively, of abutment 150$^h$, also presented in a cross-sectional side view in FIGS. 22C and 23C, according to some embodiments. Abutment 150$^h$ comprises an abutment distal portion 152$^h$, abutment mid-portion 174$^h$ and abutment proximal portion 176$^h$. Abutment proximal portion 176$^h$ comprises a polyhedral-shaped structure, configured to be inserted into a matching socket of a bone screw 20 (illustrated in FIG. 27). According to some embodiments, abutment distal portion 152$^h$, abutment mid-portion 174$^h$ and abutment proximal portion 176$^h$ are integrally formed.

Abutment distal portion 152$^h$ is provided with a plurality of regularly spaced vertical notches 156 that create a corresponding plurality of wings 154, provided with intrinsic flexibility. According to some embodiments, such as illustrated in FIGS. 24A and 24B, all wings 154 are oriented in the vertical direction. According to some embodiments, each notch 156 is provided at its proximal end with a notch groove 158, having a diameter larger than the width of notch 156, thereby providing additional flexibility to wings 154.

Each wing 154 comprises a wing inner surface 162 and a wing outer surface 168. All of the wing inner surfaces 162, together with the notches 156, define an abutment distal receiving opening 160, configured to receive a plug 180 (see FIG. 25).

The largest cross-sectional diameter of abutment mid-portion 174$^h$ is larger than either the largest cross-sectional diameter of abutment distal portion 152$^h$, or the largest cross-sectional diameter of abutment proximal portion 176$^h$. According to some embodiments, mid-portion 174$^h$ is formed with a cylindrical convexly curved shape. FIGS. 24A and 24B illustrate abutment mid-portion 174$^h$ having a variable cross-section along its length, expanding in diameter from its distal connection edge (not numbered) with abutment distal portion 152$^h$ to a maximal diameter (not numbered), and then reduced in diameter towards the proximal connection edge (not numbered) with abutment proximal portion 176$^h$.

According to some embodiments, the proximal edge of wings 154 (not numbered), positioned at about a vertical center point of notch grooves 158, is spaced from abutment mid-portion 174$^h$, thereby defining an abutment distal portion base (not numbered).

According to some embodiments, abutment 150$^h$ is in a resting position, as depicted in FIGS. 24A-24B, when no plug 180 is inserted therein. According to some embodiments, angle $\alpha$ (see FIG. 26B), defined as the angle between each wing 154 and the abutment distal portion base, equals 180° in a resting position. According to some embodiments, angle $\alpha$ is within a range of 160°-200° in a resting position. According to some embodiments, angle $\alpha$ is within a range of 175°-180° in a resting position.

Figure 25:
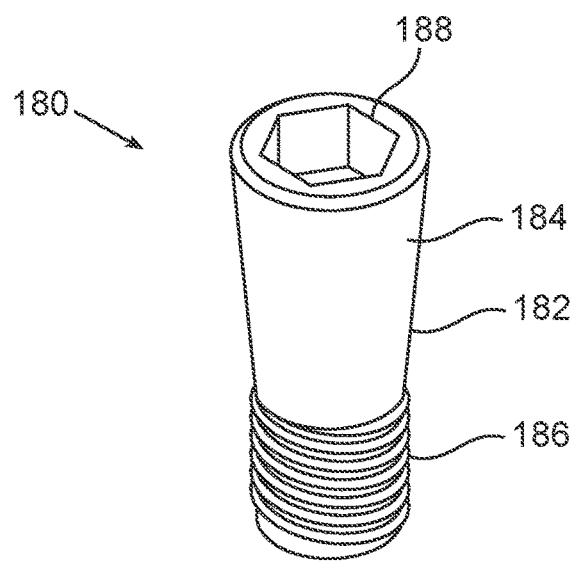
FIG. 25 constitutes a view in perspective of a plug, according to some embodiments.

FIG. 25 constitutes a view in perspective of a plug 180, according to some embodiments. Plug 180 comprises a plug distal portion 182 having a plug distal outer surface 184, and a plug base 186. Plug 180 is configured to be received within abutment 150$^h$, inserted thereto through abutment distal receiving opening 160. Plug distal portion 182 is formed with at least one region along its length, having a diameter slightly larger than the diameter of abutment distal receiving opening 160 when abutment 150$^h$ is in a resting position.

According to some embodiments, as depicted in FIG. 25, plug distal portion 182 is provided with a frustoconical profile, such that its diameter at its distal edge (not numbered) is wider than its diameter at its proximal connection edge (not numbered) with plug base 186. According to some embodiments, plug base 186 is provided with a threading (nut numbered), configured to match a complementary threading of abutment base receiving portion 164 (see FIGS. 22C and 23C).

According to some embodiments, as depicted in FIG. 25, plug distal portion 182 is provided at its distal face (not numbered) with a plug screw-head 188, configured to receive an external tool (such as a key or a wrench) for rotation thereof.

According to some embodiments, plug distal portion 182 is provided with a thread, matching a thread on wing inner surfaces 162 (embodiment not shown).

According to some embodiments, plug 180 is devoid of screw threads, configured for insertion into abutment $150^h$ by means of impact instead of by means of rotary motion (embodiment not shown).

Figure 26A:
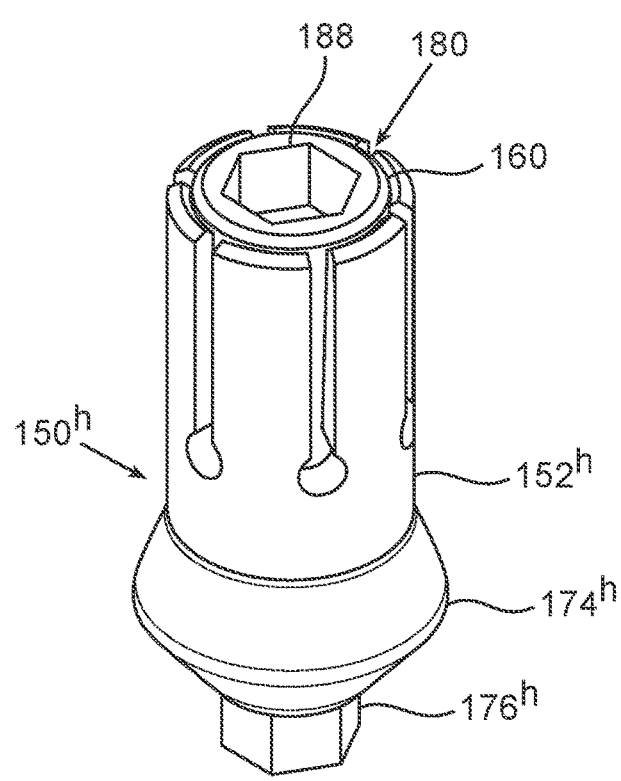
FIG. 26A constitutes a view in perspective of a plug positioned within an abutment, according to some embodiments.
Figure 26B:
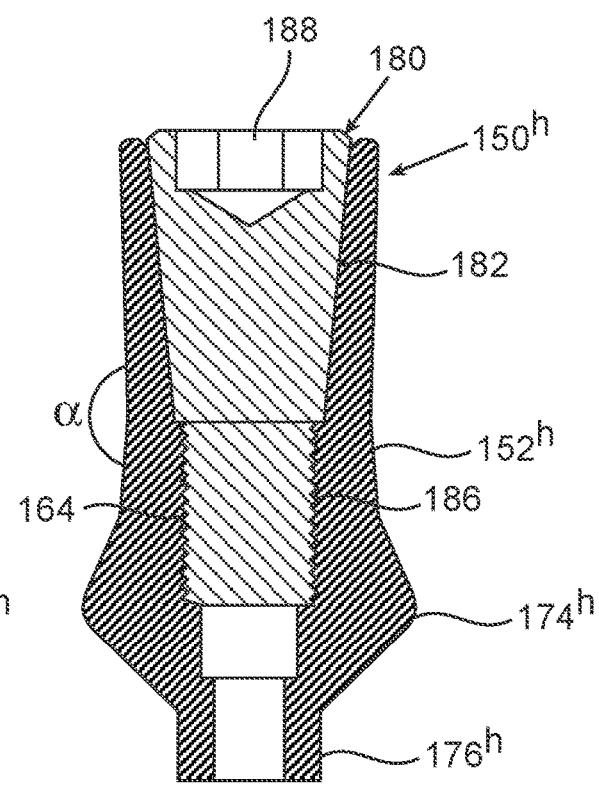
FIG. 26B constitutes a cross-sectional side view in perspective of a plug positioned within an abutment, according to some embodiments.

FIGS. 26A and 26B constitute a view in perspective and a cross-sectional side view, respectively, of a plug 180 positioned within abutment $150^h$, according to some embodiments. When plug 180 is inserted through abutment distal receiving opening 160 into abutment $150^h$, plug distal outer surface 184 is engaged with wing inner surfaces 162. Plug distal portion 182 acts as a wedge, exercising a divaricating force in a radial direction towards wings 154. According to some embodiment, wings 184 are flexed radially outwards, such that angle α is smaller than its value in a resting position.

According to some embodiments, plug 180 is inserted into abutment $150^h$ with rotary motion, wherein plug base 186 is threaded into abutment base receiving portion 164, along at least a portion of plug base 186. According to some embodiments, $α_{min}$ is defined as the resulting angle α, when plug base 186 is threaded into abutment base receiving portion 164 along the entire length of plug base 186. According to some embodiments, the extent to which wings 154 are radially flexed is controlled by partial insertion of plug base 186, such that only a portion of its length is threaded into abutment base receiving portion 164, resulting in an angle α in a range between $α_{min}$ and its value in a resting position.

According to some embodiments, wings 154 are spring-biased against plug 180 when plug 180 positioned within abutment $150^h$.

Figure 27:
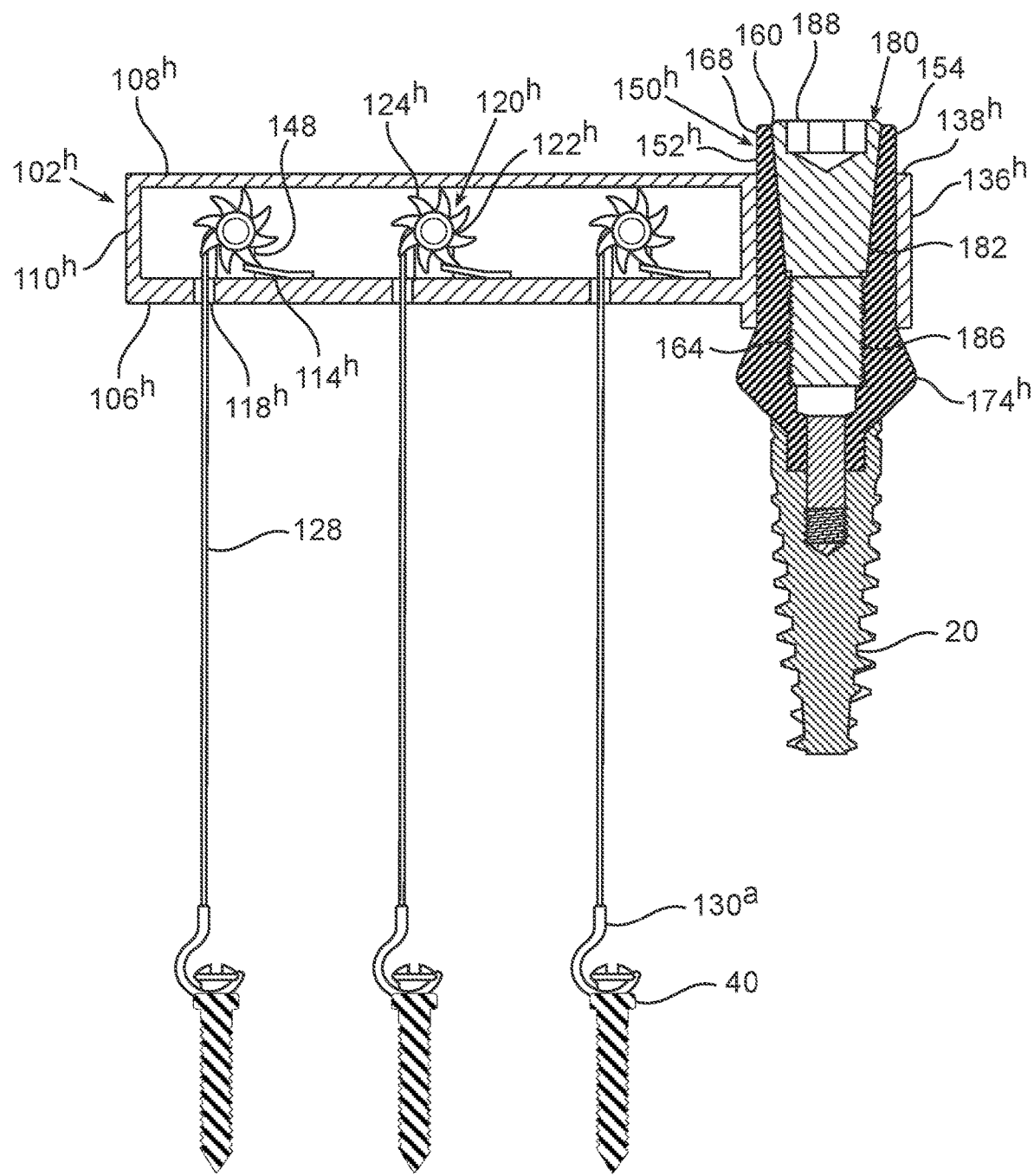
FIG. 27 constitutes a cross-sectional side view of a distraction device, engaged with an abutment connected to a bone screw.

FIG. 27 constitutes a cross-sectional side view of a distraction system $200^h$, according to some embodiments. Distraction system $200^h$ comprises distraction device $100^h$, abutment $150^h$, plug 180, bone screw 20 and at least one miniscrew 40. Bone screw 20 is provided with external threading at its proximal portion, configured for insertion and anchoring into a socket of a jaw bone. Bone screw 20 is further provided with internal threading (not numbered), configured to receive an internal screw (not numbered). Abutment $150^h$ is connected to bone screw 20, such that abutment proximal portion $176^h$ is placed within a matching socket (not numbered) of bone screw 20, and an internal screw (not numbered) is threaded through a channel of abutment $150^h$ into an internal threading (not numbered) provided in bone screw 20, while the wider head of the internal screw contacts a shoulder (not numbered) provided at the distal portion of said internal channel of abutment $150^h$.

Mounting member $138^h$ of distraction device $100^h$ is placed over abutment $150^h$ at a preferred position. According to some embodiments, a preferred position of distraction device $100^h$, selected by a user, includes either a preferred horizontal angle, a preferred vertical height along abutment distal portion $152^h$, or a combination of both.

Once distraction device $100^h$ is positioned at a preferred position, plug 180 is inserted into abutment distal receiving opening 160. According to some embodiments, an external tool such as a key or a wrench (not shown) is engaged with plug screw-head 188, utilized to exert rotary motion by which screw plug base 186 is screwed into abutment base receiving portion 164. Plug distal portion 182 forces wings 154 to expand radially, such that wing outer surfaces 168 press against or are spring-biased against inner wall of mounting bore $138^h$.

Advantageously, due to the presence of plug 180, the interference between wing outer surfaces 168 and the inner wall of mounting bore $138^h$ is stronger and capable of preventing occasional uncoupling of distraction device $100^h$ and abutment $150^h$ in the vertical direction, as well as preventing any undesired movement of distraction device $100^h$ in the horizontal plane.

Miniscrews, bone plates or dental implants 40 are configured for anchoring into a portion of a jawbone intended for distraction. FIG. 27 depicts an exemplary distraction system $200^h$, comprising a distraction device $100^h$ having three string pull assemblies $120^h$ and three matching miniscrews 40. Once the miniscrews 40 are inserted into a jawbone, string engagement portions 130, formed as hooks $130^a$ in FIG. 27, are engaged with receiving portions 42 of screws 40.

According to some embodiments, abutment $150^h$ is provided with plug 180, as described heretofore, and can be used with any embodiment of distraction device 100 described herein, such that abutment $150^h$ is configured to serve as an anchoring means to any other external device equipped with a receiving bore to receive abutment $150^h$ therein, whereby during insertion of plug 180 into abutment distal receiving opening 160, wings 184 are flexed radially outwards, as described heretofore, thereby affixing the other external device to abutment $150^h$ at a desired position and orientation.

It will be clear that a distraction device 100 according to the current disclosure, can include any combination between any embodiment of string positioning member 104, adaptor member 136 and string pull assemblies 120 described throughout the specification.

Figure 28A:
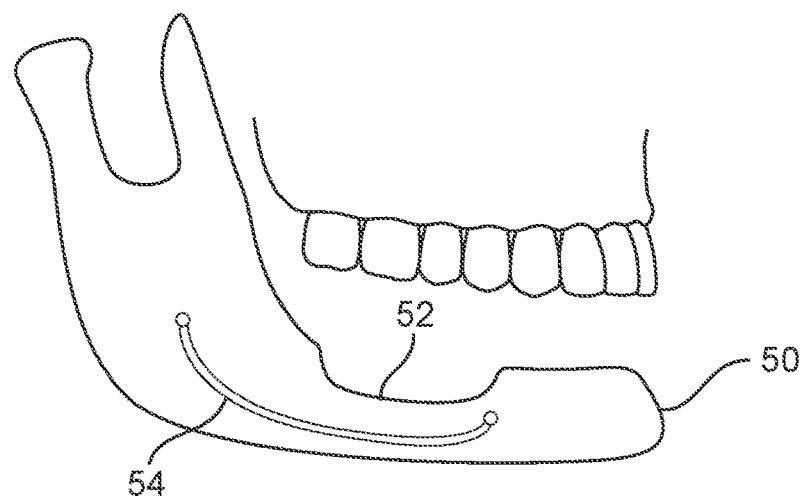
FIG. 28A constitutes a side view of the mandible with an alveolar ridge.
Figure 28B:
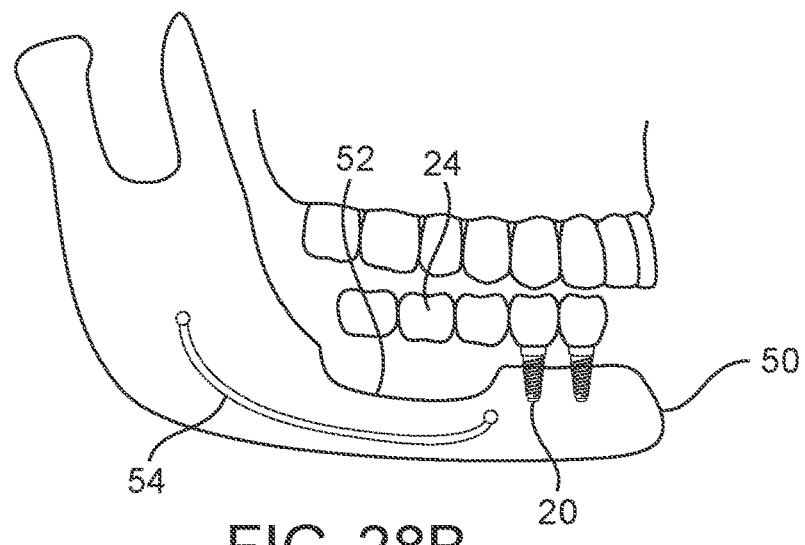
FIG. 28B constitutes a side view of the mandible of FIG. 28A.

Reference is now made to FIGS. 28A-28B, depicting a problem potentially solved by a distraction device 100 or a distraction system 200, as disclosed throughout the specification, according to some embodiments. FIG. 24A constitutes a side view of a mandible 50, with posterior alveolar ridge atrophy 52 above inferior alveolar nerve 54. In the illustrated example of FIG. 28A, the distance between the edge of alveolar ridge 52 and alveolar nerve 54 is too short to permit placement of a bone screw 20 therein, as during such placement, insertion of bone screw 20 too far through alveolar ridge 52, may contact and damage the alveolar nerve 54.

The terms "inferior alveolar nerve" and "alveolar nerve", as used herein, are interchangeable.

FIG. 28B constitutes a potential solution known in the art to the challenge presented in FIG. 28A, by anchoring an implant 20 to a region (not numbered) adjacent to alveolar ridge 52, supporting a dental bridge 24. The region of dental implantation is chosen to be such that there is sufficient bone to support implant 20, without contacting nerves, such as alveolar nerve 54. Dental bridge 24 is secured at one end to implant 20, or alternatively, by abutting a tooth if one is available in the same location (not illustrated). Dental bridge 24 may provide aesthetic resemblance of teeth covering the region of ridge atrophy 52. However, dental bridge 24 lacks support at its other end, opposing the end secured to implant 20. Therefore, such a solution may prove to be unstable over time and the dental bridge 24 may collapse due to external forces, for example during regular chewing or biting.

The terms "implant" and "dental screw", as used herein, are interchangeable, and refer to any conventional dental implant known in the art, or proprietary dental implants designed and configured to support a distraction device 100 or an abutment 150, as disclosed throughout the specification.

The terms "mandible" and "lower jaw", as used herein, are interchangeable.

The terms "maxilla" and "upper jaw", as used herein, are interchangeable.

The term "jaw bone", as used herein, refers to either the mandible or the maxilla.

Reference is now made to FIGS. 29A-35, depicting methods of using a distraction device 100 or a distraction system 200, according to some embodiments. FIG. 29A constitutes a side view of a mandible 50, wherein a bone screw 20 is anchored thereto, by any method known in the art for dental implantation. The region of dental implantation is a region adjacent to alveolar ridge 52, devoid of native teeth, chosen to be such that there is sufficient bone to support anchoring of bone screw 20, without bulging into nerves, such as alveolar nerve 54.

According to some embodiments, jaw bone such as mandible 50 includes native teeth adjacent to the site of bone screw 20 implantation (see FIG. 29A). According to some embodiments, jaw bone such as mandible 50 includes more than one bone screw 20, some of which may support dental crowns or dental bridges (see FIG. 29B). According to some embodiments, when jaw bone such as mandible 50 includes more than one bone screw 20, the bone screw 20 closest to ridge atrophy 52 is chosen to support a distraction device 100 for the procedure disclosed throughout the specification.

A crestal osteotomy line 56, created in a manner that does not harm alveolar nerve 54, separates between osteotomized bone segment 58 and the remaining basal bone of the mandible 50, as depicted in FIG. 29B.

According to some embodiments, the step of anchoring a bone screw 20 to a jaw bone, at a region adjacent to ridge atrophy 52 is performed prior to the step of creation of an osteotomy line 56. According to some embodiments, the step of creating an osteotomy line 56 is performed prior to the step of anchoring a bone screw 20 to a jaw bone, at a region adjacent to ridge atrophy 52.

At least one miniscrew 40 is anchored to osteotomized bone segment 58, as depicted in FIG. 29B. The optimal number of miniscrews 40 for obviously varies according to each particular clinical situation. FIG. 29C depicts an exemplary embodiments of two miniscrews 40a and 40b, anchored to osteotomized bone segment 58.

According to some embodiments, miniscrews 40 are shorter in length than bone screw 20. According to some embodiments, the length of the portion of miniscrew 40 engaged with osteotomized bone segment 58, is shorter than the distance between the edge of alveolar ridge 52 and osteotomy line 56, such that miniscrew 40 will not penetrate osteotomy line 56 when anchored to osteotomized bone segment 58. According to some embodiments, miniscrew 40 is an orthodontic screw.

According to some embodiment, a step of anchoring at least one miniscrew 40 to the jaw bone is performed after the step of creating osteotomy line 56, such that the location of osteotomy line 56 is chosen to be distanced adequately from the inferior alveolar nerve or the maxillary sinus cavity. Anchoring means such as bone plates or miniscrews 40 are placed safely after osteotomy due to the option of placing a protecting tool (not shown) in the osteotomy gap the prevents invasion of the anchoring means to the underosteotomy area in the mandible which houses the inferior alveolar nerve or the supraosteotomy area in the maxilla which is adjacent to the maxillary sinus cavity.

FIG. 29D depicts a further step of attaching an abutment 150 to bone screw 20. According to some embodiments, abutment 150 is any dental abutment known in the art, configured to engage with the bone screw 20 anchored to the jaw bone. According to some embodiments, abutment 150 refers to any embodiment thereof, as specified throughout the specification, configured to engage both with the bone screw 20 anchored to the jaw bone and with a distraction device 100.

FIG. 29E depicts a further step of attaching a distraction device 100 to abutment 150. Distraction device 100 refers to any embodiment thereof, as specified throughout the specification, configured to engage with abutment 150.

According to some embodiments, distraction device 100 is configured in its geometry to connect directly with a bone screw 20, without the aid of mediating abutment 150 (embodiment not shown). According to some embodiments, distraction device 100 is directly connected to a mount, such as an abutment, a dental crown, a dental screw, a dental bridge, a denture, a native tooth and the like.

According to some embodiments, placement of distraction device 100 either on abutment 150 or directly on bone screw 20 can be achieved at different horizontal orientation. According to some embodiments, a preferred horizontal orientation is selected such that frame 104 is aligned with osteotomized bone segment 58, or with miniscrews 40.

According to some embodiments, a preferred horizontal orientation is achieved by screwing adaptor member 136 having a bore screw thread 140 to a preferred lateral angle. According to some embodiments, a preferred horizontal orientation is achieved by placement of a polygonal mounting bore 138 at a preferred angle over a matching polygonal abutment distal portion 152. According to some embodiments, a preferred horizontal orientation is achieved by inserting a plug 180 into an abutment, such as abutment 150$^h$, while distraction device 100 is positioned at a preferred horizontal orientation.

According to some embodiments, placement of distraction device 100 on abutment 150 can be achieved at different vertical positions. According to some embodiments, distraction device 100 is configured not to extend vertically beyond the bite line, defined as the line or region separating between upper and lower teeth when a patient's mouth is closed.

According to some embodiments, a preferred vertical position is achieved by inserting a plug 180 into an abutment, such as abutment 150$^h$, while distraction device 100 is positioned at a preferred height over abutment distal portion 152, and more specifically over abutment distal portion 152$^h$.

A lateral angle, as used herein, refers to an angle in a horizontal plane.

Figure 29F:
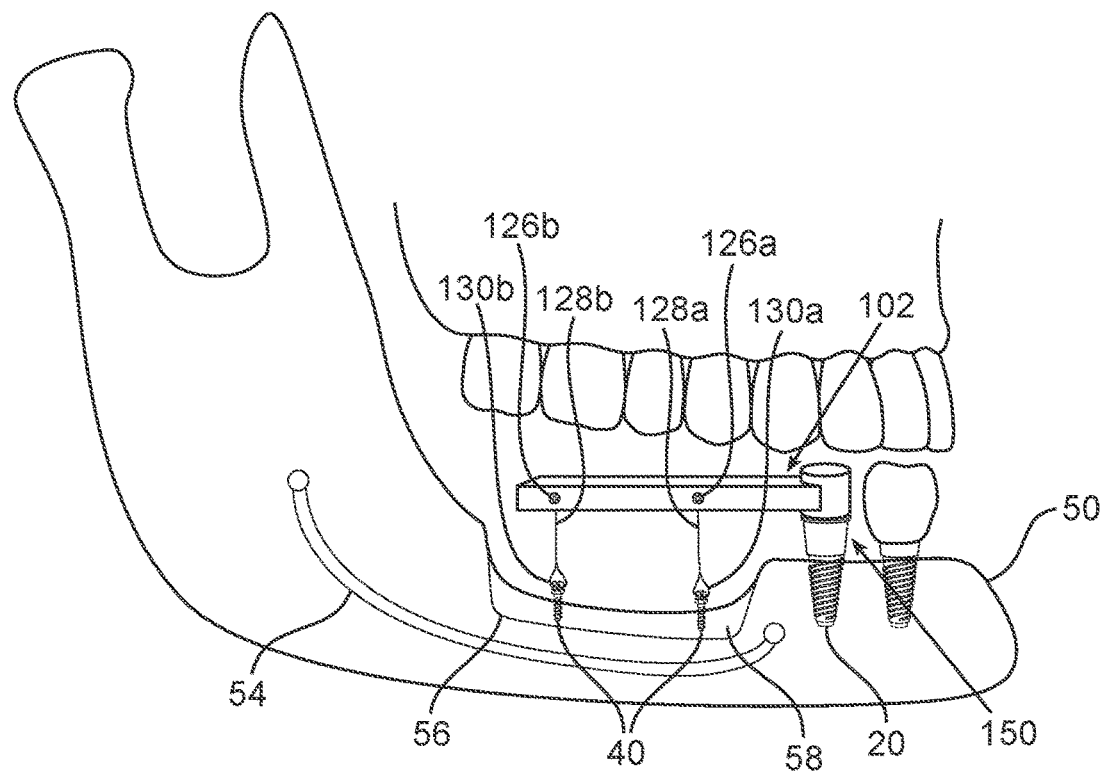
FIG. 29F constitutes a side view of the distraction device of FIG. 29E connected via strings to the miniscrews, at an initial position, according to some embodiments.

FIG. 29F depicts a further step of attaching at least one string engagement portion 130 to at least one miniscrew 40. According to some embodiments, the number of string pull assemblies 120 provided in distraction device 100 matches the number of miniscrews 40 anchored to the osteotomized bone segment 58, such that each string 128 is attached, via its string engagement portion 130, to a different miniscrew 40. FIG. 29F depicts an exemplary embodiment of a distraction device 100 provided with two string pull assemblies 120a and 120b, having respective strings 128a and 128b, attached via string engagement portions 130a and 130b to receiving portion 42a and 42b (not indicated in FIG. 29F) of miniscrews 40a and 40b, respectively.

According to some embodiments, string engagement portions 130 are provided in the form of loops (see FIG. 29F), which are engaged with receiving portions 42 of miniscrews 40. According to some embodiments, strings 128 are provided with open ended string engagement portions 130 (see FIG. 29E), which can be either knotted to create a loop prior to engagement with receiving portions 42 of miniscrews 40, or first threaded through receiving portions 42 of miniscrews 40, and then knotted to create loops that prevent disengagement of string engagement portions 130 from the receiving portions 42. According to some embodiments, string engagement portions 130 are provided in the form of hooks (see FIG. 27), which are engaged with receiving portions 42 of miniscrews 40.

After attachment of string engagement portions 130 to miniscrews 40, stretching of each string 128 between movable element 122 formed as a shaft and miniscrew 40 is achieved by rotating each corresponding movable element 122, via its tooling interface 126, such that string 128 is wrapped around movable element 122 until string 128 is fully stretched between movable element 122 and miniscrew 40. An initial position is defined as the position of osteotomized bone segment 58 when strings 128 are fully stretched on one hand, yet no displacement of osteotomized bone segment 58 has initiated on the other hand.

According to some embodiments, the shape of osteotomized bone segment 58 is variable, such that a plurality of miniscrews 40 may be anchored at different vertical heights, such that the distance between string positioning member 104 and at least one of miniscrews 40 is different from at least one other miniscrew 40. According to some embodiments, distraction device 100 may be positioned such that string positioning member 104 is not parallel to any plane passing through the receiving portions 42 of at least two of miniscrews 40, resulting in a distance between string positioning member 104 and at least one of miniscrews 40 being different from at least one other miniscrew 40.

Advantageously, each string pull assembly 120 is independent and may be operated separately, such that each string positioning member 122 can be rotated differently to achieve a desired goal of either stretching string 128 according to the specific distance between frame 104 and miniscrew 40, or moving each segment of osteotomized bone segment 58 corresponding to a specific miniscrew 40 at an appropriate paste or to an appropriate distance. A desired goal, including an appropriate pace and an appropriate distance, can vary by a user, such as a clinician, according to a clinical situation.

In the exemplary embodiment illustrated in FIG. 29F, two miniscrews 40 are anchored to osteotomized bone segment 58 at different vertical heights. Each of tooling interfaces 126a and 126b are rotated separately, potentially via the assistance of a rotation tool 76, until each of strings 128a and 128b, respectively, is fully stretched. The distance between string positioning member 104 and miniscrew 40a, along which string 128a is stretched, is longer in FIG. 29F than the distance between string positioning member 104 and miniscrew 40b, along which string 128b is stretched.

According to some embodiments, the amount of string pull assemblies 120 provided in distraction device 100 is larger than the number of miniscrews 40 anchored to the osteotomized bone segment 58 (embodiments not shown), such that only a fraction of string pull assemblies 120 are utilized, matching the number of miniscrews 40, while the remaining string pull assemblies 120 are unutilized throughout the procedure. According to some embodiments, strings 128 of unutilized string pull assemblies 120 are either cut or wrapped over their corresponding movable elements 122, so as to avoid interference with the procedure and minimize contact with the jaw, tongue and other regions of a patient's mouth unnecessarily.

Figure 29G:
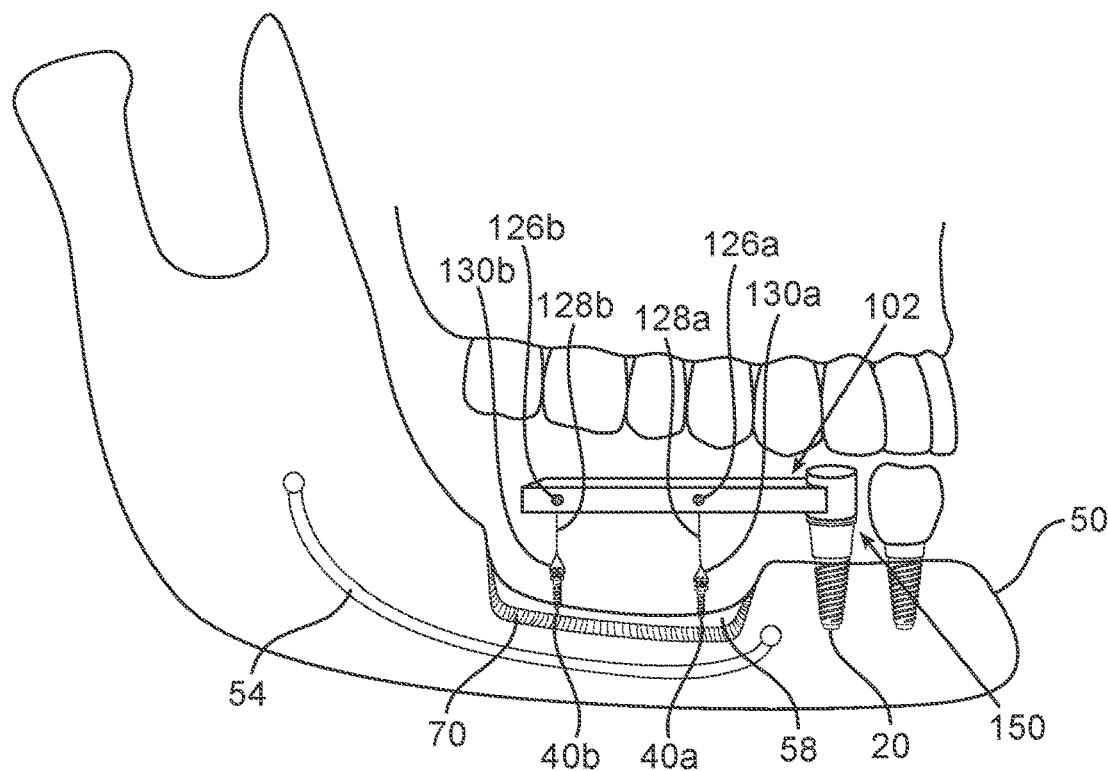
FIG. 29G constitutes a side view of new bone tissue formed in a gap between the osteotomized bone segment of FIG. 29C and basal jawbone, according to some embodiments.

FIG. 29G depicts a further step of distracting osteotomized bone segment 58 away from the basal bone of the mandible 50, by rotating the at least one of movable elements 122 via tooling interfaces 126. Each string 128 is wrapped around its movable elements 122 during its rotation wraps, resulting in a pull force acting on the miniscrew 40 attached thereto. Movement of osteotomized bone segment 58 corresponds to the movement of each of miniscrews 40 anchored thereto. According to some embodiments, rotation tool 76 is engaged with tooling interfaces 126 to facilitate turning thereof.

According to some embodiments, distracting osteotomized bone segment 58 includes repeating the step of rotating at least one shaft over a period of time defined as the distraction period of time. According to some embodiments, the distraction period of time spans over the course of a plurality of days. According to some embodiments, the distraction period of time spans over the course of a plurality of weeks. According to some embodiments, the distraction period of time spans over the course of a plurality of months. According to some embodiments, distracting osteotomized bone segment 58 occurs at least once a day during the period of time. According to some embodiments, distracting osteotomized bone segment 58 occurs at least twice a day during the period of time.

According to some embodiments, osteotomized bone segment 58 is distracted at a rate in a range of about 0.1 mm to 2 mm per day. According to some embodiments, osteotomized bone segment 58 is distracted at a rate in a range of about 0.3 mm to 1.5 mm per day. According to some embodiments, osteotomized bone segment 58 is distracted at a rate in a range of about 0.3 mm to 0.7 mm per day.

The term "about", as used herein, means "within ±10% of".

According to some embodiments, a full rotation of movable elements 122 via tooling interfaces 126 corresponds to a predefined distraction distance per revolution. According to some embodiments, the predefined distraction distance per revolution is about 1 mm. According to some embodiments, the predefined distraction distance per revolution is about 0.3 mm.

According to some embodiments, a protocol for use of revolution device 100 includes instructions for number of revolutions per day. According to some embodiments, a protocol for use of distraction device 100 includes instructions for a complete revolution once a day. According to some embodiments, a protocol for use of distraction device 100 includes instructions for a complete revolution twice a day. According to some embodiments, a protocol for use of distraction device 100 includes instructions for a half a revolution once a day. According to some embodiments, a protocol for use of distraction device 100 includes instructions for a half a revolution twice a day. According to some embodiments, a protocol for use of distraction device 100 includes instructions for a two revolutions once a day.

According to some embodiments, osteotomized bone segment 58 is distracted at a different rates over the distraction period of time. According to some embodiments, different movable elements 122, via corresponding tooling interfaces 126, are rotated at different rates.

Osteogenesis is promoted during the distraction period of time, as bone tissue 70 is formed between the distracted osteotomized bone segment 58 and the remaining jaw bone. Distraction rate is chosen by a user, such as a clinician, in order to promote formation and healing of bone tissue 70.

Figure 29H:
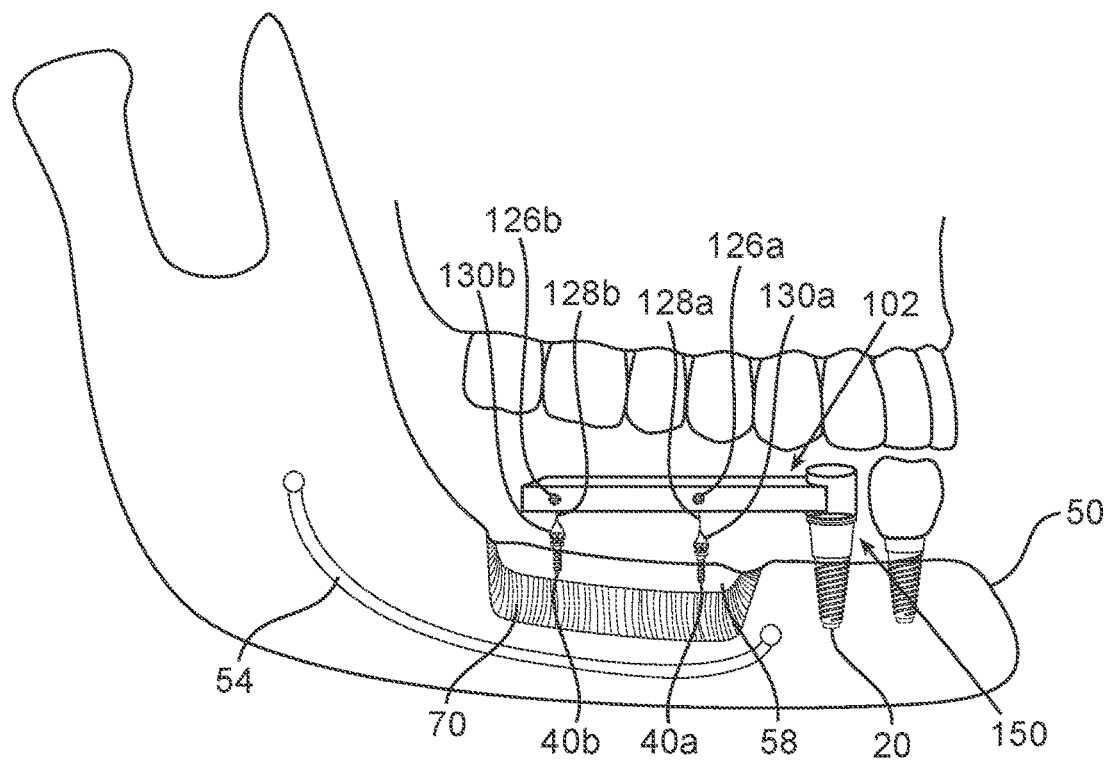
FIG. 29H constitutes a side view of new bone tissue formed in a gap between the osteotomized bone segment of FIG. 29C and basal jawbone, at a final position, according to some embodiments.
Figure 29I:
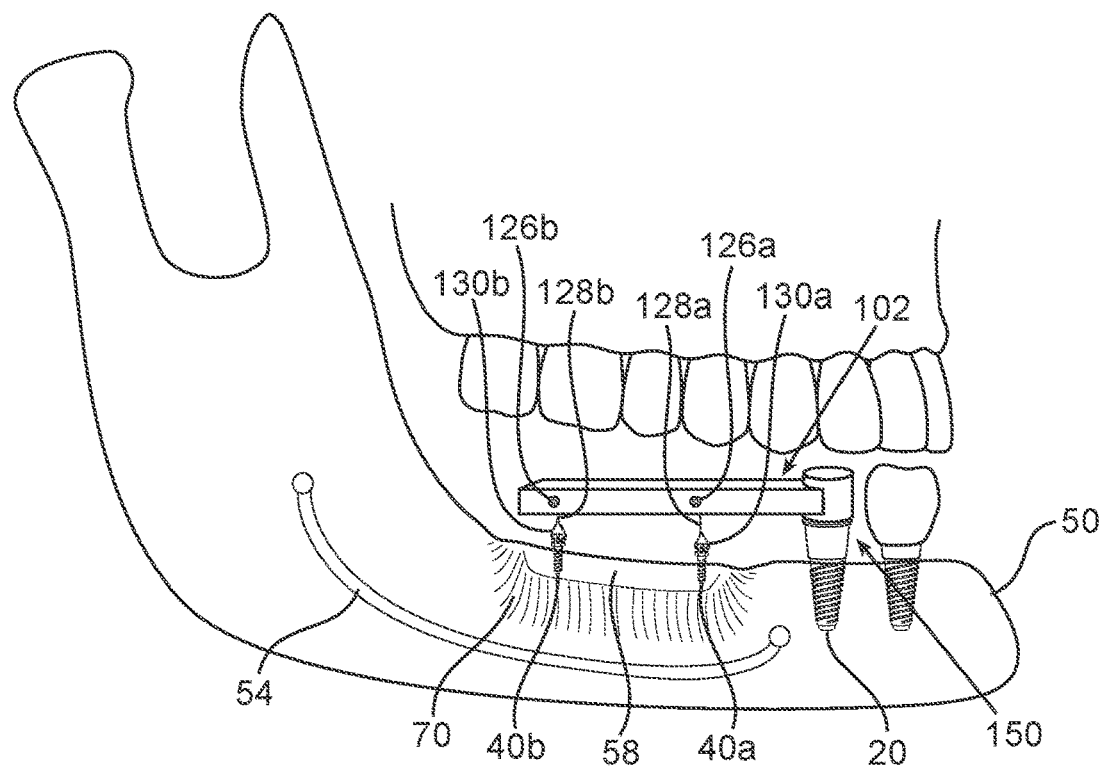
FIG. 29I constitutes a side view of the new bone tissue of FIG. 29H, at a final stage of healing and hardening to form a new bone segment, according to some embodiments.

The distraction period of time ends when osteotomized bone segment 58 reaches a preferred position, defined as a final position. FIG. 29H illustrates an exemplary final position, wherein the distal edge of osteotomized bone segment 58 is aligned with adjacent regions of the jaw bone. According to some embodiments, final position is a position at which enough bone is formed to allow anchoring implant 20 therein, without the risk of penetrating a nerve, such as alveolar nerve 54.

When a desired final position is reached, a consolidation phase follows in which distraction device 100, remaining attached via string 128 to miniscrews 40, keeps bone tissue 70 stable to allow the bone to fully heal, as depicted in FIG. 25I. According to some embodiments, consolidation phase spans over the course of a plurality of days. According to some embodiments, consolidation phase spans over the course of a plurality of weeks. According to some embodiments, consolidation phase spans over the course of a plurality of months. According to some embodiments, consolidation phase spans over the course three to seven days.

Figure 29J:
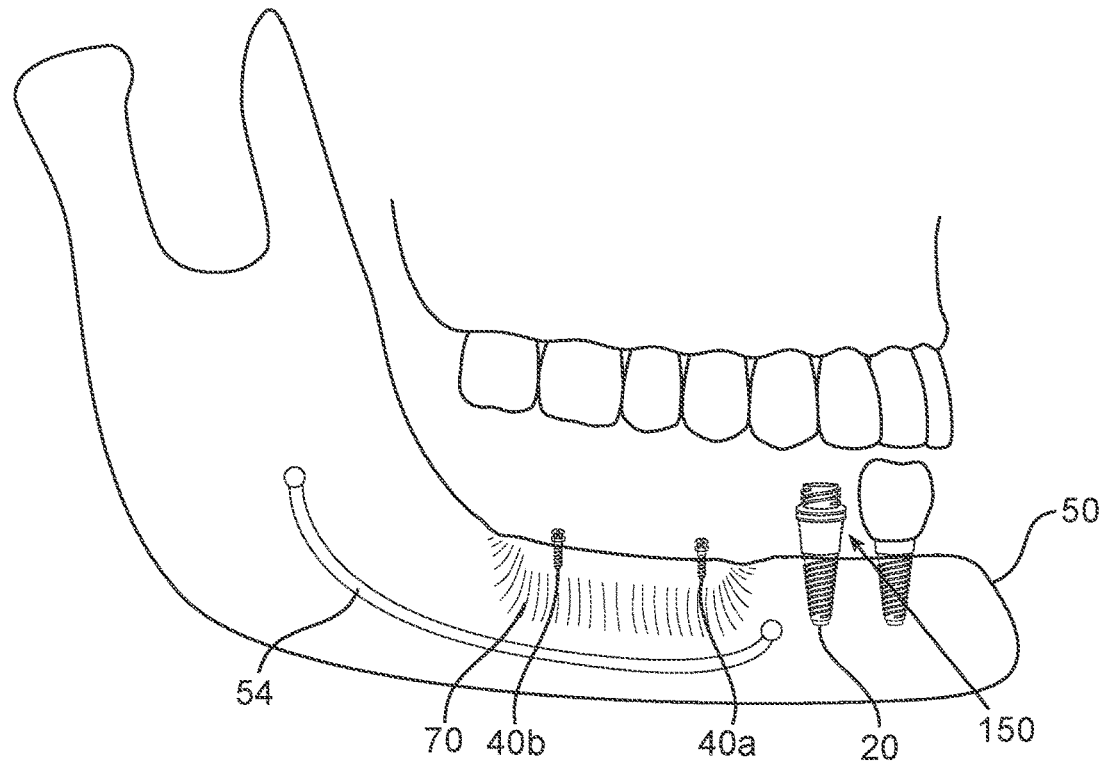
FIG. 29J constitutes a side view of the new bone segment of FIG. 29I, post removal of the distraction device, according to some embodiments.

FIG. 29J depicts a step of detachment of distraction device 100 from miniscrews 40, and its removal from either abutment 150 or bone screw 20. Removal of miniscrews 40 follows thereafter (step not illustrated separately).

Figure 29K:
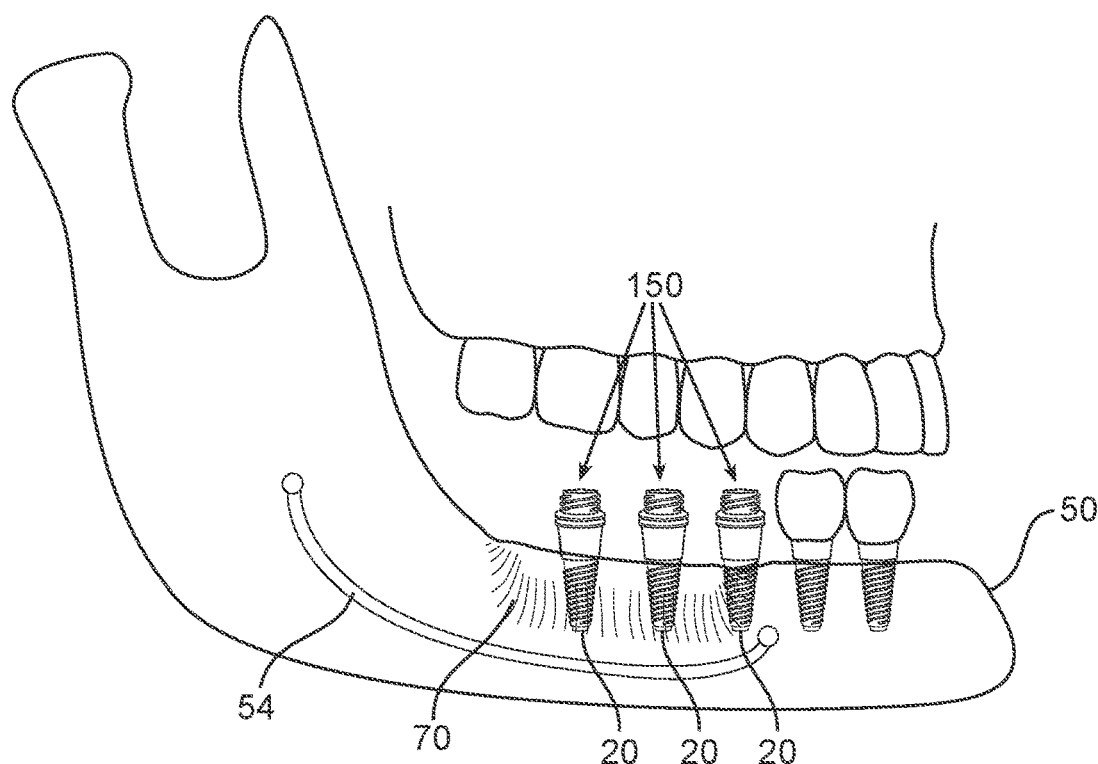
FIG. 29K constitutes a side view of bone screws being placed within the new bone tissue of FIG. 29J, according to some embodiments.
Figure 29L:
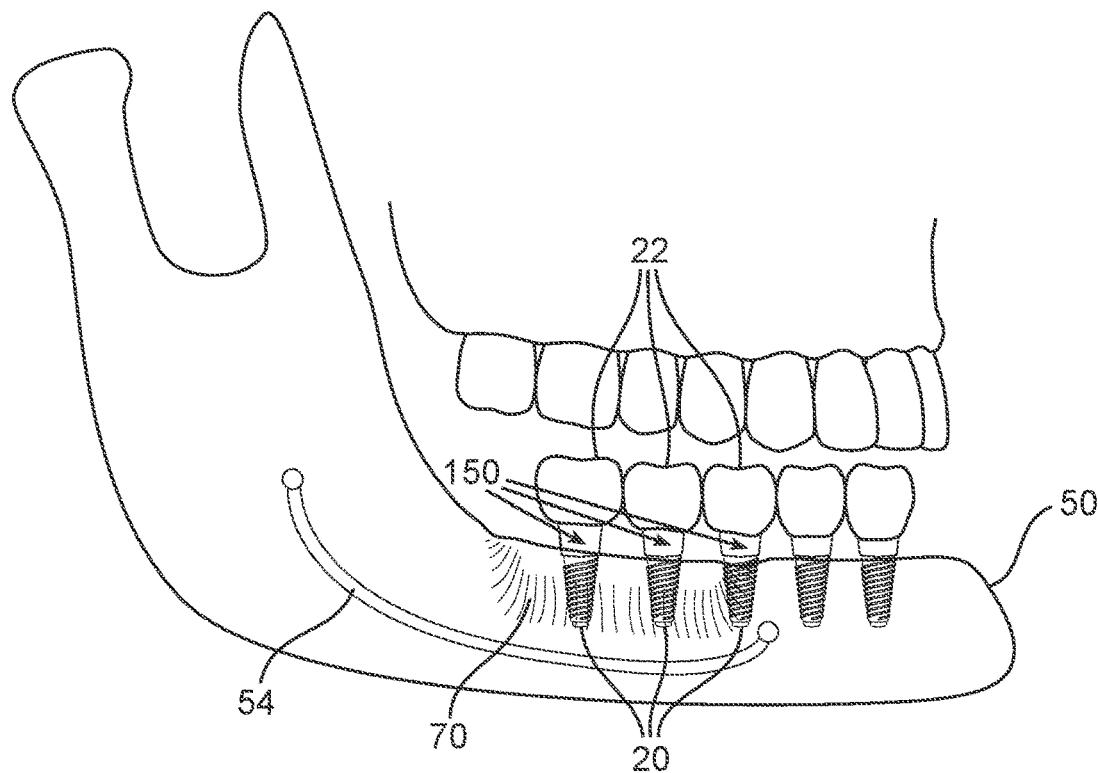
FIG. 29L constitutes a side view of dental crowns engaged with the bone screws of FIG. 29K, according to some embodiments.

Once a new bone 70 is formed, it is possible to anchor implants 20 therein, without a risk of penetrating a nerve, such as alveolar nerve 54. The number of bone screws 20 to be anchored obviously varies according to each particular clinical situation. FIG. 29K depicts an exemplary embodiment of a mandible having several implants 20, three of which are implants 20 anchored to a region formed with new rigid bone tissue 70. Such implants 20, as depicted in FIG. 29L, can support dental crowns 22.

Figure 30A:
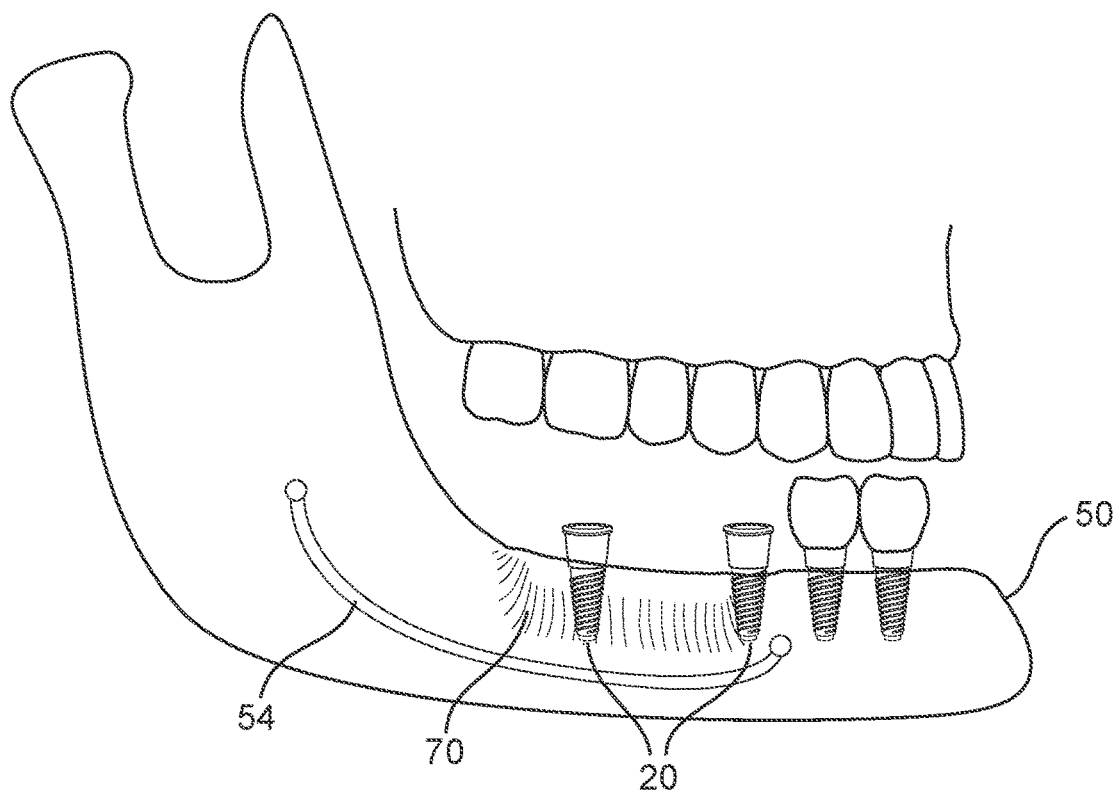
FIG. 30A constitutes a side view of spaced apart bone screws, being placed within the new bone tissue of FIG. 29J, according to some embodiments.
Figure 30B:
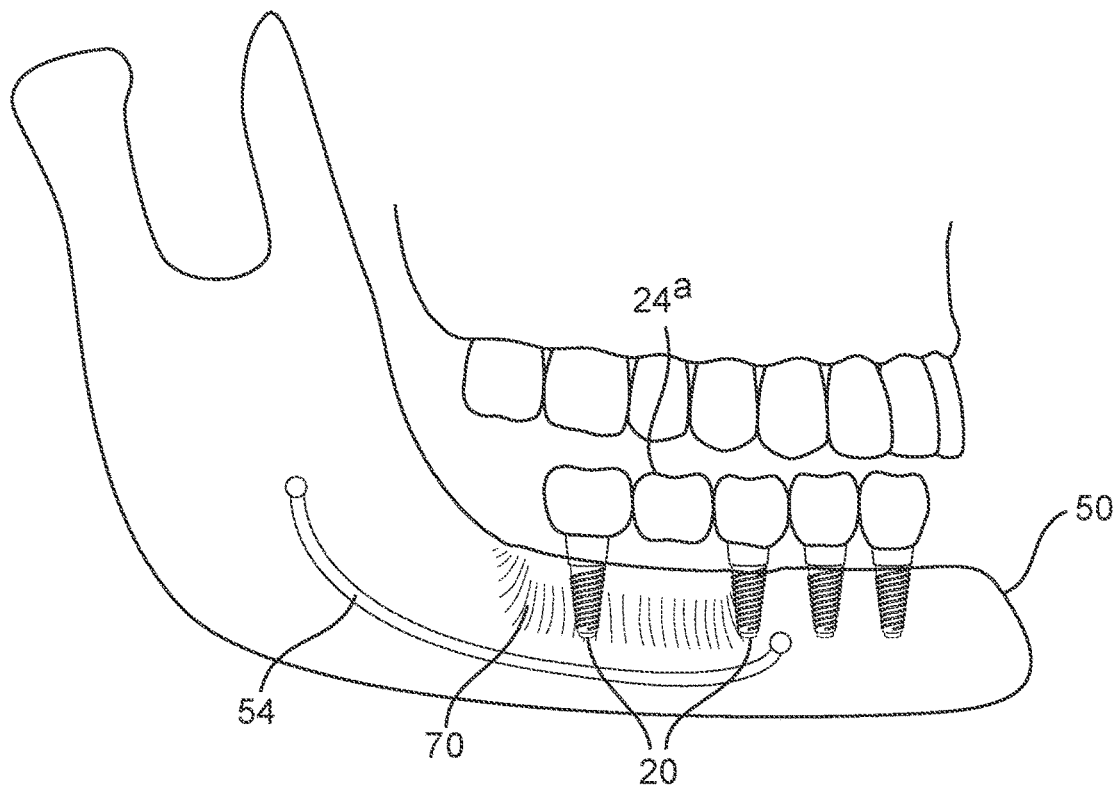
FIG. 30B constitutes a side view of dental bridge engaged with the bone screws of FIG. 30A, according to some embodiments.

According to some embodiments, implants 20 anchored within new rigid bone tissue 70 support a dental bridge. FIG. 30A depicts an exemplary embodiment of a mandible having several implants 20, two of which are implants 20 anchored to a region formed with new rigid bone tissue 70. Such implants 20, as depicted in FIG. 30B, support dental crown 24$^a$.

According to some embodiments, once the distraction procedure, utilizing distraction device 100 is completed, the anchored bone screw 20 used during the procedure to support abutment 150 or utilizing distraction device 100, serves as a support for a dental crown (see FIGS. 29K-30B) or alternatively, a dental bridge.

Figure 31A:
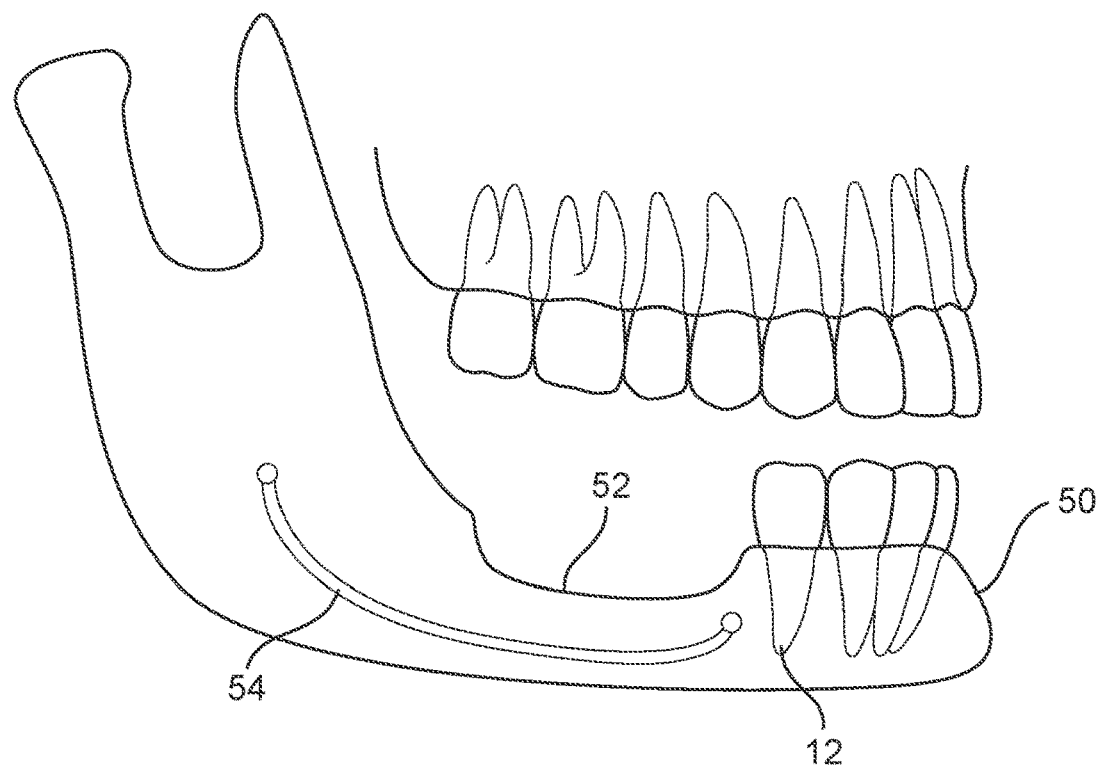
FIG. 31A constitutes a side view of the mandible, with healthy bones positioned adjacent to an alveolar ridge, according to some embodiments.
Figure 31B:
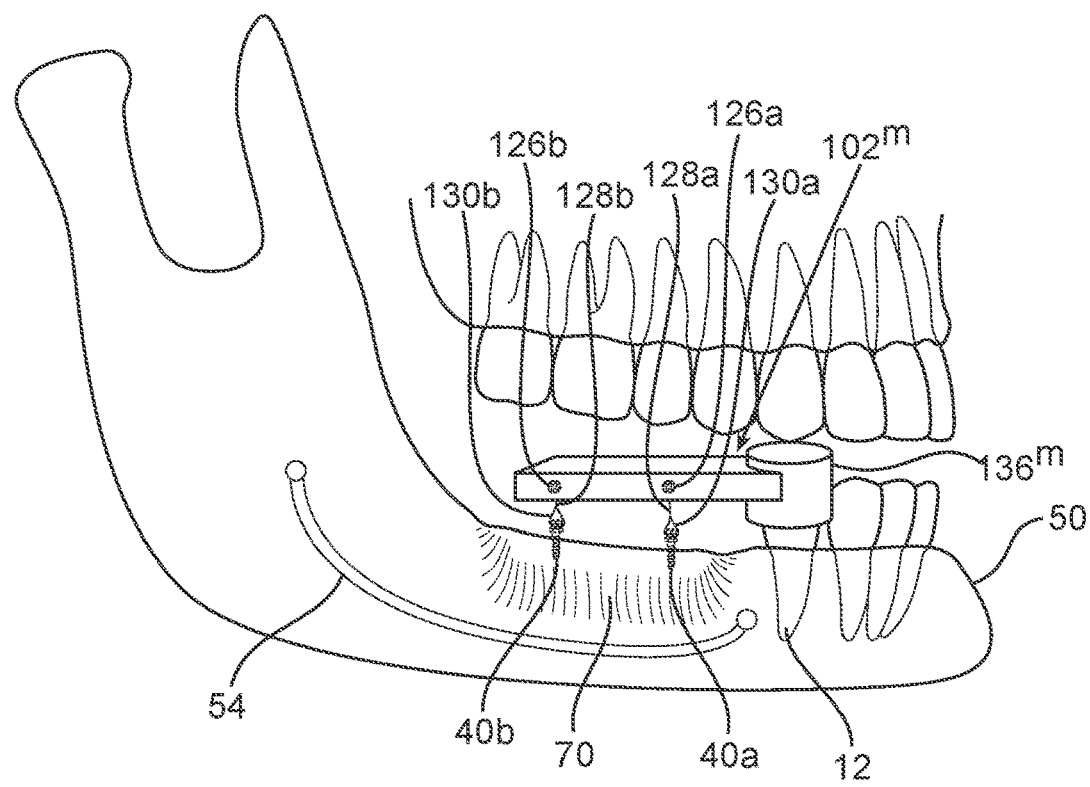
FIG. 31B constitutes a side view of distraction device engaged with a healthy bone, according to some embodiments.

FIG. 31A depicts a mandible 50 with native teeth 12 positioned adjacent to alveolar ridge 52. In the illustrated example, no region is available, absent of native teeth and adjacent to alveolar ridge 52, for anchoring a bone screw 20 to serve as a support for an abutment 150 or direct placement of a distraction device 100 thereon. FIG. 31B depicts an embodiment of a distraction device 100$^m$, comprising an adaptor member 136$^m$ provided with a socket or a bore (not visible in FIG. 31B), configured for secure attachment over native tooth 12 adjacent to alveolar ridge 52. According to some embodiments, adaptor member 136$^m$ is formed for engagement with native tooth 12 by any configuration known in the art for attaching a dental bridges to native teeth. Otherwise, distraction device 100$^m$ comprises any components described in previous embodiments, such as string positioning member 104 having at least one string pull assembly 120, configured for attachment via string 128 having a string engagement portion 130, to at least one miniscrew 40.

Figure 32:
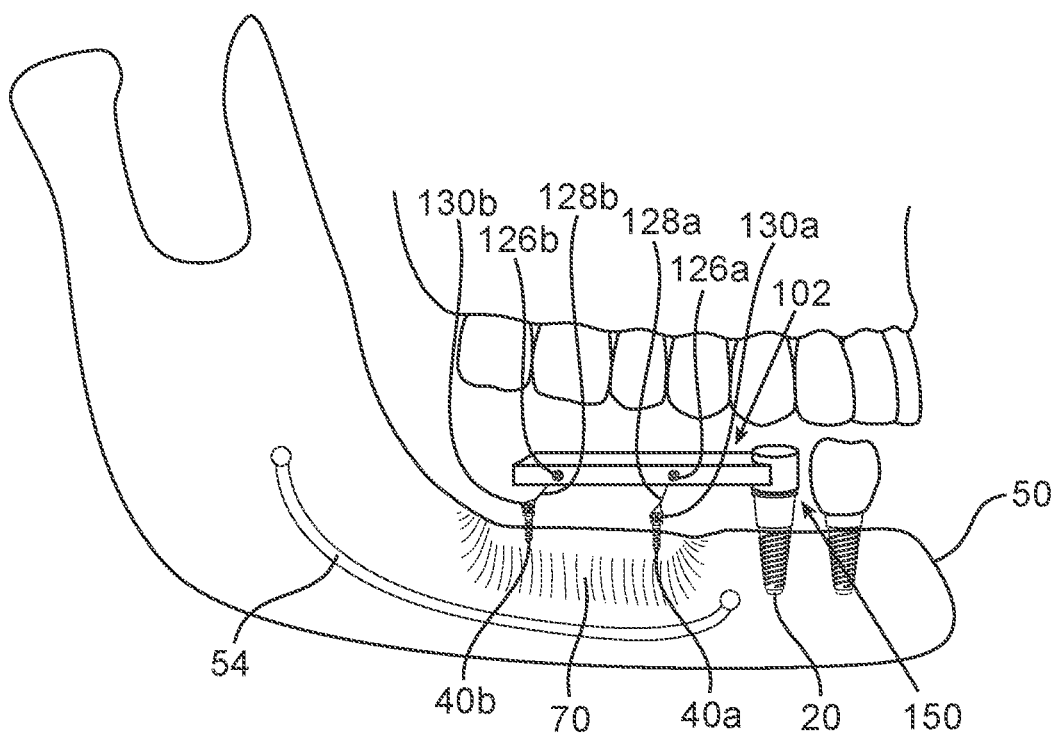
FIG. 32 constitutes a side view of the distraction device connected via strings at non-vertical angles to miniscrews, according to some embodiments.

According to some embodiments, the at least one string pull assembly 120 is not aligned with a corresponding miniscrew 40, such that the string 128, either when fully stretched or during the distraction period of time, is not necessarily vertical or horizontal but rather diagonal along the region between miniscrew 40 and movable element 122. FIG. 32 depicts an exemplary embodiment of two strings 128$a$ and 128$b$, diagonally stretched between miniscrews 40$a$ and 40$b$ to movable elements 122$a$ and 122$b$ (hidden from view), respectively. Each of strings 128$a$ and 128$b$ is stretched at a different angle, relative for example to a vertical projection line, to a longitudinal axis along the length of each corresponding miniscrew 40, or to a horizontal plane parallel for string positioning member 104.

Figure 33:
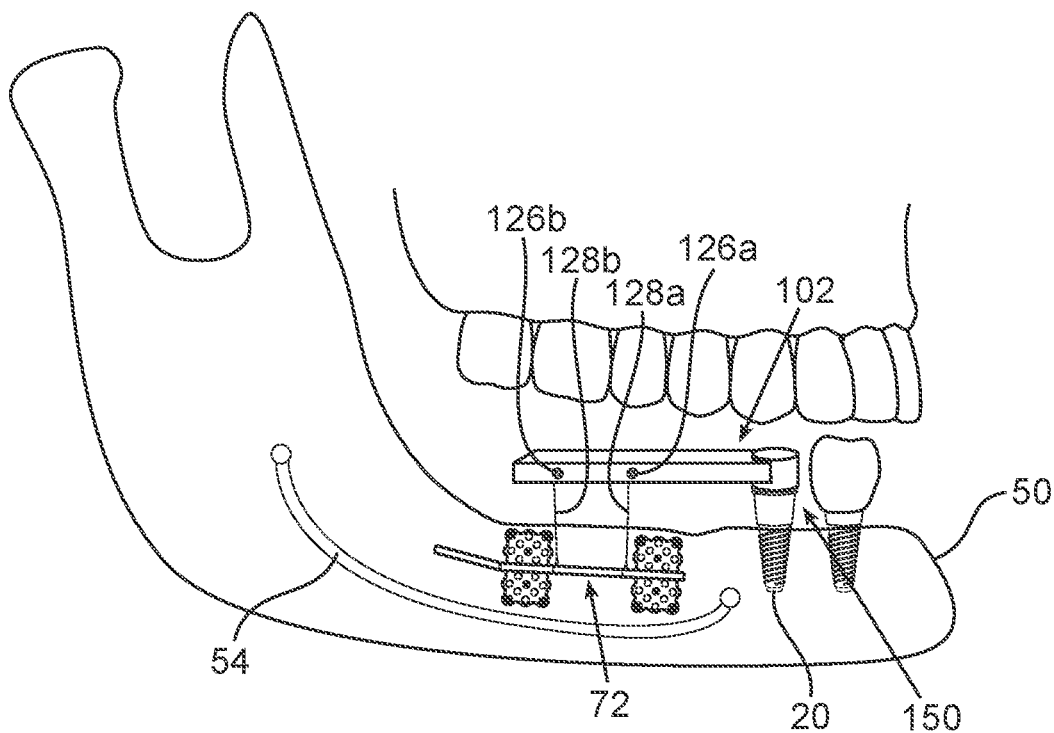
FIG. 33 constitutes a side view of the distraction device connected via strings to fixation plates, according to some embodiments.

According to some embodiments, distraction device 100 is attached via at least one string 128 to other fixation means anchored to an osteotomized bone segment 58, which are not necessarily miniscrews 40. FIG. 33 depicts an exemplary embodiment of a distraction device 100, attached via strings 128 to fixation plates 72. Fixation plates 72 comprise any fixation plates known in the art for procedures of distraction osteogenesis, having structural components to which strings 128 of a distraction device 100 can be attached.

Figure 34:
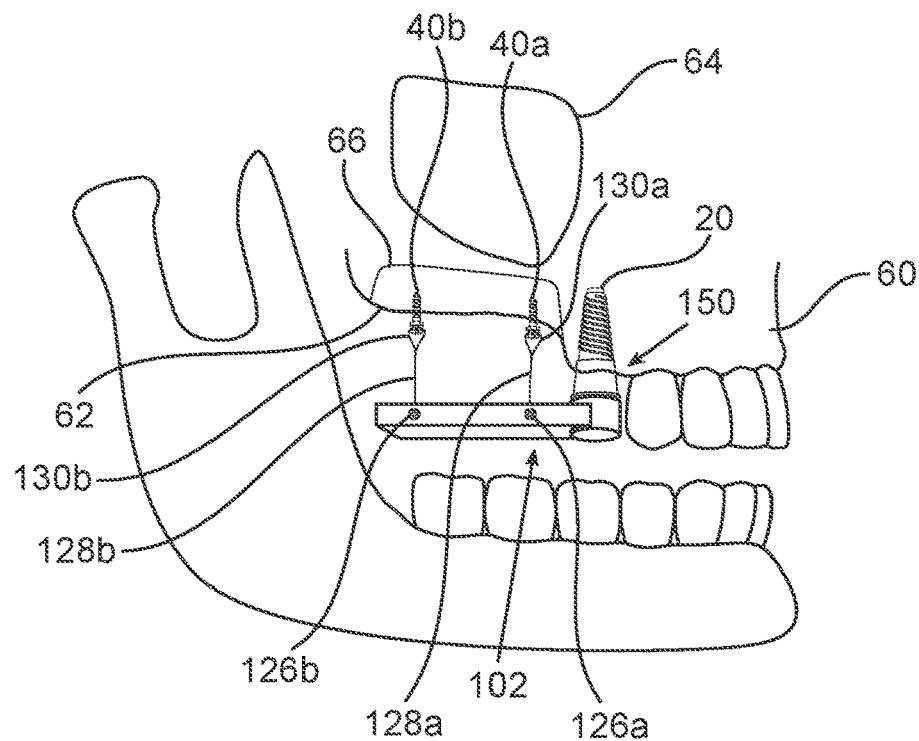
FIG. 34 constitutes a side view of the distraction device engaged with a bone screw in the maxilla, for distraction of an osteotomized bone segment in a sagittal portion of the maxilla, according to some embodiments.

According to some embodiments, distraction device 100 is used not only distraction procedures in the mandible, but other facial bones as well. FIG. 34 depicts a maxilla 60 with an alveolar ridge 62 in a sagittal portion thereof. The distance between the edge of alveolar ridge 62 and maxillary sinus 64 is too short to permit placement of a bone screw 20 therein, as during such placement, insertion of bone screw 20 too far through alveolar ridge 62, may damage the region of maxillary sinus 64, dislodged into the latter or have a low bone interface and anchorage due to the fact that only the bony interface offers anchorage. A distraction device 100 is attached, via abutment 150, to a bone screw 20 anchored to the maxilla 60 adjacent to an alveolar ridge 62. Strings 128 having string engagement portions 130 are attached to miniscrews 40, anchored to an osteotomized bone segment of alveolar ridge 62. Crestal osteotomy line 66 is formed distal to maxillary sinus 64. Otherwise, the method of using distraction device 100 for distraction of an osteotomized bone segment in the maxilla is carried out as described throughout the specification for use in the mandible.

Figure 35:
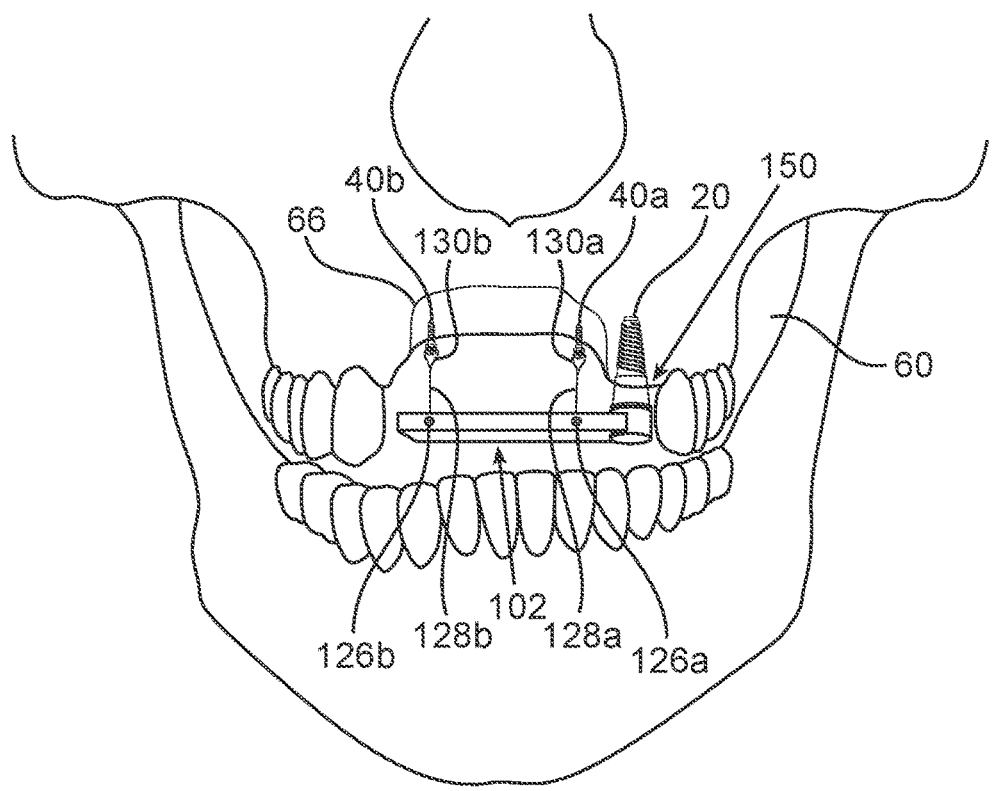
FIG. 35 constitutes a side view of the distraction device engaged with a bone screw in the maxilla, for distraction of an osteotomized bone segment in the frontal portion of the maxilla, according to some embodiments.

FIG. 35 depicts a midface portion of the upper jaw 60 with an alveolar ridge (not numbered). The distance between the edge of the alveolar ridge and the nasal crest (not numbered) is too short to permit placement of a bone screw 20 therein. A distraction device 100 is attached, via abutment 150, to a bone screw 20 anchored to the upper jaw 60 adjacent to the alveolar ridge. Strings 128 having string engagement portions 130 are attached to miniscrews 40, anchored to an osteotomized bone segment of the alveolar ridge. Crestal osteotomy line 66 is formed inferior to the nasal crest. Otherwise, the method of using distraction device 100 for distraction of an osteotomized bone segment in the midface portion of a jaw bone is carried out as described throughout the specification for use in the mandible.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A distraction device for bone tensioning, the distraction device comprising:
   (i) a main body comprising:
      at least one adaptor member having at least one connection platform;
      a strings positioning member attachable to the at least one adaptor member and extending along a longitudinal direction substantially perpendicular to a vertical axis of the at least one adaptor member, the strings positioning member comprising a plurality of positioning features, spaced from each other along the longitudinal direction; and
   (ii) a plurality of string pull assemblies, each comprising:
      a string having a first string end and a second string end, the second string end attached to a string engagement portion; and
      a movable element attached to the first string end, configured to move so as to promote displacement of the string engagement portion in a distal direction,
   wherein each of the plurality of string pull assemblies is attached to the main body;
   wherein each string of the plurality of string pull assemblies is configured to extend through or along a corresponding, different, positioning feature of the plurality of positioning features; and
   wherein each movable element of the plurality of string pull assemblies is independently movable to pull the string of the plurality of string pull assemblies attached thereto.

2. The distraction device of claim 1, wherein at least one string pull assembly of the plurality of string pull assemblies is attached to the strings positioning member.

3. The distraction device of claim 1, wherein at least one string pull assembly of the plurality of string pull assemblies is attached to the at least one adaptor member.

4. The distraction device of claim 3, wherein the strings positioning member further comprises at least one support rod.

5. The distraction device of claim 4, wherein at least one positioning feature of the plurality of positioning features is formed as a contact point between the string and the support rod.

6. The distraction device of claim 1, wherein the movable element is formed as a rotatable shaft, and wherein the plurality of string pull assemblies is rotateably attached to the main body.

7. The distraction device of claim 6, wherein at least one string pull assembly of the plurality of string pull assemblies further comprises a gear rigidly attached to the movable element, and the distraction device further comprises at least one pawl configured to engage with the gear, wherein the pawl is configured to allow free rotation of the at least one string pull assembly of the plurality of string pull assemblies in the one direction, while preventing its rotation in an opposite direction.

8. The distraction device of claim 1, wherein at least one positioning feature of the plurality of positioning features is formed as an aperture, configured to allow passage and free movement of the string there through.

9. The distraction device of claim 1, wherein the at least one connection platform comprises a mounting bore.

10. The distraction device of claim 9, wherein the mounting bore comprises a bore screw thread.

11. The distraction device of claim 9, wherein the mounting bore comprises an anti-rotational internal surface.

12. The distraction device of claim 9, wherein the at least one adaptor member further comprises a stationary ring portion and a dynamic ring portion hinged thereto, wherein the dynamic ring portion comprises a tightening mechanism configured to form the mounting bore by detachably attaching an end of dynamic ring portion to either the stationary ring portion or the strings positioning member.

13. The distraction device of claim 1, wherein at least one component of the distraction device is manufactured via the use of a CAD-CAM software, according to a design specific to a patient.

14. A distraction system, comprising:
   (i) the distraction device of claim 1; and
   (ii) an abutment comprising:
      an abutment distal portion, configured to engage with the at least one connection platform of the at least one adaptor member;
      an abutment proximal portion; and
      an abutment mid-portion, fluidly connected to the abutment distal portion and to the abutment proximal portion,
   wherein a largest cross-sectional diameter of the abutment mid-portion is larger than any of a largest cross-sectional diameter of the abutment distal portion, and a largest cross-sectional diameter of the abutment proximal portion.

15. The distraction system of claim 14, wherein the abutment proximal portion comprises a polyhedral-shaped structure.

16. The distraction system according claim 14, wherein the abutment distal portion comprises an abutment distal portion screw thread.

17. The distraction system according to claim 14, wherein the abutment distal portion comprises a polyhedral-shaped structure.

18. The distraction system of claim 14, further comprising at least one miniscrew, configured for engagement with the string engagement portion.

19. The distraction system of claim 14, further comprising a bone screw, configured to receive and securely engage with the abutment.

20. A distraction assembly comprising:
   (i) the distraction device of claim 1, wherein the at least one adaptor member further comprises a plurality of axial extensions, configured to bend radially inwards upon application of an external force along their circumference;
   (ii) a clamp comprising a band and a worm gear mechanism, the worm gear mechanisms configured to cause contraction or expansion of the clamp and keep the clamp at the adjusted position, wherein the clamp is configured to engage with the distraction device by placement thereof over an exterior of the at least one adaptor member; and wherein the clamp is further configured to exert force on the at least one adaptor member, which is sufficient to bend the plurality of axial extensions radially inwards.

\* \* \* \* \*